(12) United States Patent
Frankard et al.

(10) Patent No.: US 8,598,411 B2
(45) Date of Patent: **\*Dec. 3, 2013**

(54) PLANTS HAVING IMPROVED GROWTH CHARACTERISTICS AND A METHOD FOR MAKING THE SAME

(75) Inventors: Valerie Frankard, Sint-Genesius-Rode (BE); Christophe Reuzeau, Tocanc (FR)

(73) Assignee: Crop Design N.V., Zwijnaarde (BE)

( * ) Notice: Subject to any disclaimer, the term of this patent is extended or adjusted under 35 U.S.C. 154(b) by 0 days.

This patent is subject to a terminal disclaimer.

(21) Appl. No.: 12/924,203

(22) Filed: Sep. 22, 2010

(65) Prior Publication Data

US 2011/0209249 A1 Aug. 25, 2011

Related U.S. Application Data

(62) Division of application No. 11/060,029, filed on Feb. 17, 2005, now Pat. No. 7,825,293.

(60) Provisional application No. 60/576,250, filed on Jun. 2, 2004.

(30) Foreign Application Priority Data

May 28, 2004 (EP) .................................. 04102392

(51) Int. Cl.
 *C12N 15/82* (2006.01)
 *C12N 15/63* (2006.01)

(52) U.S. Cl.
 USPC .......................................... 800/278; 435/468

(58) Field of Classification Search
 None
 See application file for complete search history.

(56) References Cited

U.S. PATENT DOCUMENTS

2006/0253917 A1* 11/2006 Cooper ..................... 800/278

FOREIGN PATENT DOCUMENTS

| WO | WO9841642 | 9/1998 |
| WO | WO 01/85946 A2 * | 11/2001 |
| WO | WO 0185946 A2 | 11/2001 |
| WO | WO03025185 A1 | 3/2003 |
| WO | WO 2004/035798 A2 * | 4/2004 |
| WO | WO 2004035798 A2 | 4/2004 |

OTHER PUBLICATIONS

Ngo et al., (The Protein Folding Problem and Tertiary Structure Prediction, K. Merz., and S. Le Grand (eds.) pp. 492-495,1994).*
Wells, Biochemistry 29:8509-8517, 1990.*
Guo et al. (PNAS, 101: 9205-9210, 2004).*
Keskin et al. (Protein Science, 13:1043-1055, 2004).*
Thornton et al. (Nature structural Biology, structural genomics supplement, Nov. 2000, pp. 992-994).*
Vandepoele et al. (Plant Cell, 14: 903-916, 2002).*
Cooper et al. (Plant Molecular Biology, 53:273-279, 2003 ).*
Copper et al. (GenBank Sequence Accession No. AY224551; Published Mar. 30, 2003, pp. 1-2).*
Vandepoele et al., Plant Cell, 14:903-916, 2002.
Keskin et al., Protein Science, 13:1043-1055, 2004.
Guo et al., PNAS, 101:9205-9210, 2004.
Ngo et al., The Protein Folding Problem and Tertiary Structure Prediction, K. Merz and S. Le Grand, pp. 492-495, 1994.
Magyar, Zoltan et al., "Characterization of two distinct CP-related genes . . . ," FEBS Letters 486 (2000) 79-87.

* cited by examiner

*Primary Examiner* — Vinod Kumar
(74) *Attorney, Agent, or Firm* — Barbara E. Johnson, Esq.

(57) ABSTRACT

The present invention is a method for improving plant growth by increasing activity of DP protein in shoot tissue. The invention also relates to transgenic plants having improved growth characteristics, which plants have increased expression of a DP nucleic acid specifically in shoot-tissue. The increased expression of the nucleic acid encoding a DP protein, according to the methods of the present invention, may be mediated by a shoot-tissue-specific promoter.

5 Claims, 16 Drawing Sheets

Figure 1:
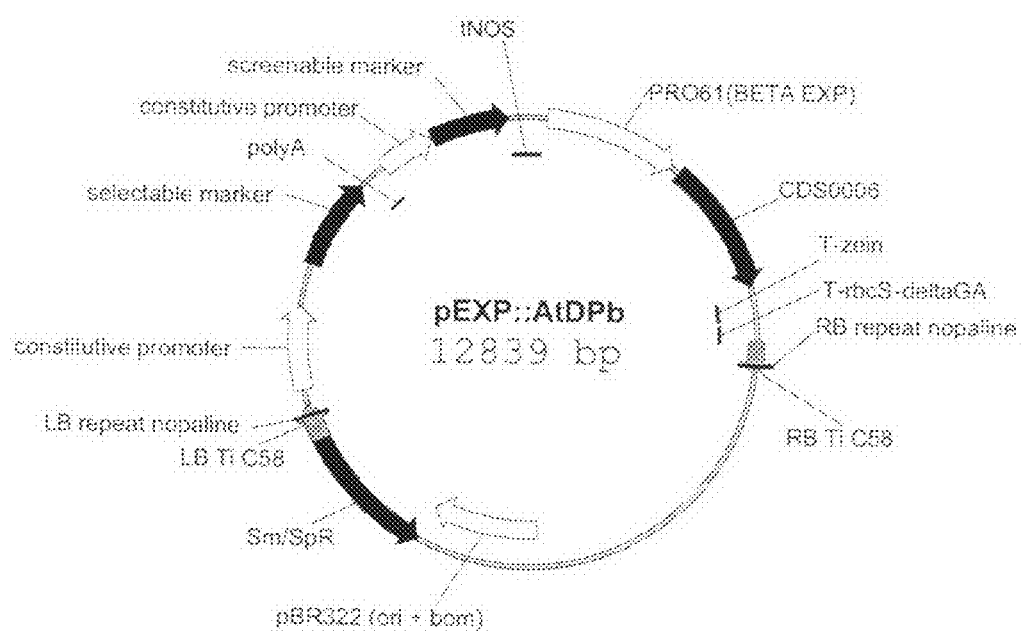

SEQ ID NO 1: coding sequence for *Arabidopsis thaliana* DPb protein (At5g03415)

ATGACAACTACTGGGTCTAATTCTAATCACAACCACCATGAAAGCAATAATAACAACAATAA
CCCTAGTACTAGGTCTTGGGGCACGGCGGTTTCAGGTCAATCTGTGTCTACTAGCGGCAGTA
TGGGCTCTCCGTCGAGCCGGAGTGAGCAAACCATCACCGTTGTTACATCTACTAGCGACACT
ACTTTTCAACGCCTGAATAATTTGGACATTCAAGGTGATGATGCTGGTTCTCAAGGAGCTTC
TGGTGTTAAGAAGAAGAAGAGGGGACAGCGTGCGGCTGGTCCAGATAAGACTGGAAGAGGAC
TACGTCAATTTAGTATGAAAGTTTGTGAAAAGGTGGAAAGCAAAGGAAGGACAACTTACAAT
GAGGTTGCAGACGAGCTTGTTGCTGAATTTGCACTTCCAAATAACGATGGAACATCCCCTGA
TCAGCAACAGTATGATGAGAAAAACATAAGACGAAGAGTATATGATGCTTTAAACGTCCTCA
TGGCTATGGATATAATATCCAAGGATAAAAAGAAATTCAATGGAGAGGTCTTCCTCGGACA
AGCTTAAGCGACATTGAAGAATTAAAGAACGAACGACTCTCACTTAGGAACAGAATTGAGAA
GAAAACTGCATATTCCCAAGAACTGGAAGAACAATATGTAGGCCTTCAGAATCTGATACAGA
GAAATGAGCACTTATATAGCTCAGGAAATGCTCCCAGTGGCGGTGTTGCTCTTCCTTTTATC
CTTGTCCAGACTCGTCCTCACGCAACAGTAGAAGTGGAGATATCAGAAGATATGCAGCTCGT
GCATTTTGATTTCAACAGCACTCCATTTGAGCTCCACGACGACAATTTTGTCCTCAAGACTA
TGAAGTTTTGTGATCAACCGCCGCAACAACCAAACGGTCGGAACAACAGCCAGCTGGTTTGT
CACAATTTCACGCCAGAAAACCCTAACAAAGGCCCCAGCACAGGTCCAACACCGCAGCTGGA
TATGTACGAGACTCATCTTCAATCGCAACAACATCAGCAGCATTCTCAGCTACAAATCATTC
CTATGCCTGAGACTAACAACGTTACTTCCAGCGCTGATACTGCTCCAGTGAAATCCCCGTCT
CTTCCAGGGATAATGAACTCCAGCATGAAGCCGGAGAATTGA

SEQ ID NO 2: *Arabidopsis thaliana* DPb protein, 385 aa, (At5g03415)

MTTTGSNSNHNHHESNNNNNNPSTRSWGTAVSGQSVSTSGSMGSPSSRSEQTITVVTSTSDT
TFQRLNNLDIQGDDAGSQGASGVKKKKRGQRAAGPDKTGRGLRQFSMKV<u>CEKVESKGRTTYN
EVADELVAEFALPNNDGTSPDQQQYDEKNIRRRVYDALNVLMAMDIISKDKKEIQWRGLPRT
SLSDIEELKNERLSLRNRIEKKTAYSQELEEQYVGLQNLIQRNEHLYSSGNAPSGGVALPFI
LVQTRPHATVEVE</u>ISEDMQLVHFDFNSTPFELHDDNFVLKTMKFCDQPPQQPNGRNNSQLVC
HNFTPENPNKGPSTGPTPQLDMYETHLQSQQHQQHSQLQIIPMPETNNVTSSADTAPVKSPS
LPGIMNSSMKPEN

FIGURE 2

SEQ ID NO 3: coding sequence for *Arabidopsis thaliana* DPb protein (LIMS prediction with introns)

```
TCAAAATCAGAAACTTTCCTTGACAAATTTTAACAAATCTCTTTCTCGTTTTCTATTGAATT
CTCCAGTAGCGCGGTAGTTAGTTTTAGGTGGAAGAAGAATGACAACTACTGGGTCTAATTCT
AATCACAACCACCATGAAAGCAATAATAACAACAATAACCCTAGTACTAGGTCTTGGGGCAC
GGCGGTTTCAGGTCAATCTGTGTCTACTAGCGGCAGTATGGGCTCTCCGTCGAGCCGGAGTG
AGCAAACCATCACCGTTGTTACATCTACTAGCGACACTACTTTTCAACGCCTGAATAATTTG
GACATTCAAGGTGATGATGCTGGTTCTCAAGGAGCTTCTGGTGTTAAGAAGAAGAAGAGGGG
ACAGCGTGCGGCTGGTCCAGATAAGACTGGAAGAGGACTACGTCAATTTAGTATGAAAGGTC
TTATCTCTTTCTCTGCCCCTATTATGCTTTCATCTAAATGCCTTTCAATTTGTGAAAAGGTG
GAAAGCAAAGGAAGGACAACTTACAATGAGGTTGCAGACGAGCTTGTTGCTGAATTTGCACT
TCCAAATAACGATGGAACATCCCCTGATCAGCAACAGTATGATGAGAAAAACATAAGACGAA
GAGTATATGATGCTTTAAACGTCCTCATGGCTATGGATATAATATCCAAGGATAAAAAAGAA
ATTCAATGGAGAGGTCTTCCTCGGACAAGCTTAAGCGACATTGAAGAATTAAAGAACGAACG
ACTCTCACTTAGGAACAGAATTGAGAAGAAAACTGCATATTCCCAAGAACTGGAAGAACAAG
TAATGAACATCATCGATACTCTCGGCTTATCTGCTTCCTGCCTTCAGAATCTGATACAGAGA
AATGAGCACTTATATAGCTCAGGAAATGCTCCCAGTGGCGGTGTTGCTCTTCCTTTTATCCT
TGTCCAGACTCGTCCTCACGCAACAGTAGAAGTGGAGATATCAGAAGATATGCAGCTCGTGC
ATTTTGATTTCAACAGCACTCCATTTGAGCTCCACGACGACAATTTTGTCCTCAAGACTATG
AAGTTTTGTGATCAACCGCCGCAACAACCAAACGGTCGGAACAACAGCCAGCTGGTTTGTCA
CAATTTCACGCCAGAAAACCCTAACAAAGGCCCCAGCACAGGTCCAACACCGCAGCTGGATA
TGTACGAGACTCATCTTCAATCGCAACAACATCAGCAGCATTCTCAGCTACAAATCATTCCT
ATGCCTGAGACTAACAACGTTACTTCCAGCGCTGATACTGCTCCAGTGAAATCCCCGTCTCT
TCCAGGGATAATGAACTCCAGCATGAAGCCGGAGAATTGAAACACGTATGAAGGCCCCTTGT
ACAATTTCTGTAAAACTGTAAAGTAGCTCTTGAAAAACTTTACCTGGTTTTTTGACGAATAG
TCTGTTTAGCGGTAAA
```

SEQ ID NO 4: *Arabidopsis thaliana* DPb protein, 413 aa, (LIMS prediction with introns)

```
MTTTGSNSNHNHHESNNNNNNPSTRSWGTAVSGQSVSTSGSMGSPSSRSEQTITVVTSTSDT
TFQRLNNLDIQGDDAGSQGASGVKKKKRGQRAAGPDKTGRGLRQFSMKGLISFSAPIMLSSK
CLSICEKVESKGRTTYNEVADELVAEFALPNNDGTSPDQQQYDEKNIRRRVYDALNVLMAMD
IISKDKKEIQWRGLPRTSLSDIEELKNERLSLRNRIEKKTAYSQELEEQVMNIIDTLGLSAS
CLQNLIQRNEHLYSSGNAPSGGVALPFILVQTRPHATVEVEISEDMQLVHFDFNSTPFELHD
DNFVLKTMKFCDQPPQQPNGRNNSQLVCHNFTPENPNKGPSTGPTPQLDMYETHLQSQQHQQ
HSQLQIIPMPETNNVTSSADTAPVKSPSLPGIMNSSMKPEN
```

FIGURE 2 (continued)

SEQ ID NO 5: primer primer forward

*GGGGACAAGTTTGTACAAAAAAGCAGGCTTCAC*AATGACAACTACTGGGTCTAATTCT

SEQ ID NO 6: primer primer reverse
*GGGGACCACTTTGTACAAGAAAGCTGGGT*TCAATTCTCCGGCTTCAT

SEQ ID NO 7: rice beta-expansin promoter EXPB9

AAAACCACCGAGGGACCTGATCTGCACCGGTTTTGATAGTTGAGGGACCCGTTGTGTCTGGT
TTTCCGATCGAGGGACGAAAATCGGATTCGGTGTAAAGTTAAGGGACCTCAGATGAACTTAT
TCCGGAGCATGATTGGGAAGGGAGGACATAAGGCCCATGTCGCATGTGTTTGGACGGTCCAG
ATCTCCAGATCACTCAGCAGGATCGGCCGCGTTCGCGTAGCACCCGCGGTTTGATTCGGCTT
CCCGCAAGGCGGCGGCCGGTGGCCGTGCCGCCGTAGCTTCCGCCGGAAGCGAGCACGCCGCC
GCCGCCGACCCGGCTCTGCGTTTGCACCGCCTTGCACGCGATACATCGGGATAGATAGCTAC
TACTCTCTCCGTTTCACAATGTAAATCATTCTACTATTTTCCACATTCATATTGATGTTAAT
GAATATAGACATATATATCTATTTAGATTCATTAACATCAATATGAATGTAGGAAATGCTAG
AATGACTTACATTGTGAATTGTGAAATGGACGAAGTACCTACGATGGATGGATGCAGGATCA
TGAAAGAATTAATGCAAGATCGTATCTGCCGCATGCAAAATCTTACTAATTGCGCTGCATAT
ATGCATGACAGCCTGCATGCGGGCGTGTAAGCGTGTTCATCCATTAGGAAGTAACCTTGTCA
TTACTTATACCAGTACTACATACTATATAGTATTGATTTCATGAGCAAATCTACAAAACTGG
AAAGCAATAAGAAATACGGGACTGGAAAAGACTCAACATTAATCACCAAATATTTCGCCTTC
TCCAGCAGAATATATATCTCTCCATCTTGATCACTGTACACACTGACAGTGTACGCATAAAC
GCAGCAGCCAGCTTAACTGTCGTCTCACCGTCGCACACTGGCCTTCCATCTCAGGCTAGCTT
TCTCAGCCACCCATCGTACATGTCAACTCGGCGCGCGCACAGGCACAAATTACGTACAAAAC
GCATGACCAAATCAAAACCACCGGAGAAGAATCGCTCCCGCGCGCGGCGGCGACGCGCACGT
ACGAACGCACGCACGCACGCCCAACCCCACGACACGATCGCGCGCGACGCCGGCGACACCGG
CCGTCCACCCGCGCCCTCACCTCGCCGACTATAAATACGTAGGCATCTGCTTGATCTTGTCA
TCCATCTCACCACCAAAAAAAAAGGAAAAAAAAACAAAACACACCAAGCCAAATAAAAGCG
ACA

SEQ ID NO 8: Sequence of the [PRO061 (rice beta-expansine promoter- CDS0006(AtDPb)- terminator (T-zein and T-rbcS-deltaGA)] expression cassette

<u>AAAACCACCGAGGGACCTGATCTGCACCGGTTTTGATAGTTGAGGGACCCGTTGTGTCTGGT</u>
<u>TTTCCGATCGAGGGACGAAAATCGGATTCGGTGTAAAGTTAAGGGACCTCAGATGAACTTAT</u>
<u>TCCGGAGCATGATTGGGAAGGGAGGACATAAGGCCCATGTCGCATGTGTTTGGACGGTCCAG</u>
<u>ATCTCCAGATCACTCAGCAGGATCGGCCGCGTTCGCGTAGCACCCGCGGTTTGATTCGGCTT</u>
<u>CCCGCAAGGCGGCGGCCGGTGGCCGTGCCGCCGTAGCTTCCGCCGGAAGCGAGCACGCCGCC</u>

FIGURE 2 (cotinued)

```
GCCGCCGACCCGGCTCTGCGTTTGCACCGCCTTGCACGCGATACATCGGGATAGATAGCTAC
TACTCTCTCCGTTTCACAATGTAAATCATTCTACTATTTTCCACATTCATATTGATGTTAAT
GAATATAGACATATATATCTATTTAGATTCATTAACATCAATATGAATGTAGGAAATGCTAG
AATGACTTACATTGTGAATTGTGAAATGGACGAAGTACCTACGATGGATGGATGCAGGATCA
TGAAAGAATTAATGCAAGATCGTATCTGCCGCATGCAAAATCTTACTAATTGCGCTGCATAT
ATGCATGACAGCCTGCATGCGGGCGTGTAAGCGTGTTCATCCATTAGGAAGTAACCTTGTCA
TTACTTATACCAGTACTACATACTATATAGTATTGATTTCATGAGCAAATCTACAAAACTGG
AAAGCAATAAGAAATACGGGACTGGAAAAGACTCAACATTAATCACCAAATATTTCGCCTTC
TCCAGCAGAATATATATCTCTCCATCTTGATCACTGTACACACTGACAGTGTACGCATAAAC
GCAGCAGCCAGCTTAACTGTCGTCTCACCGTCGCACACTGGCCTTCCATCTCAGGCTAGCTT
TCTCAGCCACCCATCGTACATGTCAACTCGGCGCGCGCACAGGCACAAATTACGTACAAAAC
GCATGACCAAATCAAAACCACCGGAGAAGAATCGCTCCCGCGCGCGGCGGCGACGCGCACGT
ACGAACGCACGCACGCACGCCCAACCCCACGACACGATCGCGCGCGACGCCGGCGACACCGG
CCGTCCACCCGCGCCCTCACCTCGCCGACTATAAATACGTAGGCATCTGCTTGATCTTGTCA
TCCATCTCACCACCAAAAAAAAAGGAAAAAAAAACAAAACACACCAAGCCAAATAAAAGCG
ACAATTTAAATCAACTAGGGATATACAAGTTTGTACAAAAAAGCAGGCTTCACAATGACAA
CTACTGGGTCTAATTCTAATCACAACCACCATGAAAGCAATAATAACAACAATAACCCTAGT
ACTAGGTCTTGGGGCACGGCGGTTTCAGGTCAATCTGTGTCTACTAGCGGCAGTATGGGCTC
TCCGTCGAGCCGGAGTGAGCAAACCATCACCGTTGTTACATCTACTAGCGACACTACTTTTC
AACGCCTGAATAATTTGGACATTCAAGGTGATGATGCTGGTTCTCAAGGAGCTTCTGGTGTT
AAGAAGAAGAAGAGGGGACAGCGTGCGGCTGGTCCAGATAAGACTGGAAGAGGACTACGTCA
ATTTAGTATGAAAGGTCTTATCTCTTTCTCTGCCCCTATTATGCTTTCATCTAAATGCCTTT
CAATTTGTGAAAAGGTGGAAAGCAAAGGAAGGACAACTTACAATGAGGTTGCAGACGAGCTT
GTTGCTGAATTTGCACTTCCAAATAACGATGGAACATCCCCTGATCAGCAACAGTATGATGA
GAAAAACATAAGACGAAGAGTATATGATGCTTTAAACGTCCTCATGGCTATGGATATAATAT
CCAAGGATAAAAAGAAATTCAATGGAGAGGTCTTCCTCGGACAAGCTTAAGCGACATTGAA
GAATTAAAGAACGAACGACTCTCACTTAGGAACAGAATTGAGAAGAAAACTGCATATTCCCA
AGAACTGGAAGAACAAGTAATGAACATCATCGATACTCTCGGCTTATCTGCTTCCTGCCTTC
AGAATCTGATACAGAGAAATGAGCACTTATATAGCTCAGGAAATGCTCCCAGTGGCGGTGTT
GCTCTTCCTTTTATCCTTGTCCAGACTCGTCCTCACGCAACAGTAGAAGTGGAGATATCAGA
AGATATGCAGCTCGTGCATTTTGATTTCAACAGCACTCCATTTGAGCTCCACGACGACAATT
TTGTCCTCAAGACTATGAAGTTTTGTGATCAACCGCCGCAACAACCAAACGGTCGGAACAAC
AGCCAGCTGGTTTGTCACAATTTCACGCCAGAAAACCCTAACAAAGGCCCCAGCACAGGTCC
AACACCGCAGCTGGATATGTACGAGACTCATCTTCAATCGCAACAACATCAGCAGCATTCTC
AGCTACAAATCATTCCTATGCCTGAGACTAACAACGTTACTTCCAGCGCTGATACTGCTCCA
GTGAAATCCCGTCTCTTCCAGGGATAATGAACTCCAGCATGAAGCCGGAGAATTGAACCCA
GCTTTCTTGTACAAAGTGGTGATATCACAAGCCCGGGCGGTCTTCTAGGGATAACAGGGTAA
TTATATCCCTCTAGATCACAAGCCCGGGCGGTCTTCTACGATGATTGAGTAATAATGTGTCA
CGCATCACCATGGGTGGCAGTGTCAGTGTGAGCAATGACCTGAATGAACAATTGAAATGAAA
AGAAAAAAAGTACTCCATCTGTTCCAAATTAAAATTCATTTTAACCTTTTAATAGGTTTATA
CAATAATTGATATATGTTTTCTGTATATGTCTAATTTGTTATCATCCGGGCGGTCTTCTAGG
GATAACAGGGTAATTATATCCCTCTAGACAACACACAACAAATAAGAGAAAAAACAAATAAT
ATTAATTTGAGAATGAACAAAAGGACCATATCATTCATTAACTCTTCTCCATCCATTTCCAT
TTCACAGTTCGATAGCGAAAACCGAATAAAAAACACAGTAAATTACAAGCACAACAAATGGT
ACAAGAAAAACAGTTTTCCCAATGCCATAATACTCGAAC
```

FIGURE 2 (continued)

SEQ ID NO 9: Dpb motif 1

LDIXXDDA

SEQ ID NO 10: Dpb motif 2

KKKK/RR

SEQ ID NO 11: Dpb motif 3

AXGXDK

SEQ ID NO 12: maize Dp2 (CDS573)

GCTCCATTTTGCCCCCTCGCTCTTCACTTCCTCCGCTCCGCTTGTTGTCTCCTTCCCTAGGG
TTTGTCCAGCTCCGCGCTCAGCCTCGCTCGCTAGCTCCCGCTCTCCTCGATCCCGCGGCCCC
GATCAGCGCGATCTCCGCGCGGCCATGGTCTCCGGCGCGGCGCACAACCCGGGCGGGGGCGC
CGCCGCCCAGACCACCCAGCGCTCGCCGCCGCAGCTGGGGGCCCGGACGGCCCTCGCCACGC
CGCCGCCGGTCTCCGGGCGSGCCGCGCACTCCGCGTCTACTAGCGGCGGCACCGCTGGTTCA
CCACCGTCCAGCCGCAGCGAGCAGCACGCCCCGACGGTGCTGTCAAGGGTCCCGCCCTCGC
GCGCTGCGCCCGCAGCGGCGGCGGCGGCGTCCACGCCCGCCAGCGACAGCACGTTCCTCCGC
TTGAACTCGACATCAACSGCGACGACGCGCCGTCGTCGCAGGCTCCCACGAGCAAGAAGAAA
AGGAGAAGCACACGGGCAGTGGGTCCTGATAAAGGTAACCGGGGACTGCGCCAGTTTAGTAT
GAAAGTTTGTGAGAAAGTTGAAAGTAAAGGGAGAACAACATATAATGAGGTGGCAGATGAAC
TTGTTGCTGAGTTTACAGACCCCAATAATAATATTGAGGCACCAGACCCTGATAACCCTAAT
GCGCAACAATATGATGAAAAAAATATTCGACGAAGAGTTTATGATGCTTTAAATGTTCTGAT
GGCTATGGACATTATATCTAAAGATAAAAAGGAGATCCAGTGGAAGGGCTTGCCGCGGACTA
GTATAAGTGATATTGAAGAATTGAAGACTGAGCTTGTGGGACTGAAAGGTAGAATTGAGAAG
AAAAGTGTTTACTTACAGGAGCTACAAGATCAATATGTAGGTTTGCAAAACCTGATTCAACG
AAATGAGCAACTATATGGTTCAGGAAACACACCTTCTGGTGGAGTGGCTTTGCCATTCATCC
TAGTCCAGACCCGACCTCATGCAACCGTGGAAGTTGAGATATCAGAAGATATGCAGCTGGTT
CATTTTGACTTCAATAGCACTCCATTTGAGCTGCATGATGACTCATATGTCCTAAAAGAAAT
GCGGTTCTGTGGAAGAGAACAACATGATGGAACTCAAGAGTCGATATCAAATGGAGGTGAGA
GTTCAAACGTGTCAAATATTTATTGGCAACAAGCACAGCATATGGAGATGCCAAACAATGGC
ACAGTTAGGTTATCAAGCTCACCGCCTATTCCAGGGATATTAAAAGGGCGTGTGAAGCACGA
GCACTAGCGCTTCGGTTTTGGTTTCACTGGCGTTGTCGTCTGAGAGCAGTTTGTTTTATTAC
TTTTCTCCGTTGTGTAAAGCGCCTGTAAATTATTAGGCAAGGGGAGGGTAGTAGCTCTGAT
CTGATTTASCTCTGATTGGTAGAACGACGGGTGTAATTCTATATCCTTGATTCGGTTCTTTC
GGTATGGTTGAGAAAAGGGTTGACATGTAATTTGTRGRGCATTATAAAAACTAAAATTGTTG

FIGURE 2 (continued)

SEQ ID NO 13: maize DP2 protein prediction (CDS573)

MVSGAAHNPGGGAAAQTTQRSPPQLGARTALATPPPVSGXAAHSASTSGGTAGSPPSSRSEQ
HAPDGAVKGPALARCARSGGGGVHARQRQHVPPLELDINXDDAPSSQAPTSKKKRRSTRAVG
PDKGNRGLRQFSMKVCEKVESKGRTTYNEVADELVAEFTDPNNNIEAPDPDNPNAQQYDEKN
IRRRVYDALNVLMAMDIISKDKKEIQWKGLPRTSISDIEELKTELVGLKGRIEKKSVYLQEL
QDQYVGLQNLIQRNEQLYGSGNTPSGGVALPFILVQTRPHATVEVEISEDMQLVHFDFNSTP
FELHDDSYVLKEMRFCGREQHDGTQESISNGGESSNVSNIYWQQAQHMEMPNNGTVRLSSSP
PIPGILKGRVKHEH

SEQ ID NO 14: rice DP2 (CDS574)

CCCTCCATCCATCCATCCCCCACCTCCGCTCTCTAGGGTTTCTCCCCCGCCTCCTCCCCCC
AATCTCGCCGCCGCGATGGTCTCCGGCGCGGCGCATTCGGCCTCCACCAGTGGCGGCGGCGG
GGGGAGCGAGGGCTCCCCCACCGGCCGCGCCGCGCCGGGCATGCAGGGCGGCGGCAGCGCCG
CCACGCCCGCCGCCTCGGCCTCCGCGTCCACGCCGGCCAGCGAGACCACCGTCGCCCGCCGC
CTCGACGGCCTCGACATCCAGGGCGACGACGCGCCCGTCGCAGCCCGCCACGAGCAAGAA
GAAAAAAGGGGGACACGTGCAACGGGCCCTGACAAGGGTGGCCGTGGATTGCGCCAATTTA
GTATGAAAGTTTGTGAGAAAGTTGAAAGCAAAGGGAGAACAACCTACAACGAGGTGGCAGAT
GAGCTTGTAGCTGAGTTTGCAGACCCCAACAATAATTTTGCATCACCTGATCCTGACAACCC
TAACACACCACAATTTGATGAGAAAAATATACGACGAAGGGTTTATGATGCATTGAATGTCC
TGATGGCTATGGATATTATATCTAAGGATAAAAAGGAAATTCAGTGGAAGGGCTTGCCTCGG
ACAAGTATGAGCGATGTTGAAGAATTGAAGGTTNAGATCATCGGACTGAAAGGTAGGATCGA
CAAGAAAAATGCATATTTGCAGGAGTTAGAAGATCAATATGTAGGTTTGCAAAACCTGATTC
AACGAAACGAGCAGCTTTATGGTTCAGGAAATGCTCCTTCAGGAGGAGTGGCATTGCCATTT
ATCCTAGTTCAGACACGTCCTCATGCTACAGTAGAAGTGGAGATATCAGAAGATATGCAGCT
GGTGCATTTTGATTTCAATAGCACTCCATTTGAACTGCATGACGATTCCTTTGTACTGAAAG
CATTGGGGTTCTCTGGCAAAGAACCAGATGATACGCAAGCCTGGGTTGGAAATGGAGGTGAG
TGCTCAACCACACCTATCTATCATCAATCACCCCAAGTTGCGAGGCCAAACGGAGTTAGACT
ACCAACATCGCCCCCTATTCCCGGTATACTTAAAGGGCGTGTCAAGCATGAACATTAGGGGT
TACTATGATTTGTTGATGGTGTGAGGTACTTGGTTTATTTGTTACTCCCCAATTTTCCCTTT
TTGTAACTTTACATGTAGAAAGAGCCTGTACATTAGATCAATGGGGGAAAAATGGCGGGTCT
AGTTTAGTTTCACTGGTAGAAGATCGATGGGCATGTTGACAAACCATATGCCTAACTTAACT
TGTA

FIGURE 2 (continued)

SEQ ID NO 15: rice DP2 (CDS574)

MVSGAAHSASTSGGGGGSEGSPTGRAAPGMQGGGSAATPAASASASTPASETTVARRLDGLD
IQGDDAPSSQPATSKKKKRGTRATGPDKGGRGLRQFSMKVCEKVESKGRTTYNEVADELVAE
FADPNNNFASPDPDNPNTPQFDEKNIRRRVYDALNVLMAMDIISKDKKEIQWKGLPRTSMSD
VEELKVXIIGLKGRIDKKNAYLQELEDQYVGLQNLIQRNEQLYGSGNAPSGGVALPFILVQT
RPHATVEVEISEDMQLVHFDFNSTPFELHDDSFVLKALGFSGKEPDDTQAWVGNGGECSTTP
IYHQSPQVARPNGVRLPTSPPIPGI
LKGRVKHEH

SEQ ID NO 16: Oryza sativa (japonica cultivar-group) E2F dimerization factor mRNA (AY224589.1)

ATGGTCTCCGGCGTCGCCCACCGCCCGGACGACGACGGCGGGCGCGCCGCCTCGACGTTCCA
GCGCCCGCCGCAGCCGGCCGGCGCGCGGCCGTCCCTGGCCACGCCGCCGCCCTCGGGCGGAG
CGCAATCCGCTTCGACGAGCGGCGGGAGCGCGGGCTCCCCGTCCAGCCGCAGCGAGCAGCAT
GTCCCCGCAGCCGCAGGCATGGCGGCGGGGCGGCGGCGGCCTCTACTCCGATTAGTGAGAA
TACCTTCCTCCGCCTCAACGACCTTGACATCCACGGCGACGATGCGCCTTCCTCACAGGCTC
CAACGAGCAAGAAGAAGAAGAGAGGAGCACGAGCAGTTGGTCCTGACAAAGGTGGCAGGGGG
CTGCGCCAGTTTAGTATGAAGGTTTGTGAGAAAGTTGAAAGTAAAGGGAGAACAACATACAA
CGAGGTGGCAGATGAACTTGTTGCCGAATTTGCAGATCCCAATAACAGCATTTTGCCACCAG
ATCCGGATAATCCCAATGCACAACAATATGACGAGAAAATATACGGAGAAGGGTTTATGAT
GCTCTGAATGTTCTGATGGCTATGGAGATTATATCTAAAGATAAAAAGGAAATTCAGTGGAA
GGGGTTGCCTCGAACCAGTATAAATGATATTGAAGATTTGCAGACGGAACTTGTAGGACTGA
AAAGTAGGATTGAGAAGAAAAATACATATTTGCAGGAGCTGCAAGACCAATTTGTAGGTATG
CAAAAGTTGATACAAAGAAATGAACAGCTATATGGTTCAGGAAACATTCCCTCGGGTGGAGT
TGCATTACCATTTATCCTTGTTCAGACACGGCCTCATGCAACTGTGGAAGTTGAAATATCAG
AAGATATGCAACTTGTACATTTTGACTTTAATAGCACACCATTTGAGTTGCATGATGACTCA
TTTGTACTGAAAGCAATGAGTTCTTGTGGAGAAGAACAAATCGACGGTATTCATGATCTAAT
TTCAAATGGAGGTGAGAGCTCAAGCATGCCAAATATTTATAGGCAGCAAGTGCAGCAACCTG
CAAGATCAACTAATGGTACAGCTAGATTGCCAAGCTCACCCCCTATTCCAGGAATACTGAAA
GGGCGAGTGAAGCACGAGCATTAG

FIGURE 2 (continued)

SEQ ID NO 17: Oryza sativa (japonica cultivar-group) E2F dimerization factor Dp-like (AAO72709.1)

MVSGVAHRPDDDGGRAASTFQRPPQPAGARPSLATPPPSGGAQSASTSGGSAGSPSSRSEQH
VPAAAGMAAGAAAASTPISENTFLRLNDLDIHGDDAPSSQAPTSKKKKRGARAVGPDKGGRG
LRQFSMKVCEKVESKGRTTYNEVADELVAEFADPNNSILPPDPDNPNAQQYDEKNIRRRVYD
ALNVLMAMEIISKDKKEIQWKGLPRTSINDIEDLQTELVGLKSRIEKKNTYLQELQDQFVGM
QKLIQRNEQLYGSGNIPSGGVALPFILVQTRPHATVEVEISEDMQLVHFDFNSTPFELHDDS
FVLKAMSSCGEEQIDGIHDLISNGGESSSMPNIYRQQVQQPARSTNGTARLPSSPPIPGILK
GRVKHEH

SEQ ID NO 18: Oryza sativa (japonica cultivar-group) DP TF mRNA, complete cds (AY224551.1)

ATGGTCTCCGGCGCGGCGCATTCGGCCTCCACCAGTGGCGGCGGCGGGGGGAGCGAGGGCTC
CCCCACCGGCCGCGCCGCGCCGGGCATGCAGGGCGGCGGCAGCGCCGCCACGCCCGCCGCCT
CGGCCTCCGCGTCCACGCCGGCCAGCGAGACCACCGTCGCCCGCCGCCTCGACGGCCTCGAC
ATCCAGGGCGACGACGCGCCCTCGTCGCAGCCCGCCACGAGCAAGAAGAAAAAAGGGGCC
TGGAACACGTGCAACGGGCCCTGACAAGGGTGGCCGTGGATTGCGCCAATTTAGTATGAAAG
TTTGTGAGAAAGTTGAAAGCAAAGGGAGAACAACCTACAACGAGGTGGCAGATGAGCTTGTA
GCTGAGTTTGCAGACCCCAACAATAATTTTGCATCACCTGATCCTGACAACCCTAACACACC
ACAATTTGATGAGAAAAATATACGACGAAGGGTTTATGATGCATTGAATGTCCTGATGGCTA
TGGATATTATATCTAAGGATAAAAAGGAAATTCAGTGGAAGGGCTTGCCTCGGACAAGTATG
AGCGATGTTGAAGAATTGAAGACAGAGATCATCGGACTGAAAGGTAGGATCGACAAGAAAAA
TGCATATTTGCAGGAGTTAGAAGATCAATTTGTAGGTCTTCAAAACTTGGCACAGCGAAACG
AGCAGCTTTATGGTTCAGGAAATGCTCCTTCAGGAGGAGTGGCATTGCCATTTATATTGGTG
CAGACACGTCCTCATGCTACAGTAGAAGTGGAGATATCAGAAGATATGCAGCTGGTGCATTT
TGATTTCAATAGCACTCCATTTGAACTGCATGACGATTCCTTTGTACTGAAAGCATTGGGGT
TCTCTGGCAAAGAACCAGATGATACGCAAGCCTGGGTTGGAAATGGAGGTGAGTGCTCAACC
ACACCTATCTATCATCAATCACCCCAAGTTGCGAGGCCAAACGGAGTTAGACTACCAACATC
GCCCCCTATTCCGGTATACTTAAAGGGCGTGTCAAGCATGAACATTAG

SEQ ID NO 19: Oryza sativa (japonica cultivar-group) DP TF Dpb-like (AAO72671.1)

MVSGAAHSASTSGGGGGSEGSPTGRAAPGMQGGGSAATPAASASASTPASETTVARRLDGLD
IQGDDAPSSQPATSKKKKRGPGTRATGPDKGGRGLRQFSMKVCEKVESKGRTTYNEVADELV
AEFADPNNNFASPDPDNPNTPQFDEKNIRRRVYDALNVLMAMDIISKDKKEIQWKGLPRTSM
SDVEELKTEIIGLKGRIDKKNAYLQELEDQFVGLQNLAQRNEQLYGSGNAPSGGVALPFILV
QTRPHATVEVEISEDMQLVHFDFNSTPFELHDDSFVLKALGFSGKEPDDTQAWVGNGGECST
TPIYHQSPQVARPNGVRLPTSPPIPGILKGRVKHEH

Figure 2 (continued)

SEQ ID NO 20: Oryza sativa (japonica cultivar-group) putative DP-like protein (OSJNBa0046P18.3), mRNA (NM_196694.1)

```
ATGGTCTCCGGCGCGGCGCATTCGGCCTCCACCAGTGGCGGCGGCGGGGGGAGCGAGGGCTC
CCCCACCGGCCGCGCCGCGCCGGGCATGCAGGGCGGCGGCAGCGCCGCCACGCCCGCCGCCT
CGGCCTCCGCGTCCACGCCGGCCAGCGAGACCACCGTCGCCCGCCGCCTCGACGGCCTCGAC
ATCCAGGGCGACGACGCGCCCTCGTCGCAGCCCGCCACGAGCAAGAAGAAAAAAGGGGGCC
TGGAACACGTGCAACGGGCCCTGACAAGGGTGGCCGTGGATTGCGCCAATTTAGTATGAAAG
TTTGTGAGAAAGTTGAAAGCAAAGGGAGAACAACCTACAACGAGGTGGCAGATGAGCTTGTA
GCTGAGTTTGCAGACCCCAACAATAATTTTGCATCACCTGATCCTGACAACCCTAACACACC
ACAATTTGATGAGAAAAATATACGACGAAGGGTTTATGATGCATTGAATGTCCTGATGGCTA
TGGATATTATATCTAAGGATAAAAAGGAAATTCAGTGGAAGGGCTTGCCTCGGACAAGTATG
AGCGATGTTGAAGAATTGAAGACAGAGATCATCGGACTGAAAGGTAGGATCGACAAGAAAAA
TGCATATTTGCAGGAGTTAGAAGATCAATTTGTAGGTCTTCAAAACTTGGCACAGCGAAACG
AGCAGCTTTATGGTTCAGGAAATGCTCCTTCAGGAGGAGTGGCATTGCCATTTATATTGGTG
CAGCATTGGGGTTCTCTGGCAAAGAACCAGATGATACGCAAGCCTGGGTTGGAAATGGAGGT
GAGTGCTCAACCACACCTATCTATCATCAATCACCCCAAGTTGCGAGGCCAAACGGAGTTAG
ACTACCAACATCGCCCCCTATTCCCGGTATACTTAAAGGGCGTGTCAAGCATGAACATTAGG
GGTTACTATGATTTGTTGATGGTGTGA
```

SEQ ID NO 21: Oryza sativa (japonica cultivar-group) putative DP-like protein (OSJNBa0046P18.3), protein (NP_921676.1) spliced

```
MVSGAAHSASTSGGGGGSEGSPTGRAAPGMQGGGSAATPAASASASTPASETTVARRLDGLD
IQGDDAPSSQPATSKKKKRGPGTRATGPDKGGRGLRQFSMKVCEKVESKGRTTYNEVADELV
AEFADPNNNFASPDPDNPNTPQFDEKNIRRRVYDALNVLMAMDIISKDKKEIQWKGLPRTSM
SDVEELKTEIIGLKGRIDKKNAYLQELEDQFVGLQNLAQRNEQLYGSGNAPSGGVALPFILV
QHWGSLAKNQMIRKPGLEMEVSAQPHLSIINHPKLRGQTELDYQHRPLFPVYLKGVSSMNIR
GYYDLLMV
```

SEQ ID NO 22: Populus tremula x Populus tremuloides DP1 (DP1) mRNA, complete cds (AY307373.1)

CAAATCCAAACAACACGCGTCTCTCTTCTGTTGCTTTATCATCAACCTAACCCAAACCGCCA
CTCCTCTTCTCTTGTATAACTGACCGTTCCCGTCACTCTCCCTTTTCCTTTTCGTTTATTAA
TTCGGTATAATTTCCCATCTTTTATATCTTAATGGTCGCTGGTGGGGCCCACCTGGAAGATG
GAGACAGGCACCCTTCGTCGGCCTCCAGAAGAGGAGGAGGAGGAGGAGCCACCACGGGCTCC
TGGGTGTCTGGCCAATCGGTGTCAACTAGCGGCAGCGTGGGGTCTCCATCCAGCAGGAGCGA
GCATGCCATGGCCACTCCCGCTAGTGACAGCACTTTCTTAAGGTTGAACCATCTCGACATTC
ACGCCGATGATGCCGCCACTCAAGATGCCGCCGCTAATAAGAAGAAAAAGAGAGGTCAACGG
GCTGTTGGAGCTGATAAGAGTGGTAGAGGACTTCGTCAATTTAGCATCAAAGTTTGTGAAAA
GGTGGAATCCAAAGGAACAACTACTTACAACGAGGTAGCAGATGAACTTGTCGCAGAGTTTG
CTGACCCAAGCAATAGTGTTTCCACCCCAGATCAGCAACAATATGACGAGAAAAACATACGG
CGGAGGGTATATGATGCTCTGAATGTACTCATGGCATTAGATATTATATCTAAGGATAAAAA
GGAAATACAGTGGAAAGGTCTTCCCCGAACAAGCCTAAGTGATATTGAAGAATTGAAGGTTG
AGCGTCTTGGATTGAGAAATAGATTCGAAAAGAAAGCTGCCTATTTGCAAGAACTGGAGGAA
CAATTTGTAGGTCTTCAGAACCTGATACAGCGAAATGAACAACTGTACAGCTCAGGAAATGC
TCCTAGTGGTGGTGTGTCGTTGCCTTTTATTCTGGTGCAGACACGCCCTCATGCAACTGTTG
AAGTGGAGATATCAGAAGATATGCAGCTGGTTCACTTTGATTTTAATAGCACTCCCTTCGAG
CTCCATGACGATAATTACGTTCTCAAGGCAATGAAATTTTGTGAGAGACCTCAGAGCGATGG
TATGGCACCCAATCCACCTGCTGATGGAGGTGAAGGTTCTAGCATGTCCAGCATGTATCAAC
CACAAATCCTTGCTTCCCCAAGTACAAACACCCCAGTTAGGCATCCTACTTCGCCGCCTCTT
CCTGGAATCATAAAAGCACGTGTTAAGAATGAGCATTGAGTCATGCACGATCATCTGAACCA
TGGGCAATCATGTCAGCTGTGTCTGTATATTGTGTAAAGTAGTTTGCTGTAGATGGTGCCTC
CCTATAATTATCCCCGTTCACAGTTTGCCCTTGTTAGGAGGAACTGAGATGACAAGCAGATC
GGCCCTTATGCTTTGAGACTTCCATGGAAACACTTGGTTCTATCTGGTTCTCAGCTTTAGAT
CCATTATTCGCTTCTGTAACTGTTTAACCATTTTTTTTCCAGTTATTTTTTCCCATTGTAGC
AAAAATTAAGTTTAGATTGTATTAGGCTACATAGGATTGTCCAGCCTTACTCAGAATGATAG
AATGAATTAATTCAATTCTTCAAGAATTTGGTGTTATAAAAAAAAAAAAAAAAAAAAAAAAA
AAAAAAAAAAAAAAAAAAAAAAAAAAAA

SEQ ID NO 23: Populus tremula x Populus tremuloides DP1 (AAP73785.1)

MVAGGAHLEDGDRHPSSASRRGGGGGATTGSWVSGQSVSTSGSVGSPSSRSEHAMATPASDS
TFLRLNHLDIHADDAATQDAAANKKKRGQRAVGADKSGRGLRQFSIKVCEKVESKGTTTYN
EVADELVAEFADPSNSVSTPDQQQYDEKNIRRRVYDALNVLMALDIISKDKKEIQWKGLPRT
SLSDIEELKVERLGLRNRFEKKAAYLQELEEQFVGLQNLIQRNEQLYSSGNAPSGGVSLPFI
LVQTRPHATVEVEISEDMQLVHFDFNSTPFELHDDNYVLKAMKFCERPQSDGMAPNPPADGG
EGSSMSSMYQPQILASPSTNTPVRHPTSPPLPGIIKARVKNEH

FIGURE 2 (continued)

```
cds573Dp2maize              MVSGAAHNPG--GGAAAQTTQRSPPQLGARTALATPPPVSG-AAHSASTS   47  SEQ ID NO: 24
cornDP2reconstructed        MVSGAAHNPG--GGAAAQTTQRSPPQLGARTALATPPPVSGXAAHSASTS   48  SEQ ID NO: 13
AAO72709.1riceE2F_Dpblike_  MVSGVAHRPDDDGGRAASTFQRPPQPAGARPSLATPPPSGG--AQSASTS   48  SEQ ID NO: 17
AY224551oryzaDp1alike       MVSGAAHSASTSGGGGGSE--------GSPTCRAAP----------GMQG   32  SEQ ID NO: 19
AAO72671.1Dpblikerice       MVSGAAHSASTSGGGGGSE--------GSPTGRAAP----------GMQG   32  SEQ ID NO: 19
cds574Dp2rice               MVSGAAHSASTSGGGGGSE--------GSPTGRAAP----------GMQG   32  SEQ ID NO: 25
riceDP2reconstructed        MVSGAAHSASTSGGGGGSE--------GSPTGRAAP----------GMQG   32  SEQ ID NO: 15
NP_921676.1Dpblikericeslpicedf MVSGAAHSASTSGGGGGSE-----GSPTGRAAP----------GMQG   32  SEQ ID NO: 21
cds0006arabidopsisDpb       MTTTGSNSNHN--HHESNNNNNNPSTRSWGTAVSGQ-----------SVST  38  SEQ ID NO: 02
AY307373Dp1apopulus         MVAGGAHLEDGDRHPSSASRRGGGGGATTGSWVSGQ-----------SVST  40  SEQ ID NO: 23
cds0007arabidopsisDpa       --------------------------------------------MSME    4  SEQ ID NO: 26
AY224529oryzaDPlike         MAPPCGDAAAAASAAPGLAN--------------------------LLI   23  SEQ ID NO: 27
AAO72649.1Dpalikericespliced MAPPCGDAAAAASAAPGLAN-------------------------LLI   23  SEQ ID NO: 27
NP_916921.1Dpalikerice      MAPPCGDAAAAASAAPGLAN--------------------------LLI   23  SEQ ID NO: 28
BAB90030.1DpalikericeGenomic MAPPCGDAAAAASAAPGLAN-------------------------LLI   23  SEQ ID NO: 28
AJ271917triticumDp1alike    MAPPRGGAAAAATAALDLTG--------------------------VHI   23  SEQ ID NO: 29

Cont.
cds573Dp2maize              GGTAGSPPSSRSEQHAP-------DGAVKGPALARCARSGGGGVHARQRQ  90  SEQ ID NO: 24
cornDP2reconstructed        GGTAGSPPSSRSEQHAP-------DGAVKGPALARCARSGGGGVHARQRQ  91  SEQ ID NO: 13
AAO72709.1riceE2F_Dpblike_  GGSAGSP-SSRSEQHVP-------AAAGMAAGAAAASTPISENTPLRLN-  89  SEQ ID NO: 17
AY224551oryzaDp1alike       GGSAATPAASAS--------------ASTPASETTVARRLDG--------  60  SEQ ID NO: 19
AAO72671.1Dpblikerice       GGSAATPAASAS--------------ASTPASETTVARRLDG--------  60  SEQ ID NO: 19
cds574Dp2rice               GGSAATPAASAS--------------ASTPASETTVARRLDG--------  60  SEQ ID NO: 25
riceDP2reconstructed        GGSAATPAASAS--------------ASTPASETTVARRLDG--------  60  SEQ ID NO: 15
NP_921676.1Dpblikericeslpicedf GGSAATPAASAS-----------ASTPASETTVARRLDG--------  60  SEQ ID NO: 21
cds0006arabidopsisDpb       SGSMGSPSSRSEQT----------ITVVTSTSDTTFQRLNN---------  69  SEQ ID NO: 02
AY307373Dp1apopulus         SGSVGSPSSRSE------------HAMATPASDSTFLRLNH---------  69  SEQ ID NO: 23
cds0007arabidopsisDpa       MELFVTPEKQRQ-------------HPSVSVEKTPVRRKLIV--------  33  SEQ ID NO: 26
AY224529oryzaDPlike         REGAGLPSRPERYPPFRPCTSDSFAPISREGDDIPPQKKSVS--------  65  SEQ ID NO: 27
AAO72649.1Dpalikericespliced REGAGLPSRPERYPPFRPCTSDSFAPISREGDDIPPQKKSVS-------  65  SEQ ID NO: 27
NP_916921.1Dpalikerice      REGAGLPSRPE--------------REGDDIPPQKKSVS---------   48  SEQ ID NO: 28
BAB90030.1DpalikericeGenomic REGAGLPSRPE-------------REGDDIPPQKKSVS----------   48  SEQ ID NO: 28
AJ271917triticumDp1alike    LEASSVPPLPE---------------------------------------  34  SEQ ID NO: 29

DPb motif 1   DPb motif 2  DPb motif 3              Cont.
cds573Dp2maize              HVPPLELDIN-DDAPSSQAPTSKKKRR--STRAVGPDKGNRGLRQFSMKV  137  SEQ ID NO: 24
cornDP2reconstructed        HVPPLELDINXDDAPSSQAPTSKKKRR--STRAVGPDKGNRGLRQFSMKV  139  SEQ ID NO: 13
AAO72709.1riceE2F_Dpblike_  -----DLDIHGDDAPSSQAPTSKKKKR--GARAVGPDKGGRGLRQFSMKV  132  SEQ ID NO: 17
AY224551oryzaDp1alike       -----LDIQGDDAPSSQPATSKKKKRGPGTRATGPDKGGRGLRQFSMKV  104  SEQ ID NO: 19
AAO72671.1Dpblikerice       -----LDIQGDDAPSSQPATSKKKKRGPGTRATGPDKGGRGLRQFSMKV  104  SEQ ID NO: 19
cds574Dp2rice               -----LDIQGDDAPSSQPATSKKKKR--GTRATGPDKGGRGLRQFSMKV  102  SEQ ID NO: 25
riceDP2reconstructed        -----LDIQGDDAPSSQPATSKKKKR--GTRATGPDKGGRGLRQFSMKV  102  SEQ ID NO: 15
NP_921676.1Dpblikericeslpicedf -LDIQGDDAPSSQPATSKKKKRGPGTRATGPDKGGRGLRQFSMKV  104  SEQ ID NO: 21
cds0006arabidopsisDpb       -----LDIQGDDASQGASGVKKKKR--GQRAAGPDKTGRGLRQFSMKV  111  SEQ ID NO: 02
AY307373Dp1apopulus         -----LDIHADDARTQDAAANKKKKR--GQRAVGADKSGRGLRQFSIKV  111  SEQ ID NO: 23
cds0007arabidopsisDpa       ------------DDDSEIGSEKKGQSR---------TSGGGLRQFSVMV   61  SEQ ID NO: 26
AY224529oryzaDPlike         -----LRSGGGGNAAERE-EGGANRNGKKEKTGAQRITGWGLREFSKIV  108  SEQ ID NO: 27
AAO72649.1Dpalikericespliced -----LRSGGGGNAAERE-EGGANRNGKKEKTGAQRITGWGLREFSKIV 108  SEQ ID NO: 27
NP_916921.1Dpalikerice      -----LRSGGGGNAAERE-EGGANRNGKKEKTGAQRITGWGL------L   85  SEQ ID NO: 28
BAB90030.1DpalikericeGenomic -----LRSGGGGNAAERE-EGGANRNGKKEKTGAQRITGWGL------L   85  SEQ ID NO: 28
AJ271917triticumDp1alike    ---------RGGNAVQRKGAVDPDKDRKKEKAAAPRITGWGLREYSKIV   74  SEQ ID NO: 29

DNA binding domain ▼
```

FIGURE 3

```
                                                ┌──── DP conserved region                                          Cont.
cds573Dp2maize                                  ¦CEKVESKGRTTYNE----------------VADELVAEFTDPNNNIEA 169              SEQ ID NO: 24
cornDP2reconstructed                            ¦CEKVESKGRTTYNE----------------VADELVAEFTDPNNNIEA 171              SEQ ID NO: 13
AAO72709.1riceE2F_Dpblike_                      ¦CEKVESKGRTTYNE----------------VADELVAEFADPNNSILP 164              SEQ ID NO: 17
AY224551oryzaDp1alike                           ¦CEKVESKGRTTYNE----------------VADELVAEFADPNNNFAS 136              SEQ ID NO: 19
AAO72671.1Dpblikerice                           ¦CEKVESKGRTTYNE----------------VADELVAEFADPNNNFAS 136              SEQ ID NO: 19
cds574Dp2rice                                   ¦CEKVESKGRTTYNE----------------VADELVAEFADPNNNFAS 134              SEQ ID NO: 25
riceDP2reconstructed                            ¦CEKVESKGRTTYNE----------------VADELVAEFADPNNNFAS 134              SEQ ID NO: 15
NP_921676.1DpblikericeslpicedF                  ¦CEKVESKGRTTYNE----------------VADELVAEFADPNNNFAS 136              SEQ ID NO: 21
cds0006arabidopsisDpb                           ¦CEKVESKGRTTYNE----------------VADELVAEFALPNNDGTS 143 ▶            SEQ ID NO: 02
AY307373Dp1apopulus                             ¦CEKVESKGTTTYNE----------------VADELVAEFADPSNSVST 143 ▶            SEQ ID NO: 23
cds0007arabidopsisDpa                           ¦CQKLEAKKITTYKE----------------VADEIISDFATIKQNAEK  93              SEQ ID NO: 26
AY224529oryzaDPlike                             ¦SKKVEAKGRTTYNE----------------VADEIFAELKSITQN---  137             SEQ ID NO: 27
AAO72649.1Dpalikericespliced                    ¦SKKVEAKGRTTYNE----------------VADEIFAELKSITQN---  137             SEQ ID NO: 27
NP_916921.1Dpalikerice                          ¦SKKVEAKGRTTYNEIMVQTSNDEVYTSSGELIVADEIFAELKSITQN-- 132             SEQ ID NO: 28
BAB90030.1DpalikericeGenomic                    ¦SKKVEAKGRTTYNEIMVQTSNDEVYTSSGELIVADEIFAELKSITQN-- 132             SEQ ID NO: 28
AJ271917triticumDp1alike                        ¦CEKVEAKGRTTYNE----------------VADEIYSELKSMAHI---  103             SEQ ID NO: 29
                                                ¦ .:*:*:*  ***:*                 ****: :::       :
                                                └────

Cont.
cds573Dp2maize                                   PDPDNPNAQQYDEKNIRRRVYDALNVLMAMDIISKDKKEIQWKGLPRTSI 219             SEQ ID NO: 24
cornDP2reconstructed                             PDPDNPNAQQYDEKNIRRRVYDALNVLMAMDIISKDKKEIQWKGLPRTSI 221             SEQ ID NO: 13
AAO72709.1riceE2F_Dpblike_                       PDPDNPNAQQYDEKNIRRRVYDALNVLMAMEIISKDKKEIQWKGLPRTSI 214             SEQ ID NO: 17
AY224551oryzaDp1alike                            PDPDNPNTPQFDEKNIRRRVYDALNVLMAMDIISKDKKEIQWKGLPRTSM 186             SEQ ID NO: 19
AAO72671.1Dpblikerice                            PDPDNPNTPQFDEKNIRRRVYDALNVLMAMDIISKDKKEIQWKGLPRTSM 186             SEQ ID NO: 19
cds574Dp2rice                                    PDPDNPNTPQFDEKNIRRRVYDALNVLMAMDIISKDKKEIQWKGLPRTSM 184             SEQ ID NO: 25
riceDP2reconstructed                             PDPDNPNTPQFDEKNIRRRVYDALNVLMAMDIISKDKKEIQWKGLPRTSM 184             SEQ ID NO: 15
NP_921676.1DpblikericeslpicedF                   PDPDNPNTPQFDEKNIRRRVYDALNVLMAMDIISKDKKEIQWKGLPRTSM 186             SEQ ID NO: 21
cds0006arabidopsisDpb                            PD-----QQQYDEKNIRRRVYDALNVLMAMDIISKDKKEIQWKGLPRTSL 188 ▶           SEQ ID NO: 02
AY307373Dp1apopulus                              PD-----QQQYDEKNIRRRVYDALNVLMALDIISKDKKEIQWKGLPRTSL 188             SEQ ID NO: 23
cds0007arabidopsisDpa                            PLN----ENEYNEKNIRRRVYDALNVFMALDIIARDKKEIRWKGLPITCK 139             SEQ ID NO: 26
AY224529oryzaDPlike                              -------GLEFDEKNIRRRVYDAFNVLIAIRVIAKDKKEIKWMGLTNYRY 180             SEQ ID NO: 27
AAO72649.1Dpalikericespliced                     -------GLEFDEKNIRRRVYDAFNVLIAIRVIAKDKKEIKWMGLTNYRY 180             SEQ ID NO: 27
NP_916921.1Dpalikerice                           -------GLEFDEKNIRRRVYDAFNVLIAIRVIAKDKKEIKWMGLTNYRY 175             SEQ ID NO: 28
BAB90030.1DpalikericeGenomic                     -------GLEFDEKNIRRRVYDAFNVLIAIRVIAKDKKEIKWMGLTNYRY 175             SEQ ID NO: 28
AJ271917triticumDp1alike                         -------GQGFDEKNIRRRVYDAFNVLIALRVIAKEKKEIRWMGLSNYRY 146             SEQ ID NO: 29
                                                        ::**********:**:::*: :*::*****:* **.

Cont.
cds573Dp2maize                                   SDIEELKTELVGLKGRIEKKSVYLQELQDQYVGLQNLIQRNEQLYGSGNT 269             SEQ ID NO: 24
cornDP2reconstructed                             SDIEELKTELVGLKGRIEKKSVYLQELQDQYVGLQNLIQRNEQLYGSGNT 271             SEQ ID NO: 13
AAO72709.1riceE2F_Dpblike_                       NDIEDLQTELVGLKSRIEKKNTYLQELQDQYVGMQKLIQRNEQLYGSGNI 264             SEQ ID NO: 17
AY224551oryzaDp1alike                            SDVEELKTEIIGLKGRIDKKNAYLQELEDQYVGLQNLAQRNEQLYGSGNA 236             SEQ ID NO: 19
AAO72671.1Dpblikerice                            SDVEELKTEIIGLKGRIDKKNAYLQELEDQYVGLQNLIQRNEQLYGSGNA 236             SEQ ID NO: 19
cds574Dp2rice                                    SDVEELKV-IIGLKGRIDKKNAYLQELEDQYVGLQNLIQRNEQLYGSGNA 233             SEQ ID NO: 25
riceDP2reconstructed                             SDVEELKVXIIGLKGRIDKKNAYLQELFDQYVGLQNLIQRNEQLYGSGNA 234             SEQ ID NO: 15
NP_921676.1DpblikericeslpicedF                   SDVEELKTEIIGLKGRIDKKNAYLQELEDQYVGLQNLAQRNEQLYGSGNA 236             SEQ ID NO: 21
cds0006arabidopsisDpb                       ◀───  SDIEELKNERLSLRNRIEKKTAYSQELEFQXVGLQNLIQRNEHLYSSGNA 238 ▶         SEQ ID NO: 02
AY307373Dp1apopulus                              SDIEELKVERLGLRNRFEKKAAYLQELEEQFVGLQNLIQRNEQLYSSGNA 238             SEQ ID NO: 23
cds0007arabidopsisDpa                            KDVEEVKMDRNKVMSSVQKKAAFLXELREKVSSLESLMSRNQEMVVKTQG 189             SEQ ID NO: 26
AY224529oryzaDPlike                              EKIQKLEEVHKELITRIKNKKKLLQEIEKQFDDLQNITLRNQASQRPAES 230             SEQ ID NO: 27
AAO72649.1Dpalikericespliced                     EKIQKLEEVHKELITRIKNKKKLLQEIEKQFDDLQNITLRNQASQRPAES 230             SEQ ID NO: 27
NP_916921.1Dpalikerice                           EKIQKLEEVHKELITRIKNKKKLLQEIEKQFDDLQNITLRNQASQRPAES 225             SEQ ID NO: 28
BAB90030.1DpalikericeGenomic                     EKIQKLEEVHKELITRIKNKKKLLQEIEKQFDDLQNITLRNQASQRPAES 225             SEQ ID NO: 28
AJ271917triticumDp1alike                         EKIKKLEEVRKELVNKIRNKKALLQEIEKQFDDLQNIKLRNQTLESSAEN 196             SEQ ID NO: 29
                                                 ..::::      :    .:*    :*:..:  .:::  **:         :

Dimerization domain ▼
```

FIGURE 3 (continued)

```
                                                                                                              Cont.
cds573Dp2maize              PSGGVALPFILVQTRPHATVEVEISEDMQLVHFDFNSTPPFELHDDSYVLK 319  SEQ ID NO: 24
cornDP2reconstructed        PSGGVALPFILVQTRPHATVEVEISEDMQLVHFDFNSTPPFELHDDSYVLK 321  SEQ ID NO: 13
AAO72709.1riceE2F_Dpblike_  PSGGVALPFILVQTRPHATVEVEISEDMQLVHFDFNSTPPFELHDDSFVLK 314  SEQ ID NO: 17
AY224551oryzaDplalike       PSGGVALPFILVQTRPHATVEVEISEDMQLVHFDFNSTPPFELHDDSFVLK 286  SEQ ID NO: 19
AAO72671.1Dpblikerice       PSGGVALPFILVQTRPHATVEVEISEDMQLVHFDFNSTPPFELHDDSFVLK 286  SEQ ID NO: 19
cds574Dp2rice               PSGGVALPFILVQTRPHATVEVEISEDMQLVHFDFNSTPPFELHDDSFVLK 283  SEQ ID NO: 25
riceDP2reconstructed        PSGGVALPFILVQTRPHATVEVEISEDMQLVHFDFNSTPPFELHDDSFVLK 284  SEQ ID NO: 15
NP_921676.1Dpblikericeslpicedf PSGGVALPFILVQHWGSLAKNQMIRK--PGLEMEVSAQPHLS-----IIN 279  SEQ ID NO: 21
cds0006arabidopsisDpb       PSGGVALPFILVQTRPHATVEVEISEDMQLVHFDFNSTPPFELHDDNFVLK 288  SEQ ID NO: 02
AY307373Dplapopulus         PSGGVSLPFILVQTRPHATVEVEISEDMQLVHFDFNSTPFELHDDNYVLK 288  SEQ ID NO: 23
cds0007arabidopsisDpa       PAEGFTLPPILLETNPHAVVEIEISEDMQLVHLDFNSTPFSVHDDAYILK 239  SEQ ID NO: 26
AY224529oryzaDPlike         VN-GILLPFLLIKTSRKARVEIEISEDSKFARFDPNGAPFTMHDDVSILE 279  SEQ ID NO: 27
AAO72649.1Dpalikericespliced VN-GILLPFLLIKTSRKARVEIEISEDSKFARFDFNGAPFTMHDDVSILE 279  SEQ ID NO: 27
NP_916921.1Dpalikerice      VN-GILLPFLLIKTSRKARVEIEISEDSKFARFDPNGAPFTMHDDVSILE 274  SEQ ID NO: 28
BAB90030.1DpalikericeGenomic VN-GILLPFLLIKTSRKARVEIEISEDSKFARFDFNGAPFTMHDDVSILE 274  SEQ ID NO: 28
AJ271917triticumDplalike    VN-GIRLPFVLVKTSRKARVEIEISDDSKFAHFEPNGAPFTLHDDLSILE 245  SEQ ID NO: 29
                            *. ***:::      :  *.  .:::.. *.    :::

Cont.
cds573Dp2maize              EMRFCGRE--QHDG--------------------TQESISNGGESSNV 345  SEQ ID NO: 24
cornDP2reconstructed        EMRFCGRE--QHDG--------------------TQESISNGGESSNV 347  SEQ ID NO: 13
AAO72709.1riceE2F_Dpblike_  AMSSCGEE--QIDG--------------------IHDLISNGGESSSM 340  SEQ ID NO: 17
AY224551oryzaDplalike       ALGFSGKE--PDD---------------------TQAWVGNGGECS-T 310  SEQ ID NO: 19
AAO72671.1Dpblikerice       ALGFSGKE--PDD---------------------TQAWVGNGGECS-T 310  SEQ ID NO: 19
cds574Dp2rice               ALGFSGKE--PDD---------------------TQAWVGNGGECS-T 307  SEQ ID NO: 25
riceDP2reconstructed        ALGFSGKE--PDD---------------------TQAWVGNGGECS-T 308  SEQ ID NO: 15
NP_921676.1Dpblikericeslpicedf HPKLRGQT--ELD---------------------YQHRP-------L 296  SEQ ID NO: 21
cds0006arabidopsisDpb       TMKFCDQPPQQPNGRNNSQLVCHNFTPENPNKGPSTGPTPQLDMYETHLQ 338  SEQ ID NO: 02
AY307373Dplapopulus         AMKFCBRP--QSDG--------------------MAPNPPADGGSGSSM 315  SEQ ID NO: 23
cds0007arabidopsisDpa       LMQEQKQE----------------------------QNRVSSSSSTHHQ 260  SEQ ID NO: 26
AY224529oryzaDPlike         AIRRN-KG-----------------------------------------R 287  SEQ ID NO: 27
AAO72649.1Dpalikericespliced AIRRN-KG----------------------------------------R 287  SEQ ID NO: 27
NP_916921.1Dpalikerice      AIRRN-KG-----------------------------------------R 282  SEQ ID NO: 28
BAB90030.1DpalikericeGenomic AIRRN-KG----------------------------------------R 282  SEQ ID NO: 28
AJ271917triticumDplalike    GVRNSIG------------------------------------------K 254  SEQ ID NO: 29

DP conserved region -----|

Cont.
cds573Dp2maize              SNIYWQQA--QHMEMPNNG------TVRLSSSPPIPGILKGRVKHEH 384  SEQ ID NO: 24
cornDP2reconstructed        SNIYWQQA--QHMEMPNNG------TVRLSSSPPIPGILKGRVKHEH 386  SEQ ID NO: 13
AAO72709.1riceE2F_Dpblike_  PNIYRQQV--QQPARSTNG------TARLPSSPPIPGILKGRVKHEH 379  SEQ ID NO: 17
AY224551oryzaDplalike       TPIYHQSP--QVARPNG--------VRLPTSPPIPGILKGRVKHEH 346  SEQ ID NO: 19
AAO72671.1Dpblikerice       TPIYHQSP--QVARPNG--------VRLPTSPPIPGILKGRVKHEH 346  SEQ ID NO: 19
cds574Dp2rice               TPIYHQSP--QVARPNG--------VRLPTSPPIPGILKGRVKHEH 343  SEQ ID NO: 25
riceDP2reconstructed        TPIYHQSP--QVARPNG--------VRLPTSPPIPGILKGRVKHEH 344  SEQ ID NO: 15
NP_921676.1Dpblikericeslpicedf FPVYLKG----VSSMN----------------IRGYYDLLMV--- 318  SEQ ID NO: 21
cds0006arabidopsisDpb       SQQHQQHSQLQIIPMPETNNVTSSADTAPVKSPSLPGIMNSSMKPEN 385  SEQ ID NO: 02
AY307373Dplapopulus         SSMYQP----QILASPSTN-----TPVRHPTSPPLPGIIKARVKNEH 353  SEQ ID NO: 23
cds0007arabidopsisDpa       SQHSSAHS---SSSS----------CIASGTSGPVCWNSGSIDTR 292  SEQ ID NO: 26
AY224529oryzaDPlike         AG-LSIHP-------------------------------------- 294  SEQ ID NO: 27
AAO72649.1Dpalikericespliced AG-LSIHP------------------------------------- 294  SEQ ID NO: 27
NP_916921.1Dpalikerice      AG-LSIHP-------------------------------------- 289  SEQ ID NO: 28
BAB90030.1DpalikericeGenomic AG-LSIHP------------------------------------- 289  SEQ ID NO: 28
AJ271917triticumDplalike    AGRATLH--------------------------------------- 261  SEQ ID NO: 29
```

FIGURE 3 (continued)

SEQUENCE LISTING

<160> NUMBER OF SEQ ID NOS: 30

<210> SEQ ID NO 1
<211> LENGTH: 1158
<212> TYPE: DNA
<213> ORGANISM: Arabidopsis thaliana

<400> SEQUENCE: 1

```
atgacaacta ctgggtctaa ttctaatcac aaccaccatg aaagcaataa taacaacaat      60
aaccctagta ctaggtcttg gggcacggcg gtttcaggtc aatctgtgtc tactagcggc     120
agtatgggct ctccgtcgag ccggagtgag caaaccatca ccgttgttac atctactagc     180
gacactactt ttcaacgcct gaataatttg gacattcaag gtgatgatgc tggttctcaa     240
ggagcttctg gtgttaagaa gaagaagagg ggacagcgtg cggctggtcc agataagact     300
ggaagaggac tacgtcaatt tagtatgaaa gtttgtgaaa aggtggaaag caaaggaagg     360
acaacttaca atgaggttgc agacgagctt gttgctgaat ttgcacttcc aaataacgat     420
ggaacatccc ctgatcagca acagtatgat gagaaaaaca taagacgaag agtatatgat     480
gctttaaacg tcctcatggc tatggatata atatccaagg ataaaaaaga aattcaatgg     540
agaggtcttc ctcggacaag cttaagcgac attgaagaat taaagaacga acgactctca     600
cttaggaaca gaattgagaa gaaaactgca tattcccaag aactggaaga acaatatgta     660
ggccttcaga atctgataca gagaaatgag cacttatata gctcaggaaa tgctcccagt     720
ggcggtgttg ctcttccttt tatccttgtc cagactcgtc ctcacgcaac agtagaagtg     780
gagatatcag aagatatgca gctcgtgcat tttgatttca acagcactcc atttgagctc     840
cacgacgaca attttgtcct caagactatg aagtttgtg atcaaccgcc gcaacaacca     900
aacggtcgga acaacagcca gctggtttgt cacaatttca cgccagaaaa ccctaacaaa     960
ggccccagca caggtccaac accgcagctg gatatgtacg agactcatct tcaatcgcaa    1020
caacatcagc agcattctca gctacaaatc attcctatgc ctgagactaa caacgttact    1080
```

```
tccagcgctg atactgctcc agtgaaatcc ccgtctcttc cagggataat gaactccagc    1140
atgaagccgg agaattga                                                  1158
```

<210> SEQ ID NO 2
<211> LENGTH: 385
<212> TYPE: PRT
<213> ORGANISM: Arabidopsis thaliana

<400> SEQUENCE: 2

```
Met Thr Thr Thr Gly Ser Asn Ser Asn His Asn His Glu Ser Asn
1               5                   10                  15

Asn Asn Asn Asn Asn Pro Ser Thr Arg Ser Trp Gly Thr Ala Val Ser
                20                  25                  30

Gly Gln Ser Val Ser Thr Ser Gly Ser Met Gly Ser Pro Ser Ser Arg
        35                  40                  45

Ser Glu Gln Thr Ile Thr Val Val Thr Ser Ser Asp Thr Thr Phe
    50                  55                  60

Gln Arg Leu Asn Asn Leu Asp Ile Gln Gly Asp Ala Gly Ser Gln
65                  70                  75                  80

Gly Ala Ser Gly Val Lys Lys Lys Arg Gly Gln Arg Ala Ala Gly
                85                  90                  95

Pro Asp Lys Thr Gly Arg Gly Leu Arg Gln Phe Ser Met Lys Val Cys
        100                 105                 110

Glu Lys Val Glu Ser Lys Gly Arg Thr Thr Tyr Asn Glu Val Ala Asp
    115                 120                 125

Glu Leu Val Ala Glu Phe Ala Leu Pro Asn Asn Asp Gly Thr Ser Pro
    130                 135                 140

Asp Gln Gln Gln Tyr Asp Glu Lys Asn Ile Arg Arg Arg Val Tyr Asp
145                 150                 155                 160

Ala Leu Asn Val Leu Met Ala Met Asp Ile Ile Ser Lys Asp Lys Lys
                165                 170                 175

Glu Ile Gln Trp Arg Gly Leu Pro Arg Thr Ser Leu Ser Asp Ile Glu
            180                 185                 190

Glu Leu Lys Asn Glu Arg Leu Ser Leu Arg Asn Arg Ile Glu Lys Lys
        195                 200                 205

Thr Ala Tyr Ser Gln Glu Leu Glu Glu Gln Tyr Val Gly Leu Gln Asn
    210                 215                 220

Leu Ile Gln Arg Asn Glu His Leu Tyr Ser Ser Gly Asn Ala Pro Ser
225                 230                 235                 240

Gly Gly Val Ala Leu Pro Phe Ile Leu Val Gln Thr Arg Pro His Ala
                245                 250                 255

Thr Val Glu Val Glu Ile Ser Glu Asp Met Gln Leu Val His Phe Asp
            260                 265                 270

Phe Asn Ser Thr Pro Phe Glu Leu His Asp Asn Phe Val Leu Lys
        275                 280                 285

Thr Met Lys Phe Cys Asp Gln Pro Gln Gln Pro Asn Gly Arg Asn
    290                 295                 300

Asn Ser Gln Leu Val Cys His Asn Phe Thr Pro Glu Asn Pro Asn Lys
305                 310                 315                 320

Gly Pro Ser Thr Gly Pro Thr Pro Gln Leu Asp Met Tyr Glu Thr His
                325                 330                 335

Leu Gln Ser Gln Gln His Gln Gln His Ser Gln Leu Gln Ile Ile Pro
            340                 345                 350

Met Pro Glu Thr Asn Asn Val Thr Ser Ser Ala Asp Thr Ala Pro Val
        355                 360                 365
```

```
Lys Ser Pro Ser Leu Pro Gly Ile Met Asn Ser Ser Met Lys Pro Glu
    370                 375                 380

Asn
385

<210> SEQ ID NO 3
<211> LENGTH: 1442
<212> TYPE: DNA
<213> ORGANISM: Arabidopsis thaliana

<400> SEQUENCE: 3
tcaaaatcag aaactttcct tgacaaattt taacaaatct ctttctcgtt ttctattgaa      60
ttctccagta gcgcggtagt tagttttagg tggaagaaga atgacaacta ctgggtctaa    120
ttctaatcac aaccaccatg aaagcaataa taacaacaat aaccctagta ctaggtcttg    180
gggcacggcg gtttcaggtc aatctgtgtc tactagcggc agtatgggct ctccgtcgag    240
ccggagtgag caaaccatca ccgttgttac atctactagc gacactactt ttcaacgcct    300
gaataatttg gacattcaag gtgatgatgc tggttctcaa ggagcttctg gtgttaagaa    360
gaagaagagg ggacagcgtg cggctggtcc agataagact ggaagaggac tacgtcaatt    420
tagtatgaaa ggtcttatct ctttctctgc ccctattatg ctttcatcta aatgcctttc    480
aatttgtgaa aaggtggaaa gcaaaggaag gacaacttac aatgaggttg cagacgagct    540
tgttgctgaa tttgcacttc caaataacga tggaacatcc cctgatcagc aacagtatga    600
tgagaaaaac ataagacgaa gagtatatga tgctttaaac gtcctcatgg ctatggatat    660
aatatccaag gataaaaaag aaattcaatg gagaggtctt cctcggacaa gcttaagcga    720
cattgaagaa ttaaagaacg aacgactctc acttaggaac agaattgaga gaaaaactgc    780
atattcccaa gaactggaag aacaagtaat gaacatcatc gatactctcg gcttatctgc    840
ttcctgcctt cagaatctga tacagagaaa tgagcactta tatagctcag gaaatgctcc    900
cagtggcggt gttgctcttc cttttatcct tgtccagact cgtcctcacg caacagtaga    960
agtggagata tcagaagata tgcagctcgt gcattttgat ttcaacagca ctccatttga   1020
gctccacgac gacaattttg tcctcaagac tatgaagttt tgtgatcaac cgccgcaaca   1080
accaaacggt cggaacaaca gccagctggt tgtcacaatt tcacgccag aaaaccctaa    1140 caaaggcccc agcacaggtc caacaccgca gctggatatg tacgagactc atcttcaatc   1200
gcaacaacat cagcagcatt tcagctaca aatcattcct atgcctgaga ctaacaacgt    1260
tacttccagc gctgatactg ctccagtgaa atccccgtct cttccaggga taatgaactc   1320
cagcatgaag ccggagaatt gaaacacgta tgaaggcccc ttgtacaatt tctgtaaaac   1380
tgtaaagtag ctcttgaaaa actttacctg gttttttgac gaatagtctg tttagcggta   1440
aa                                                                   1442

<210> SEQ ID NO 4
<211> LENGTH: 413
<212> TYPE: PRT
<213> ORGANISM: Arabidopsis thaliana

<400> SEQUENCE: 4

Met Thr Thr Thr Gly Ser Asn Ser Asn His Asn His His Glu Ser Asn
1               5                   10                  15

Asn Asn Asn Asn Asn Pro Ser Thr Arg Ser Trp Gly Thr Ala Val Ser
            20                  25                  30

Gly Gln Ser Val Ser Thr Ser Gly Ser Met Gly Ser Pro Ser Ser Arg
```

```
                35                  40                  45
Ser Glu Gln Thr Ile Thr Val Val Thr Ser Thr Ser Asp Thr Thr Phe
 50                  55                  60

Gln Arg Leu Asn Asn Leu Asp Ile Gln Gly Asp Asp Ala Gly Ser Gln
 65                  70                  75                  80

Gly Ala Ser Gly Val Lys Lys Lys Arg Gly Gln Arg Ala Ala Gly
                 85                  90                  95

Pro Asp Lys Thr Gly Arg Gly Leu Arg Gln Phe Ser Met Lys Gly Leu
                100                 105                 110

Ile Ser Phe Ser Ala Pro Ile Met Leu Ser Ser Lys Cys Leu Ser Ile
                115                 120                 125

Cys Glu Lys Val Glu Ser Lys Gly Arg Thr Thr Tyr Asn Glu Val Ala
                130                 135                 140

Asp Glu Leu Val Ala Glu Phe Ala Leu Pro Asn Asn Asp Gly Thr Ser
145                 150                 155                 160

Pro Asp Gln Gln Gln Tyr Asp Glu Lys Asn Ile Arg Arg Val Tyr
                165                 170                 175

Asp Ala Leu Asn Val Leu Met Ala Met Asp Ile Ile Ser Lys Asp Lys
                180                 185                 190

Lys Glu Ile Gln Trp Arg Gly Leu Pro Arg Thr Ser Leu Ser Asp Ile
                195                 200                 205

Glu Glu Leu Lys Asn Glu Arg Leu Ser Leu Arg Asn Arg Ile Glu Lys
                210                 215                 220

Lys Thr Ala Tyr Ser Gln Glu Leu Glu Glu Gln Val Met Asn Ile Ile
225                 230                 235                 240

Asp Thr Leu Gly Leu Ser Ala Ser Cys Leu Gln Asn Leu Ile Gln Arg
                245                 250                 255

Asn Glu His Leu Tyr Ser Ser Gly Asn Ala Pro Ser Gly Gly Val Ala
                260                 265                 270

Leu Pro Phe Ile Leu Val Gln Thr Arg Pro His Ala Thr Val Glu Val
                275                 280                 285

Glu Ile Ser Glu Asp Met Gln Leu Val His Phe Asp Phe Asn Ser Thr
                290                 295                 300

Pro Phe Glu Leu His Asp Asp Asn Phe Val Leu Lys Thr Met Lys Phe
305                 310                 315                 320

Cys Asp Gln Pro Gln Gln Pro Asn Gly Arg Asn Asn Ser Gln Leu
                325                 330                 335

Val Cys His Asn Phe Thr Pro Glu Asn Pro Asn Lys Gly Pro Ser Thr
                340                 345                 350

Gly Pro Thr Pro Gln Leu Asp Met Tyr Glu Thr His Leu Gln Ser Gln
                355                 360                 365

Gln His Gln Gln His Ser Gln Leu Gln Ile Ile Pro Met Pro Glu Thr
                370                 375                 380

Asn Asn Val Thr Ser Ser Ala Asp Thr Ala Pro Val Lys Ser Pro Ser
385                 390                 395                 400

Leu Pro Gly Ile Met Asn Ser Ser Met Lys Pro Glu Asn
                405                 410

<210> SEQ ID NO 5
<211> LENGTH: 58
<212> TYPE: DNA
<213> ORGANISM: Artificial sequence
<220> FEATURE:
<223> OTHER INFORMATION: primer: forward primer

<400> SEQUENCE: 5
```

-continued

```
ggggacaagt tgtacaaaa aagcaggctt cacaatgaca actactgggt ctaattct        58
```

<210> SEQ ID NO 6
<211> LENGTH: 47
<212> TYPE: DNA
<213> ORGANISM: Artificial sequence
<220> FEATURE:
<223> OTHER INFORMATION: primer: reverse primer

<400> SEQUENCE: 6

```
ggggaccact ttgtacaaga aagctgggtt caattctccg gcttcat                   47
```

<210> SEQ ID NO 7
<211> LENGTH: 1243
<212> TYPE: DNA
<213> ORGANISM: Oryza sativa

<400> SEQUENCE: 7

```
aaaaccaccg agggacctga tctgcaccgg ttttgatagt tgagggaccc gttgtgtctg     60
gttttccgat cgagggacga aaatcggatt cggtgtaaag ttaagggacc tcagatgaac    120
ttattccgga gcatgattgg aagggagga cataaggccc atgtcgcatg tgtttggacg     180
gtccagatct ccagatcact cagcaggatc ggccgcgttc gcgtagcacc cgcggtttga    240
ttcggcttcc cgcaaggcgg cggccggtgg ccgtgccgcc gtagcttccg ccggaagcga    300
gcacgccgcc gccgccgacc cggctctgcg tttgcaccgc cttgcacgcg atacatcggg    360
atagatagct actactctct ccgtttcaca atgtaaatca ttctactatt ttccacattc    420
atattgatgt taatgaatat agacatatat atctatttag attcattaac atcaatatga    480
atgtaggaaa tgctagaatg acttacattg tgaattgtga aatggacgaa gtacctacga    540
tggatggatg caggatcatg aaagaattaa tgcaagatcg tatctgccgc atgcaaaatc    600
ttactaattg cgctgcatat atgcatgaca gcctgcatgc gggcgtgtaa gcgtgttcat    660
ccattaggaa gtaaccttgt cattacttat accagtacta catactatat agtattgatt    720
tcatgagcaa atctacaaaa ctggaaagca ataagaaata cgggactgga aaagactcaa    780
cattaatcac caaatatttc gccttctcca gcagaatata tatctctcca tcttgatcac    840
tgtacacact gacagtgtac gcataaacgc agcagccagc ttaactgtcg tctcaccgtc    900
gcacactggc cttccatctc aggctagctt tctcagccac ccatcgtaca tgtcaactcg    960
gcgcgcgcac aggcacaaat tacgtacaaa acgcatgacc aaatcaaaac caccggagaa   1020
gaatcgctcc cgcgcgcggc ggcgacgcgc acgtacgaac gcacgcacgc acgcccaacc   1080
ccacgacacg atcgcgcgcg acgccggcga caccggccgt ccaccgcgc cctcacctcg    1140
ccgactataa atacgtaggc atctgcttga tcttgtcatc catctcacca ccaaaaaaaa   1200
aaggaaaaaa aaacaaaaca caccaagcca aataaaagcg aca                      1243
```

<210> SEQ ID NO 8
<211> LENGTH: 3077
<212> TYPE: DNA
<213> ORGANISM: Artificial sequence
<220> FEATURE:
<223> OTHER INFORMATION: expression cassette

<400> SEQUENCE: 8

```
aaaaccaccg agggacctga tctgcaccgg ttttgatagt tgagggaccc gttgtgtctg     60
gttttccgat cgagggacga aaatcggatt cggtgtaaag ttaagggacc tcagatgaac    120
ttattccgga gcatgattgg aagggagga cataaggccc atgtcgcatg tgtttggacg     180
```

```
gtccagatct ccagatcact cagcaggatc ggccgcgttc gcgtagcacc cgcggtttga    240
ttcggcttcc cgcaaggcgg cggccggtgg ccgtgccgcc gtagcttccg ccggaagcga    300
gcacgccgcc gccgccgacc cggctctgcg tttgcaccgc cttgcacgcg atacatcggg    360
atagatagct actactctct ccgtttcaca atgtaaatca ttctactatt ttccacattc    420
atattgatgt taatgaatat agacatatat atctatttag attcattaac atcaatatga    480
atgtaggaaa tgctagaatg acttacattg tgaattgtga atggacgaa gtacctacga     540 tggatggatg caggatcatg aaagaattaa tgcaagatcg tatctgccgc atgcaaaatc    600
ttactaattg cgctgcatat atgcatgaca gcctgcatgc gggcgtgtaa gcgtgttcat    660
ccattaggaa gtaaccttgt cattacttat accagtacta catactatat agtattgatt    720
tcatgagcaa atctacaaaa ctggaaagca ataagaaata cgggactgga aaagactcaa    780
cattaatcac caaatatttc gccttctcca gcagaatata tatctctcca tcttgatcac    840
tgtacacact gacagtgtac gcataaacgc agcagccagc ttaactgtcg tctcaccgtc    900
gcacactggc cttccatctc aggctagctt tctcagccac ccatcgtaca tgtcaactcg    960
gcgcgcgcac aggcacaaat tacgtacaaa acgcatgacc aaatcaaaac caccggagaa    1020
gaatcgctcc cgcgcgcggc ggcgacgcgc acgtacgaac gcacgcacgc acgcccaacc    1080
ccacgacacg atcgcgcgcg acgccggcga caccggccgt ccacccgcgc cctcacctcg    1140
ccgactataa atacgtaggc atctgcttga tcttgtcatc catctcacca ccaaaaaaaa    1200
aaggaaaaaa aaacaaaaca caccaagcca aataaaagcg acaatttaaa tcaactaggg    1260
atatcacaag tttgtacaaa aaagcaggct tcacaatgac aactactggg tctaattcta    1320
atcacaacca ccatgaaagc aataataaca acaataaccc tagtactagg tcttggggca    1380
cggcggtttc aggtcaatct gtgtctacta gcggcagtat gggctctccg tcgagccgga    1440
gtgagcaaac catcaccgtt gttacatcta ctagcgacac tactttcaa cgcctgaata     1500 atttggacat tcaaggtgat gatgctggtt ctcaaggagc ttctggtgtt aagaagaaga    1560
agaggggaca gcgtgcggct ggtccagata agactggaag aggactacgt caatttagta    1620
tgaaaggtct tatctctttc tctgccccta ttatgctttc atctaaatgc ctttcaattt    1680
gtgaaaaggt ggaaagcaaa ggaaggacaa cttacaatga ggttgcagac gagcttgttg    1740
ctgaatttgc acttccaaat aacgatggaa catcccctga tcagcaacag tatgatgaga    1800
aaaacataag acgaagagta tatgatgctt taaacgtcct catggctatg gatataaatat    1860 ccaaggataa aaaagaaatt caatggagag gtcttcctcg acaagctta agcgacattg      1920 aagaattaaa gaacgaacga ctctcactta ggaacagaat tgagaagaaa actgcatatt    1980
cccaagaact ggaagaacaa gtaatgaaca tcatcgatac tctcggctta tctgcttcct    2040
gccttcagaa tctgatacag agaaatgagc acttatatag ctcaggaaat gctcccagtg    2100
gcggtgttgc tcttccttttt atccttgtcc agactcgtcc tcacgcaaca gtagaagtgg    2160
agatatcaga agatatgcag ctcgtgcatt ttgatttcaa cagcactcca tttgagctcc    2220
acgacgacaa ttttgtcctc aagactatga agttttgtga tcaaccgccg caacaaccaa    2280
acggtcggaa caacagccag ctggtttgtc acaatttcac gccagaaaac cctaacaaag    2340
gccccagcac aggtccaaca ccgcagctgg atatgtacga gactcatctt caatcgcaac    2400
aacatcagca gcattctcag ctacaaatca ttcctatgcc tgagactaac aacgttactt    2460
ccagcgctga tactgctcca gtgaaatccc cgtctcttcc agggataatg aactccagca    2520
tgaagccgga gaattgaacc cagctttctt gtacaaagtg gtgatatcac aagcccgggc    2580
```

```
ggtcttctag ggataacagg gtaattatat ccctctagat cacaagcccg ggcggtcttc    2640
tacgatgatt gagtaataat gtgtcacgca tcaccatggg tggcagtgtc agtgtgagca    2700
atgacctgaa tgaacaattg aaatgaaaag aaaaaaagta ctccatctgt tccaaattaa    2760
aattcatttt aacctttaa taggtttata caataattga tatatgtttt ctgtatatgt     2820
ctaatttgtt atcatccggg cggtcttcta gggataacag gtaattata tccctctaga     2880 caacacacaa caaataagag aaaaaacaaa taatattaat ttgagaatga acaaaaggac    2940
catatcattc attaactctt ctccatccat ttccatttca cagttcgata gcgaaaccg     3000 aataaaaaac acagtaaatt acaagcacaa caaatggtac aagaaaaaca gttttcccaa    3060
tgccataata ctcgaac                                                   3077
```

<210> SEQ ID NO 9
<211> LENGTH: 8
<212> TYPE: PRT
<213> ORGANISM: Artificial sequence
<220> FEATURE:
<223> OTHER INFORMATION: Completely synthesized
<220> FEATURE:
<221> NAME/KEY: misc_feature
<222> LOCATION: (4)..(5)
<223> OTHER INFORMATION: Xaa can be any naturally occurring amino acid

<400> SEQUENCE: 9

Leu Asp Ile Xaa Xaa Asp Asp Ala
1               5

<210> SEQ ID NO 10
<211> LENGTH: 5
<212> TYPE: PRT
<213> ORGANISM: Artificial sequence
<220> FEATURE:
<223> OTHER INFORMATION: Completely synthesized
<220> FEATURE:
<221> NAME/KEY: MISC_FEATURE
<222> LOCATION: (4)..(4)
<223> OTHER INFORMATION: Xaa can be Arg or Lys

<400> SEQUENCE: 10

Lys Lys Lys Xaa Arg
1               5

<210> SEQ ID NO 11
<211> LENGTH: 6
<212> TYPE: PRT
<213> ORGANISM: Artificial sequence
<220> FEATURE:
<223> OTHER INFORMATION: Completely synthesized
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (4)..(4)
<223> OTHER INFORMATION: Xaa can be any naturally occurring amino acid

<400> SEQUENCE: 11

Ala Xaa Gly Xaa Asp Lys
1               5

<210> SEQ ID NO 12
<211> LENGTH: 1550
<212> TYPE: DNA
<213> ORGANISM: Zea mays

```
<400> SEQUENCE: 12
gctccatttt gcccctcgc tcttcacttc ctccgctccg cttgttgtct ccttccctag      60
ggtttgtcca gctccgcgct cagcctcgct cgctagctcc cgctctcctc gatcccgcgg    120
ccccgatcag cgcgatctcc gcgcggccat ggtctccggc gcggcgcaca acccgggcgg    180
gggcgccgcc gcccagacca cccagcgctc gccgccgcag ctggggggcc ggacggccct    240
cgccacgccg ccgccggtct ccgggcgsgc gcgcactcc gcgtctacta gcggcggcac     300
cgctggttca ccaccgtcca gccgcagcga gcagcacgcc cccgacggtg ctgtcaaggg    360
tcccgccctc gcgcgctgcg cccgcagcgg cggcggcggc gtccacgccc gccagcgaca    420
gcacgttcct ccgcttgaac tcgacatcaa csgcgacgac gcgccgtcgt cgcaggctcc    480
cacgagcaag aagaaaagga gaagcacacg ggcagtgggt cctgataaag gtaaccgggg    540
actgcgccag tttagtatga agtttgtga gaaagttgaa agtaagggaa gaacaacata     600
taatgaggtg gcagatgaac ttgttgctga gtttacagac cccaataata atattgaggc    660
accagaccct gataaccctta atgcgcaaca atatgatgaa aaaaatattc gacgaagagt    720
ttatgatgct ttaaatgttc tgatggctat ggacattata tctaaagata aaaaggagat    780
ccagtggaag ggcttgccgc ggactagtat aagtgatatt gaagaattga agactgagct    840
tgtgggactg aaaggtagaa ttgagaagaa aagtgtttac ttacaggagc tacaagatca    900
atatgtaggt ttgcaaaacc tgattcaacg aaatgagcaa ctatatggtt caggaaacac    960
accttctggt ggagtggctt tgccattcat cctagtccag acccgacctc atgcaaccgt   1020
ggaagttgag atatcagaag atatgcagct ggttcatttt gacttcaata gcactccatt   1080
tgagctgcat gatgactcat atgtcctaaa agaaatgcgg ttctgtggaa gagaacaaca   1140
tgatggaact caagagtcga tatcaaatgg aggtgagagt tcaaacgtgt caaatattta   1200
ttggcaacaa gcacagcata tggagatgcc aaacaatggc acagttaggt tatcaagctc   1260
accgccctatt ccagggatat taaaagggcg tgtgaagcac gagcactagc gcttcggttt   1320
tggtttcact ggcgttgtcg tctgagagca gtttgttttta ttactttttct ccgttgtgta   1380
aagcgcctgt aaattattag gcaagggga gggtagtagc tctgatctga tttasctctg   1440
attggtagaa cgacgggtgt aattctatat ccttgattcg gttctttcgg tatggttgag   1500
aaaagggttg acatgtaatt tgtrgrgcat tataaaaact aaaattgttg                1550

<210> SEQ ID NO 13
<211> LENGTH: 386
<212> TYPE: PRT
<213> ORGANISM: Artificial Sequence
<220> FEATURE:
<223> OTHER INFORMATION: Completely synthesized
<220> FEATURE:
<221> NAME/KEY: misc_feature
<222> LOCATION: (40)..(40)
<223> OTHER INFORMATION: Xaa can be any naturally occurring amino acid
<220> FEATURE:
<221> NAME/KEY: misc_feature
<222> LOCATION: (102)..(102)
<223> OTHER INFORMATION: Xaa can be any naturally occurring amino acid

<400> SEQUENCE: 13

Met Val Ser Gly Ala Ala His Asn Pro Gly Gly Gly Ala Ala Ala Gln
 1               5                  10                  15

Thr Thr Gln Arg Ser Pro Pro Gln Leu Gly Ala Arg Thr Ala Leu Ala
            20                  25                  30

Thr Pro Pro Pro Val Ser Gly Xaa Ala Ala His Ser Ala Ser Thr Ser
        35                  40                  45
```

Gly Gly Thr Ala Gly Ser Pro Pro Ser Ser Arg Ser Glu Gln His Ala
         50                  55                  60

Pro Asp Gly Ala Val Lys Gly Pro Ala Leu Ala Arg Cys Ala Arg Ser
 65                  70                  75                  80

Gly Gly Gly Gly Val His Ala Arg Gln Arg Gln His Val Pro Pro Leu
                     85                  90                  95

Glu Leu Asp Ile Asn Xaa Asp Asp Ala Pro Ser Ser Gln Ala Pro Thr
                100                 105                 110

Ser Lys Lys Lys Arg Arg Ser Thr Arg Ala Val Gly Pro Asp Lys Gly
            115                 120                 125

Asn Arg Gly Leu Arg Gln Phe Ser Met Lys Val Cys Glu Lys Val Glu
        130                 135                 140

Ser Lys Gly Arg Thr Thr Tyr Asn Glu Val Ala Asp Glu Leu Val Ala
145                 150                 155                 160

Glu Phe Thr Asp Pro Asn Asn Asn Ile Glu Ala Pro Asp Pro Asp Asn
                165                 170                 175

Pro Asn Ala Gln Gln Tyr Asp Glu Lys Asn Ile Arg Arg Arg Val Tyr
                180                 185                 190

Asp Ala Leu Asn Val Leu Met Ala Met Asp Ile Ile Ser Lys Asp Lys
            195                 200                 205

Lys Glu Ile Gln Trp Lys Gly Leu Pro Arg Thr Ser Ile Ser Asp Ile
210                 215                 220

Glu Glu Leu Lys Thr Glu Leu Val Gly Leu Lys Gly Arg Ile Glu Lys
225                 230                 235                 240

Lys Ser Val Tyr Leu Gln Glu Leu Gln Asp Gln Tyr Val Gly Leu Gln
                245                 250                 255

Asn Leu Ile Gln Arg Asn Glu Gln Leu Tyr Gly Ser Gly Asn Thr Pro
            260                 265                 270

Ser Gly Gly Val Ala Leu Pro Phe Ile Leu Val Gln Thr Arg Pro His
        275                 280                 285

Ala Thr Val Glu Val Glu Ile Ser Gly Asp Met Gln Leu Val His Phe
        290                 295                 300

Asp Phe Asn Ser Thr Pro Phe Glu Leu His Asp Asp Ser Tyr Val Leu
305                 310                 315                 320

Lys Glu Met Arg Phe Cys Gly Arg Glu Gln His Asp Gly Thr Gln Glu
                325                 330                 335

Ser Ile Ser Asn Gly Gly Glu Ser Ser Asn Val Ser Asn Ile Tyr Trp
            340                 345                 350

Gln Gln Ala Gln His Met Glu Met Pro Asn Asn Gly Thr Val Arg Leu
        355                 360                 365

Ser Ser Ser Pro Pro Ile Pro Gly Ile Leu Lys Gly Arg Val Lys His
        370                 375                 380

Glu His
385

<210> SEQ ID NO 14
<211> LENGTH: 1306
<212> TYPE: DNA
<213> ORGANISM: Artificial Sequence
<220> FEATURE:
<223> OTHER INFORMATION: Completely synthesized
<220> FEATURE:
<221> NAME/KEY: misc_feature
<222> LOCATION: (654)..(654)
<223> OTHER INFORMATION: n is a, c, g, or t

<400> SEQUENCE: 14

-continued

```
ccctccatcc atccatcccc cacctccgct ctctagggtt tctcccccgc ctcctccccc    60
ccaatctcgc cgccgcgatg gtctccggcg cggcgcattc ggcctccacc agtggcggcg   120 gcgggggggag cgagggctcc cccaccggcc gcgccgcgcc gggcatgcag gcggcggca   180 gcgccgccac gcccgccgcc tcggcctccg cgtccacgcc ggccagcgag accaccgtcg   240
cccgccgcct cgacggcctc gacatccagg gcgacgacgc gccctcgtcg cagcccgcca   300
cgagcaagaa gaaaaaaagg gggacacgtg caacgggccc tgacaagggt ggccgtggat   360
tgcgccaatt tagtatgaaa gtttgtgaga aagttgaaag caaagggaga acaacctaca   420
acgaggtggc agatgagctt gtagctgagt ttgcagaccc caacaataat tttgcatcac   480
ctgatcctga caaccctaac acaccacaat ttgatgagaa aaatatacga cgaagggttt   540
atgatgcatt gaatgtcctg atggctatgg atattatatc taaggataaa aaggaaattc   600
agtggaaggg cttgcctcgg acaagtatga gcgatgttga agaattgaag gttnagatca   660
tcggactgaa aggtaggatc gacaagaaaa atgcatattt gcaggagtta aagatcaat   720 atgtaggttt gcaaaacctg attcaacgaa acgagcagct ttatggttca ggaaatgctc   780
cttcaggagg agtggcattg ccatttatcc tagttcagac acgtcctcat gctacagtag   840
aagtggagat atcagaagat atgcagctgg tgcattttga tttcaatagc actccatttg   900
aactgcatga cgattccttt gtactgaaag cattggggtt ctctggcaaa gaaccagatg   960
atacgcaagc ctgggttgga atggaggtg agtgctcaac cacacctatc tatcatcaat   1020
caccccaagt tgcgaggcca aacggagtta gactaccaac atcgcccct attcccgta    1080 tacttaaagg gcgtgtcaag catgaacatt aggggttact atgatttgtt gatggtgtga   1140
ggtacttggt ttatttgtta ctccccaatt ttcccttttt gtaactttac atgtagaaag   1200
agcctgtaca ttagatcaat gggggaaaaa tggcgggtct agtttagttt cactggtaga   1260
agatcgatgg gcatgttgac aaaccatatg cctaacttaa cttgta              1306
```

<210> SEQ ID NO 15
<211> LENGTH: 344
<212> TYPE: PRT
<213> ORGANISM: Artificial Sequence
<220> FEATURE:
<223> OTHER INFORMATION: Completely synthesized
<220> FEATURE:
<221> NAME/KEY: misc_feature
<222> LOCATION: (193)..(193)
<223> OTHER INFORMATION: Xaa can be any naturally occurring amino acid

<400> SEQUENCE: 15

```
Met Val Ser Gly Ala Ala His Ser Ala Ser Thr Ser Gly Gly Gly Gly
1               5                   10                  15

Gly Ser Glu Gly Ser Pro Thr Gly Arg Ala Ala Pro Gly Met Gln Gly
            20                  25                  30

Gly Gly Ser Ala Ala Thr Pro Ala Ala Ser Ala Ser Ala Ser Thr Pro
        35                  40                  45

Ala Ser Glu Thr Thr Val Ala Arg Arg Leu Asp Gly Leu Asp Ile Gln
    50                  55                  60

Gly Asp Asp Ala Pro Ser Ser Gln Pro Ala Thr Ser Lys Lys Lys Lys
65                  70                  75                  80

Arg Gly Thr Arg Ala Thr Gly Pro Asp Lys Gly Arg Gly Leu Arg
            85                  90                  95

Gln Phe Ser Met Lys Val Cys Glu Lys Val Glu Ser Lys Gly Arg Thr
            100                 105                 110
```

```
Thr Tyr Asn Glu Val Ala Asp Glu Leu Val Ala Glu Phe Ala Asp Pro
        115                 120                 125

Asn Asn Asn Phe Ala Ser Pro Asp Pro Asp Asn Pro Asn Thr Pro Gln
130                 135                 140

Phe Asp Glu Lys Asn Ile Arg Arg Val Tyr Asp Ala Leu Asn Val
145                 150                 155                 160

Leu Met Ala Met Asp Ile Ile Ser Lys Asp Lys Lys Glu Ile Gln Trp
            165                 170                 175

Lys Gly Leu Pro Arg Thr Ser Met Ser Asp Val Glu Glu Leu Lys Val
                180                 185                 190

Xaa Ile Ile Gly Leu Lys Gly Arg Ile Asp Lys Lys Asn Ala Tyr Leu
            195                 200                 205

Gln Glu Leu Glu Asp Gln Tyr Val Gly Leu Gln Asn Leu Ile Gln Arg
210                 215                 220

Asn Glu Gln Leu Tyr Gly Ser Gly Asn Ala Pro Ser Gly Gly Val Ala
225                 230                 235                 240

Leu Pro Phe Ile Leu Val Gln Thr Arg Pro His Ala Thr Val Glu Val
                245                 250                 255

Glu Ile Ser Glu Asp Met Gln Leu Val His Phe Asp Phe Asn Ser Thr
            260                 265                 270

Pro Phe Glu Leu His Asp Asp Ser Phe Val Leu Lys Ala Leu Gly Phe
            275                 280                 285

Ser Gly Lys Glu Pro Asp Asp Thr Gln Ala Trp Val Gly Asn Gly Gly
    290                 295                 300

Glu Cys Ser Thr Thr Pro Ile Tyr His Gln Ser Pro Gln Val Ala Arg
305                 310                 315                 320

Pro Asn Gly Val Arg Leu Pro Thr Ser Pro Ile Pro Gly Ile Leu
                325                 330                 335

Lys Gly Arg Val Lys His Glu His
            340

<210> SEQ ID NO 16
<211> LENGTH: 1140
<212> TYPE: DNA
<213> ORGANISM: Oryza sativa

<400> SEQUENCE: 16
atggtctccg gcgtcgccca ccgcccggac gacgacggcg ggcgcgccgc ctcgacgttc      60
cagcgcccgc cgcagccggc cggcgcgcgg ccgtccctgg ccacgccgcc gccctcgggc     120
ggagcgcaat ccgcttcgac gagcggcggg agcgcgggct ccccgtccag ccgcagcgag     180
cagcatgtcc ccgcagccgc aggcatggcg gcggggggcgg cggcggcctc tactccgatt     240
agtgagaata ccttcctccg cctcaacgac cttgacatcc acggcgacga tgcgccttcc     300
tcacaggctc caacgagcaa gaagaagaag agaggagcac gagcagttgg tcctgacaaa     360
ggtggcaggg ggctgcgcca gtttagtatg aaggtttgtg agaaagttga agtaaaggg      420 agaacaacat acaacgaggt ggcagatgaa cttgttgccg aatttgcaga tcccaataac     480
agcattttgc caccagatcc ggataatccc aatgcacaac aatatgacga gaaaaatata     540
cggagaaggg tttatgatgc tctgaatgtt ctgatggcta tggagattat atctaaagat     600
aaaaaggaaa ttcagtggaa ggggttgcct cgaaccagta taaatgatat tgaagatttg     660
cagacggaac ttgtaggact gaaaagtagg attgagaaga aaatacata tttgcaggag     720 ctgcaagacc aatttgtagg tatgcaaaag ttgatacaaa gaatgaaca gctatatggt     780 tcaggaaaca ttccctcggg tggagttgca ttaccattta tccttgttca gacacggcct     840
```

```
catgcaactg tggaagttga aatatcagaa gatatgcaac ttgtacattt tgactttaat    900
agcacaccat ttgagttgca tgatgactca tttgtactga aagcaatgag ttcttgtgga    960
gaagaacaaa tcgacggtat tcatgatcta atttcaaatg gaggtgagag ctcaagcatg   1020
ccaaatattt ataggcagca agtgcagcaa cctgcaagat caactaatgg tacagctaga   1080
ttgccaagct cacccctat tccaggaata ctgaaagggc gagtgaagca cgagcattag    1140
```

<210> SEQ ID NO 17
<211> LENGTH: 379
<212> TYPE: PRT
<213> ORGANISM: Oryza sativa

<400> SEQUENCE: 17

```
Met Val Ser Gly Val Ala His Arg Pro Asp Asp Gly Gly Arg Ala
1               5                   10                  15

Ala Ser Thr Phe Gln Arg Pro Gln Pro Ala Gly Ala Arg Pro Ser
                20                  25                  30

Leu Ala Thr Pro Pro Ser Gly Gly Ala Gln Ser Ala Ser Thr Ser
            35                  40                  45

Gly Gly Ser Ala Gly Ser Pro Ser Ser Arg Ser Glu Gln His Val Pro
50                  55                  60

Ala Ala Ala Gly Met Ala Ala Gly Ala Ala Ala Ser Thr Pro Ile
65                  70                  75                  80

Ser Glu Asn Thr Phe Leu Arg Leu Asn Asp Leu Asp Ile His Gly Asp
                85                  90                  95

Asp Ala Pro Ser Ser Gln Ala Pro Thr Ser Lys Lys Lys Arg Gly
                100                 105                 110

Ala Arg Ala Val Gly Pro Asp Lys Gly Arg Gly Leu Arg Gln Phe
            115                 120                 125

Ser Met Lys Val Cys Glu Lys Val Glu Ser Lys Gly Arg Thr Thr Tyr
130                 135                 140

Asn Glu Val Ala Asp Glu Leu Val Ala Glu Phe Ala Asp Pro Asn Asn
145                 150                 155                 160

Ser Ile Leu Pro Pro Asp Pro Asp Asn Pro Asn Ala Gln Gln Tyr Asp
                165                 170                 175

Glu Lys Asn Ile Arg Arg Arg Val Tyr Asp Ala Leu Asn Val Leu Met
                180                 185                 190

Ala Met Glu Ile Ile Ser Lys Asp Lys Lys Glu Ile Gln Trp Lys Gly
            195                 200                 205

Leu Pro Arg Thr Ser Ile Asn Asp Ile Glu Asp Leu Gln Thr Glu Leu
210                 215                 220

Val Gly Leu Lys Ser Arg Ile Glu Lys Lys Asn Thr Tyr Leu Gln Glu
225                 230                 235                 240

Leu Gln Asp Gln Phe Val Gly Met Gln Lys Leu Ile Gln Arg Asn Glu
                245                 250                 255

Gln Leu Tyr Gly Ser Gly Asn Ile Pro Ser Gly Gly Val Ala Leu Pro
            260                 265                 270

Phe Ile Leu Val Gln Thr Arg Pro His Ala Thr Val Glu Val Glu Ile
        275                     280                 285

Ser Glu Asp Met Gln Leu Val His Phe Asp Phe Asn Ser Thr Pro Phe
        290                     295                 300

Glu Leu His Asp Asp Ser Phe Val Leu Lys Ala Met Ser Ser Cys Gly
305                 310                 315                 320

Glu Glu Gln Ile Asp Gly Ile His Asp Leu Ile Ser Asn Gly Gly Glu
```

```
                    325                 330                 335
Ser Ser Ser Met Pro Asn Ile Tyr Arg Gln Gln Val Gln Gln Pro Ala
                340                 345                 350

Arg Ser Thr Asn Gly Thr Ala Arg Leu Pro Ser Pro Pro Ile Pro
            355                 360                 365

Gly Ile Leu Lys Gly Arg Val Lys His Glu His
        370                 375

<210> SEQ ID NO 18
<211> LENGTH: 1041
<212> TYPE: DNA
<213> ORGANISM: Oryza sativa

<400> SEQUENCE: 18
atggtctccg gcgcggcgca ttcggcctcc accagtggcg gcggcggggg gagcgagggc      60
tcccccaccg gccgcgccgc gccgggcatg cagggcggcg gcagcgccgc cacgcccgcc     120
gcctcggcct ccgcgtccac gccggccagc gagaccaccg tcgcccgccg cctcgacggc     180
ctcgacatcc agggcgacga cgcgccctcg tcgcagcccg ccacgagcaa gaagaaaaaa     240
agggggcctg gaacacgtgc aacgggccct gacaagggtg ccgtggatt  gcgccaattt     300 agtatgaaag tttgtgagaa agttgaaagc aaagggagaa caacctacaa cgaggtggca     360
gatgagcttg tagctgagtt tgcagacccc aacaataatt tgcatcacc  tgatcctgac     420 aaccctaaca caccacaatt tgatgagaaa atatacgac  gaagggttta tgatgcattg     480
aatgtcctga tggctatgga tattatatct aaggataaaa aggaaattca gtggaagggc     540
ttgcctcgga caagtatgag cgatgttgaa gaattgaaga cagagatcat cggactgaaa     600
ggtaggatcg acaagaaaaa tgcatatttg caggagttag aagatcaatt tgtaggtctt     660
caaaacttgg cacagcgaaa cgagcagctt tatggttcag gaaatgctcc ttcaggagga     720
gtggcattgc catttatatt ggtgcagaca cgtcctcatg ctacagtaga agtggagata     780
tcagaagata tgcagctggt gcattttgat ttcaatagca ctccatttga actgcatgac     840
gattcctttg tactgaaagc attggggttc tctggcaaag aaccagatga tacgcaagcc     900
tgggttggaa atggaggtga gtgctcaacc acacctatct atcatcaatc accccaagtt     960
gcgaggccaa acgagttag  actaccaaca tcgcccccta ttcccggtat acttaaaggg    1020
cgtgtcaagc atgaacatta g                                             1041

<210> SEQ ID NO 19
<211> LENGTH: 346
<212> TYPE: PRT
<213> ORGANISM: Oryza sativa

<400> SEQUENCE: 19

Met Val Ser Gly Ala Ala His Ser Ala Ser Thr Ser Gly Gly Gly Gly
1               5                   10                  15

Gly Ser Glu Gly Ser Pro Thr Gly Arg Ala Ala Pro Gly Met Gln Gly
            20                  25                  30

Gly Gly Ser Ala Ala Thr Pro Ala Ala Ser Ala Ser Ala Ser Thr Pro
        35                  40                  45

Ala Ser Glu Thr Thr Val Ala Arg Arg Leu Asp Gly Leu Asp Ile Gln
    50                  55                  60

Gly Asp Asp Ala Pro Ser Ser Gln Pro Ala Thr Ser Lys Lys Lys Lys
65                  70                  75                  80

Arg Gly Pro Gly Thr Arg Ala Thr Gly Pro Asp Lys Gly Gly Arg Gly
                85                  90                  95
```

Leu Arg Gln Phe Ser Met Lys Val Cys Glu Lys Val Glu Ser Lys Gly
            100                 105                 110

Arg Thr Thr Tyr Asn Glu Val Ala Asp Glu Leu Val Ala Glu Phe Ala
        115                 120                 125

Asp Pro Asn Asn Asn Phe Ala Ser Pro Asp Pro Asp Asn Pro Asn Thr
    130                 135                 140

Pro Gln Phe Asp Glu Lys Asn Ile Arg Arg Val Tyr Asp Ala Leu
145                 150                 155                 160

Asn Val Leu Met Ala Met Asp Ile Ile Ser Lys Asp Lys Lys Glu Ile
                165                 170                 175

Gln Trp Lys Gly Leu Pro Arg Thr Ser Met Ser Asp Val Glu Glu Leu
            180                 185                 190

Lys Thr Glu Ile Ile Gly Leu Lys Gly Arg Ile Asp Lys Lys Asn Ala
        195                 200                 205

Tyr Leu Gln Glu Leu Glu Asp Gln Phe Val Gly Leu Gln Asn Leu Ala
    210                 215                 220

Gln Arg Asn Glu Gln Leu Tyr Gly Ser Gly Asn Ala Pro Ser Gly Gly
225                 230                 235                 240

Val Ala Leu Pro Phe Ile Leu Val Gln Thr Arg Pro His Ala Thr Val
                245                 250                 255

Glu Val Glu Ile Ser Glu Asp Met Gln Leu Val His Phe Asp Phe Asn
            260                 265                 270

Ser Thr Pro Phe Glu Leu His Asp Asp Ser Phe Val Leu Lys Ala Leu
        275                 280                 285

Gly Phe Ser Gly Lys Glu Pro Asp Asp Thr Gln Ala Trp Val Gly Asn
    290                 295                 300

Gly Gly Glu Cys Ser Thr Thr Pro Ile Tyr His Gln Ser Pro Gln Val
305                 310                 315                 320

Ala Arg Pro Asn Gly Val Arg Leu Pro Thr Ser Pro Ile Pro Gly
                325                 330                 335

Ile Leu Lys Gly Arg Val Lys His Glu His
        340                 345

<210> SEQ ID NO 20
<211> LENGTH: 957
<212> TYPE: DNA
<213> ORGANISM: Oryza sativa

<400> SEQUENCE: 20
atggtctccg gcgcggcgca ttcggcctcc accagtggcg gcggcggggg gagcgagggc        60
tcccccaccg gccgcgccgc gccgggcatg cagggcggcg gcagcgccgc cacgcccgcc       120
gcctcggcct ccgcgtccac gccggccagc gagaccaccg tcgcccgccg cctcgacggg       180
ctcgacatcc agggcgacga cgcgccctcg tcgcagcccg ccacgagcaa gaagaaaaaa       240
agggggcctg gaacacgtgc aacgggccct gacaagggtg gccgtggatt gcgccaattt       300
agtatgaaag tttgtgagaa agttgaaagc aaagggagaa caacctacaa cgaggtggca       360
gatgagcttg tagctgagtt tgcagacccc aacaataatt ttgcatcacc tgatcctgac       420
aaccctaaca caccacaatt tgatgagaaa aatatacgac gaagggttta tgatgcattg       480
aatgtcctga tggctatgga tattatatct aaggataaaa aggaaattca gtggaagggc       540
ttgcctcgga caagtatgag cgatgttgaa gaattgaaga cagagatcat cggactgaaa       600
ggtaggatcg acaagaaaaa tgcatatttg caggagttag aagatcaatt tgtaggtctt       660
caaaacttgg cacagcgaaa cgagcagctt tatggttcag gaaatgctcc ttcaggagga       720

```
gtggcattgc catttatatt ggtgcagcat tggggttctc tggcaaagaa ccagatgata      780
cgcaagcctg ggttggaaat ggaggtgagt gctcaaccac acctatctat catcaatcac      840
cccaagttgc gaggccaaac ggagttagac taccaacatc gccccctatt cccggtatac      900
ttaaagggcg tgtcaagcat gaacattagg ggttactatg atttgttgat ggtgtga         957
```

<210> SEQ ID NO 21
<211> LENGTH: 318
<212> TYPE: PRT
<213> ORGANISM: Oryza sativa

<400> SEQUENCE: 21

```
Met Val Ser Gly Ala Ala His Ser Ala Ser Thr Ser Gly Gly Gly
1               5                   10                  15

Gly Ser Glu Gly Ser Pro Thr Gly Arg Ala Ala Pro Gly Met Gln Gly
            20                  25                  30

Gly Gly Ser Ala Ala Thr Pro Ala Ala Ser Ala Ser Ala Ser Thr Pro
        35                  40                  45

Ala Ser Glu Thr Thr Val Ala Arg Arg Leu Asp Gly Leu Asp Ile Gln
    50                  55                  60

Gly Asp Asp Ala Pro Ser Ser Gln Pro Ala Thr Ser Lys Lys Lys Lys
65                  70                  75                  80

Arg Gly Pro Gly Thr Arg Ala Thr Gly Pro Asp Lys Gly Arg Gly
                85                  90                  95

Leu Arg Gln Phe Ser Met Lys Val Cys Glu Lys Val Glu Ser Lys Gly
            100                 105                 110

Arg Thr Thr Tyr Asn Glu Val Ala Asp Glu Leu Val Ala Glu Phe Ala
        115                 120                 125

Asp Pro Asn Asn Asn Phe Ala Ser Pro Asp Pro Asn Pro Asn Thr
    130                 135                 140

Pro Gln Phe Asp Glu Lys Asn Ile Arg Arg Val Tyr Asp Ala Leu
145                 150                 155                 160

Asn Val Leu Met Ala Met Asp Ile Ile Ser Lys Asp Lys Glu Ile
                165                 170                 175

Gln Trp Lys Gly Leu Pro Arg Thr Ser Met Ser Asp Val Glu Glu Leu
            180                 185                 190

Lys Thr Glu Ile Ile Gly Leu Lys Gly Arg Ile Asp Lys Asn Ala
        195                 200                 205

Tyr Leu Gln Glu Leu Glu Asp Gln Phe Val Gly Leu Gln Asn Leu Ala
    210                 215                 220

Gln Arg Asn Glu Gln Leu Tyr Gly Ser Gly Asn Ala Pro Ser Gly Gly
225                 230                 235                 240

Val Ala Leu Pro Phe Ile Leu Val Gln His Trp Gly Ser Leu Ala Lys
                245                 250                 255

Asn Gln Met Ile Arg Lys Pro Gly Leu Glu Met Glu Val Ser Ala Gln
            260                 265                 270

Pro His Leu Ser Ile Ile Asn His Pro Lys Leu Arg Gly Gln Thr Glu
        275                 280                 285

Leu Asp Tyr Gln His Arg Pro Leu Phe Pro Val Tyr Leu Lys Gly Val
    290                 295                 300

Ser Ser Met Asn Ile Arg Gly Tyr Tyr Asp Leu Leu Met Val
305                 310                 315
```

<210> SEQ ID NO 22
<211> LENGTH: 1640

<212> TYPE: DNA
<213> ORGANISM: Artificial Sequence
<220> FEATURE:
<223> OTHER INFORMATION: Populus tremula x Populus tremuloides

<400> SEQUENCE: 22

```
caaatccaaa caacacgcgt ctctcttctg ttgctttatc atcaacctaa cccaaaccgc      60
cactcctctt ctcttgtata actgaccgtt cccgtcactc tcccttttcc ttttcgttta     120
ttaattcggt ataatttccc atcttttata tcttaatggt cgctggtggg gcccacctgg     180
aagatggaga caggcaccct tcgtcggcct ccagaagagg aggaggagga ggagccacca     240
cgggctcctg ggtgtctggc aatcggtgt caactagcgg cagcgtgggg tctccatcca      300
gcaggagcga gcatgccatg gccactcccg ctagtgacag cactttctta aggttgaacc     360
atctcgacat tcacgccgat gatgccgcca ctcaagatgc cgccgctaat aagaagaaaa     420
agagaggtca acgggctgtt ggagctgata agagtggtag aggacttcgt caatttagca     480
tcaaagtttg tgaaaggtg gaatccaaag gaacaactac ttacaacgag gtagcagatg      540
aacttgtcgc agagtttgct gacccaagca atagtgtttc caccccagat cagcaacaat     600
atgacgagaa aaacatacgg cggagggtat atgatgctct gaatgtactc atggcattag     660
atattatatc taaggataaa aaggaaatac agtggaaagg tcttccccga caagcctaa      720
gtgatattga agaattgaag gttgagcgtc ttggattgag aaatagattc gaaagaaag      780
ctgcctattt gcaagaactg gaggaacaat ttgtaggtct tcagaacctg atacagcgaa     840
atgaacaact gtacagctca ggaaatgctc ctagtggtgg tgtgtcgttg ccttttattc     900
tggtgcagac acgccctcat gcaactgttg aagtggagat atcagaagat atgcagctgg     960
ttcactttga ttttaatagc actcccttcg agctccatga cgataattac gttctcaagg    1020
caatgaaatt ttgtgagaga cctcagagcg atggtatggc acccaatcca cctgctgatg    1080
gaggtgaagg ttctagcatg tccagcatgt atcaaccaca aatccttgct tccccaagta    1140
caaacacccc agttaggcat cctacttcgc cgcctcttcc tggaatcata aaagcacgtg    1200
ttaagaatga gcattgagtc atgcacgatc atctgaacca tgggcaatca tgtcagctgt    1260
gtctgtatat tgtgtaaagt agtttgctgt agatggtgcc tccctataat tatccccgtt    1320
cacagtttgc ccttgttagg aggaactgag atgacaagca gatcggccct tatgctttga    1380
gacttccatg gaaacacttg gttctatctg gttctcagct ttagatccat tattcgcttc    1440
tgtaactgtt taaccatttt ttttccagtt attttttccc attgtagcaa aaattaagtt    1500
tagattgtat taggctacat aggattgtcc agccttactc agaatgatag aatgaattaa    1560
ttcaattctt caagaatttg gtgttataaa aaaaaaaaaa aaaaaaaaaa aaaaaaaaaa    1620
aaaaaaaaaa aaaaaaaaaa                                                1640
```

<210> SEQ ID NO 23
<211> LENGTH: 353
<212> TYPE: PRT
<213> ORGANISM: Artificial Sequence
<220> FEATURE:
<223> OTHER INFORMATION: Populus tremula x Populus tremuloides

<400> SEQUENCE: 23

```
Met Val Ala Gly Gly Ala His Leu Glu Asp Gly Asp Arg His Pro Ser
 1               5                  10                  15

Ser Ala Ser Arg Arg Gly Gly Gly Gly Ala Thr Thr Gly Ser Trp
            20                  25                  30

Val Ser Gly Gln Ser Val Ser Thr Ser Gly Ser Val Gly Ser Pro Ser
```

```
                35                  40                  45
Ser Arg Ser Glu His Ala Met Ala Thr Pro Ala Ser Asp Ser Thr Phe
 50                  55                  60

Leu Arg Leu Asn His Leu Asp Ile His Ala Asp Asp Ala Ala Thr Gln
 65                  70                  75                  80

Asp Ala Ala Asn Lys Lys Lys Arg Gly Gln Arg Ala Val Gly
                 85                  90                  95

Ala Asp Lys Ser Gly Arg Gly Leu Arg Gln Phe Ser Ile Lys Val Cys
                100                 105                 110

Glu Lys Val Glu Ser Lys Gly Thr Thr Thr Tyr Asn Glu Val Ala Asp
            115                 120                 125

Glu Leu Val Ala Glu Phe Ala Asp Pro Ser Asn Ser Val Ser Thr Pro
130                 135                 140

Asp Gln Gln Gln Tyr Asp Glu Lys Asn Ile Arg Arg Val Tyr Asp
145                 150                 155                 160

Ala Leu Asn Val Leu Met Ala Leu Asp Ile Ile Ser Lys Asp Lys Lys
                165                 170                 175

Glu Ile Gln Trp Lys Gly Leu Pro Arg Thr Ser Leu Ser Asp Ile Glu
            180                 185                 190

Glu Leu Lys Val Glu Arg Leu Gly Leu Arg Asn Arg Phe Glu Lys Lys
        195                 200                 205

Ala Ala Tyr Leu Gln Glu Leu Glu Glu Gln Phe Val Gly Leu Gln Asn
    210                 215                 220

Leu Ile Gln Arg Asn Glu Gln Leu Tyr Ser Ser Gly Asn Ala Pro Ser
225                 230                 235                 240

Gly Gly Val Ser Leu Pro Phe Ile Leu Val Gln Thr Arg Pro His Ala
                245                 250                 255

Thr Val Glu Val Glu Ile Ser Glu Asp Met Gln Leu Val His Phe Asp
            260                 265                 270

Phe Asn Ser Thr Pro Phe Glu Leu His Asp Asp Asn Tyr Val Leu Lys
        275                 280                 285

Ala Met Lys Phe Cys Glu Arg Pro Gln Ser Asp Gly Met Ala Pro Asn
    290                 295                 300

Pro Pro Ala Asp Gly Gly Glu Gly Ser Ser Met Ser Ser Met Tyr Gln
305                 310                 315                 320

Pro Gln Ile Leu Ala Ser Pro Ser Thr Asn Thr Pro Val Arg His Pro
                325                 330                 335

Thr Ser Pro Pro Leu Pro Gly Ile Ile Lys Ala Arg Val Lys Asn Glu
            340                 345                 350

His

<210> SEQ ID NO 24
<211> LENGTH: 384
<212> TYPE: PRT
<213> ORGANISM: Zea mays

<400> SEQUENCE: 24

Met Val Ser Gly Ala Ala His Asn Pro Gly Gly Gly Ala Ala Ala Gln
 1               5                  10                  15

Thr Thr Gln Arg Ser Pro Pro Gln Leu Gly Ala Arg Thr Ala Leu Ala
                20                  25                  30

Thr Pro Pro Pro Val Ser Gly Ala Ala His Ser Ala Ser Thr Ser Gly
            35                  40                  45

Gly Thr Ala Gly Ser Pro Pro Ser Ser Arg Ser Glu Gln His Ala Pro
     50                  55                  60
```

Asp Gly Ala Val Lys Gly Pro Ala Leu Ala Arg Cys Ala Arg Ser Gly
65                  70                  75                  80

Gly Gly Gly Val His Ala Arg Gln Arg Gln His Val Pro Pro Leu Glu
                85                  90                  95

Leu Asp Ile Asn Asp Asp Ala Pro Ser Ser Gln Ala Pro Thr Ser Lys
            100                 105                 110

Lys Lys Arg Arg Ser Thr Arg Ala Val Gly Pro Asp Lys Gly Asn Arg
        115                 120                 125

Gly Leu Arg Gln Phe Ser Met Lys Val Cys Glu Lys Val Glu Ser Lys
130                 135                 140

Gly Arg Thr Thr Tyr Asn Glu Val Ala Asp Glu Leu Val Ala Glu Phe
145                 150                 155                 160

Thr Asp Pro Asn Asn Ile Glu Ala Pro Asp Pro Asp Asn Pro Asn
                165                 170                 175

Ala Gln Gln Tyr Asp Glu Lys Asn Ile Arg Arg Val Tyr Asp Ala
            180                 185                 190

Leu Asn Val Leu Met Ala Met Asp Ile Ile Ser Lys Asp Lys Lys Glu
        195                 200                 205

Ile Gln Trp Lys Gly Leu Pro Arg Thr Ser Ile Ser Asp Ile Glu Glu
210                 215                 220

Leu Lys Thr Glu Leu Val Gly Leu Lys Gly Arg Ile Glu Lys Lys Ser
225                 230                 235                 240

Val Tyr Leu Gln Glu Leu Gln Asp Gln Tyr Val Gly Leu Gln Asn Leu
                245                 250                 255

Ile Gln Arg Asn Glu Gln Leu Tyr Gly Ser Gly Asn Thr Pro Ser Gly
            260                 265                 270

Gly Val Ala Leu Pro Phe Ile Leu Val Gln Thr Arg Pro His Ala Thr
        275                 280                 285

Val Glu Val Glu Ile Ser Glu Asp Met Gln Leu Val His Phe Asp Phe
290                 295                 300

Asn Ser Thr Pro Phe Glu Leu His Asp Asp Ser Tyr Val Leu Lys Glu
305                 310                 315                 320

Met Arg Phe Cys Gly Arg Glu Gln His Asp Gly Thr Gln Glu Ser Ile
                325                 330                 335

Ser Asn Gly Gly Glu Ser Ser Asn Val Ser Asn Ile Tyr Trp Gln Gln
            340                 345                 350

Ala Gln His Met Glu Met Pro Asn Asn Gly Thr Val Arg Leu Ser Ser
        355                 360                 365

Ser Pro Pro Ile Pro Gly Ile Leu Lys Gly Arg Val Lys His Glu His
370                 375                 380

<210> SEQ ID NO 25
<211> LENGTH: 343
<212> TYPE: PRT
<213> ORGANISM: Oryza sativa

<400> SEQUENCE: 25

Met Val Ser Gly Ala Ala His Ser Ala Ser Thr Ser Gly Gly Gly Gly
1               5                   10                  15

Gly Ser Glu Gly Ser Pro Thr Gly Arg Ala Ala Pro Gly Met Gln Gly
            20                  25                  30

Gly Gly Ser Ala Ala Thr Pro Ala Ser Ala Ser Ala Ser Thr Pro
        35                  40                  45

Ala Ser Glu Thr Thr Val Ala Arg Arg Leu Asp Gly Leu Asp Ile Gln
50                  55                  60

```
Gly Asp Asp Ala Pro Ser Ser Gln Pro Ala Thr Ser Lys Lys Lys Lys
 65                  70                  75                  80

Arg Gly Thr Arg Ala Thr Gly Pro Asp Lys Gly Arg Gly Leu Arg
                 85                  90                  95

Gln Phe Ser Met Lys Val Cys Glu Lys Val Glu Ser Lys Gly Arg Thr
                100                 105                 110

Thr Tyr Asn Glu Val Ala Asp Glu Leu Val Ala Glu Phe Ala Asp Pro
            115                 120                 125

Asn Asn Asn Phe Ala Ser Pro Asp Pro Asp Asn Pro Asn Thr Pro Gln
130                 135                 140

Phe Asp Glu Lys Asn Ile Arg Arg Val Tyr Asp Ala Leu Asn Val
145                 150                 155                 160

Leu Met Ala Met Asp Ile Ile Ser Lys Asp Lys Lys Glu Ile Gln Trp
                165                 170                 175

Lys Gly Leu Pro Arg Thr Ser Met Ser Asp Val Glu Glu Leu Lys Val
                180                 185                 190

Ile Ile Gly Leu Lys Gly Arg Ile Asp Lys Lys Asn Ala Tyr Leu Gln
                195                 200                 205

Glu Leu Glu Asp Gln Tyr Val Gly Leu Gln Asn Leu Ile Gln Arg Asn
210                 215                 220

Glu Gln Leu Tyr Gly Ser Gly Asn Ala Pro Ser Gly Gly Val Ala Leu
225                 230                 235                 240

Pro Phe Ile Leu Val Gln Thr Arg Pro His Ala Thr Val Glu Val Glu
                245                 250                 255

Ile Ser Glu Asp Met Gln Leu Val His Phe Asp Phe Asn Ser Thr Pro
                260                 265                 270

Phe Glu Leu His Asp Asp Ser Phe Val Leu Lys Ala Leu Gly Phe Ser
                275                 280                 285

Gly Lys Glu Pro Asp Asp Thr Gln Ala Trp Val Gly Asn Gly Gly Glu
                290                 295                 300

Cys Ser Thr Thr Pro Ile Tyr His Gln Ser Pro Gln Val Ala Arg Pro
305                 310                 315                 320

Asn Gly Val Arg Leu Pro Thr Ser Pro Pro Ile Pro Gly Ile Leu Lys
                325                 330                 335

Gly Arg Val Lys His Glu His
                340

<210> SEQ ID NO 26
<211> LENGTH: 343
<212> TYPE: PRT
<213> ORGANISM: Arabidopsis thaliana

<400> SEQUENCE: 26

Met Val Ser Gly Ala Ala His Ser Ala Ser Thr Ser Gly Gly Gly Gly
  1               5                  10                  15

Gly Ser Glu Gly Ser Pro Thr Gly Arg Ala Ala Pro Gly Met Gln Gly
                 20                  25                  30

Gly Gly Ser Ala Ala Thr Pro Ala Ala Ser Ala Ser Ala Ser Thr Pro
                 35                  40                  45

Ala Ser Glu Thr Thr Val Ala Arg Arg Leu Asp Gly Leu Asp Ile Gln
                 50                  55                  60

Gly Asp Asp Ala Pro Ser Ser Gln Pro Ala Thr Ser Lys Lys Lys Lys
 65                  70                  75                  80

Arg Gly Thr Arg Ala Thr Gly Pro Asp Lys Gly Arg Gly Leu Arg
                 85                  90                  95
```

Gln Phe Ser Met Lys Val Cys Glu Lys Val Glu Ser Lys Gly Arg Thr
                100                 105                 110

Thr Tyr Asn Glu Val Ala Asp Glu Leu Val Ala Glu Phe Ala Asp Pro
            115                 120                 125

Asn Asn Asn Phe Ala Ser Pro Asp Pro Asp Asn Pro Asn Thr Pro Gln
        130                 135                 140

Phe Asp Glu Lys Asn Ile Arg Arg Val Tyr Asp Ala Leu Asn Val
145                 150                 155                 160

Leu Met Ala Met Asp Ile Ile Ser Lys Asp Lys Lys Glu Ile Gln Trp
                165                 170                 175

Lys Gly Leu Pro Arg Thr Ser Met Ser Asp Val Glu Glu Leu Lys Val
            180                 185                 190

Ile Ile Gly Leu Lys Gly Arg Ile Asp Lys Lys Asn Ala Tyr Leu Gln
        195                 200                 205

Glu Leu Glu Asp Gln Tyr Val Gly Leu Gln Asn Leu Ile Gln Arg Asn
    210                 215                 220

Glu Gln Leu Tyr Gly Ser Gly Asn Ala Pro Ser Gly Val Ala Leu
225                 230                 235                 240

Pro Phe Ile Leu Val Gln Thr Arg Pro His Ala Thr Val Glu Val Glu
                245                 250                 255

Ile Ser Glu Asp Met Gln Leu Val His Phe Asp Phe Asn Ser Thr Pro
            260                 265                 270

Phe Glu Leu His Asp Asp Ser Phe Val Leu Lys Ala Leu Gly Phe Ser
        275                 280                 285

Gly Lys Glu Pro Asp Asp Thr Gln Ala Trp Val Gly Asn Gly Gly Glu
    290                 295                 300

Cys Ser Thr Thr Pro Ile Tyr His Gln Ser Pro Gln Val Ala Arg Pro
305                 310                 315                 320

Asn Gly Val Arg Leu Pro Thr Ser Pro Pro Ile Pro Gly Ile Leu Lys
                325                 330                 335

Gly Arg Val Lys His Glu His
            340

<210> SEQ ID NO 27
<211> LENGTH: 294
<212> TYPE: PRT
<213> ORGANISM: Oryza sativa

<400> SEQUENCE: 27

Met Ala Pro Pro Cys Gly Asp Ala Ala Ala Ala Ser Ala Ala Pro
1               5                   10                  15

Gly Leu Ala Asn Leu Leu Ile Arg Glu Gly Ala Gly Leu Pro Ser Arg
            20                  25                  30

Pro Glu Arg Tyr Pro Pro Phe Arg Pro Cys Thr Ser Asp Ser Phe Ala
        35                  40                  45

Pro Ile Ser Arg Glu Gly Asp Asp Ile Pro Pro Gln Lys Lys Ser Val
    50                  55                  60

Ser Leu Arg Ser Gly Gly Gly Asn Ala Ala Glu Arg Glu Gly
65                  70                  75                  80

Gly Ala Asn Arg Asn Gly Lys Lys Glu Lys Thr Gly Ala Gln Arg Ile
                85                  90                  95

Thr Gly Trp Gly Leu Arg Glu Phe Ser Lys Ile Val Ser Lys Lys Val
            100                 105                 110

Glu Ala Lys Gly Arg Thr Thr Tyr Asn Glu Val Ala Asp Glu Ile Phe
        115                 120                 125

```
Ala Glu Leu Lys Ser Ile Thr Gln Asn Gly Leu Glu Phe Asp Glu Lys
        130                 135                 140

Asn Ile Arg Arg Val Tyr Asp Ala Phe Asn Val Leu Ile Ala Ile
145                 150                 155                 160

Arg Val Ile Ala Lys Asp Lys Glu Ile Lys Trp Met Gly Leu Thr
                165                 170                 175

Asn Tyr Arg Tyr Glu Lys Ile Gln Lys Leu Glu Glu Val His Lys Glu
            180                 185                 190

Leu Ile Thr Arg Ile Lys Asn Lys Lys Leu Leu Gln Glu Ile Glu
        195                 200                 205

Lys Gln Phe Asp Asp Leu Gln Asn Ile Thr Leu Arg Asn Gln Ala Ser
210                 215                 220

Gln Arg Pro Ala Glu Ser Val Asn Gly Ile Leu Leu Pro Phe Leu Leu
225                 230                 235                 240

Ile Lys Thr Ser Arg Lys Ala Arg Val Glu Ile Glu Ile Ser Glu Asp
                245                 250                 255

Ser Lys Phe Ala Arg Phe Asp Phe Asn Gly Ala Pro Phe Thr Met His
                260                 265                 270

Asp Asp Val Ser Ile Leu Glu Ala Ile Arg Arg Asn Lys Gly Arg Ala
            275                 280                 285

Gly Leu Ser Ile His Pro
        290

<210> SEQ ID NO 28
<211> LENGTH: 289
<212> TYPE: PRT
<213> ORGANISM: Oryza sativa

<400> SEQUENCE: 28

Met Ala Pro Pro Cys Gly Asp Ala Ala Ala Ala Ser Ala Ala Pro
1               5                   10                  15

Gly Leu Ala Asn Leu Leu Ile Arg Glu Gly Ala Gly Leu Pro Ser Arg
            20                  25                  30

Pro Glu Arg Glu Gly Asp Asp Ile Pro Pro Gln Lys Lys Ser Val Ser
        35                  40                  45

Leu Arg Ser Gly Gly Gly Gly Asn Ala Ala Glu Arg Glu Glu Gly Gly
50                  55                  60

Ala Asn Arg Asn Gly Lys Lys Glu Lys Thr Gly Ala Gln Arg Ile Thr
65                  70                  75                  80

Gly Trp Gly Leu Leu Ser Lys Lys Val Glu Ala Lys Gly Arg Thr Thr
                85                  90                  95

Tyr Asn Glu Ile Met Val Gln Thr Ser Asn Asp Glu Val Tyr Thr Ser
            100                 105                 110

Ser Gly Glu Leu Ile Val Ala Asp Glu Ile Phe Ala Glu Leu Lys Ser
        115                 120                 125

Ile Thr Gln Asn Gly Leu Glu Phe Asp Glu Lys Asn Ile Arg Arg Arg
    130                 135                 140

Val Tyr Asp Ala Phe Asn Val Leu Ile Ala Ile Arg Val Ile Ala Lys
145                 150                 155                 160

Asp Lys Lys Glu Ile Lys Trp Met Gly Leu Thr Asn Tyr Arg Tyr Glu
                165                 170                 175

Lys Ile Gln Lys Leu Glu Glu Val His Lys Glu Leu Ile Thr Arg Ile
            180                 185                 190

Lys Asn Lys Lys Lys Leu Leu Gln Glu Ile Glu Lys Gln Phe Asp Asp
        195                 200                 205
```

Leu Gln Asn Ile Thr Leu Arg Asn Gln Ala Ser Gln Arg Pro Ala Glu
    210                 215                 220

Ser Val Asn Gly Ile Leu Leu Pro Phe Leu Leu Ile Lys Thr Ser Arg
225                 230                 235                 240

Lys Ala Arg Val Glu Ile Glu Ile Ser Glu Asp Ser Lys Phe Ala Arg
                245                 250                 255

Phe Asp Phe Asn Gly Ala Pro Phe Thr Met His Asp Asp Val Ser Ile
                260                 265                 270

Leu Glu Ala Ile Arg Arg Asn Lys Gly Arg Ala Gly Leu Ser Ile His
            275                 280                 285

Pro

<210> SEQ ID NO 29
<211> LENGTH: 261
<212> TYPE: PRT
<213> ORGANISM: Triticum aestivum

<400> SEQUENCE: 29

Met Ala Pro Pro Arg Gly Gly Ala Ala Ala Ala Thr Ala Ala Leu
1               5                   10                  15

Asp Leu Thr Gly Val His Ile Leu Glu Ala Ser Ser Val Pro Pro Leu
            20                  25                  30

Pro Glu Arg Gly Gly Asn Ala Val Gln Arg Lys Gly Ala Val Asp Pro
        35                  40                  45

Asp Lys Asp Arg Lys Lys Glu Lys Ala Ala Ala Pro Arg Ile Thr Gly
50                  55                  60

Trp Gly Leu Arg Glu Tyr Ser Lys Ile Val Cys Glu Lys Val Glu Ala
65                  70                  75                  80

Lys Gly Arg Thr Thr Tyr Asn Glu Val Ala Asp Glu Ile Tyr Ser Glu
                85                  90                  95

Leu Lys Ser Met Ala His Ile Gly Gln Gly Phe Asp Glu Lys Asn Ile
            100                 105                 110

Arg Arg Arg Val Tyr Asp Ala Phe Asn Val Leu Ile Ala Leu Arg Val
        115                 120                 125

Ile Ala Lys Glu Lys Lys Glu Ile Arg Trp Met Gly Leu Ser Asn Tyr
130                 135                 140

Arg Tyr Glu Lys Ile Lys Lys Leu Glu Glu Val Arg Lys Glu Leu Val
145                 150                 155                 160

Asn Lys Ile Arg Asn Lys Lys Ala Leu Leu Gln Glu Ile Glu Lys Gln
                165                 170                 175

Phe Asp Asp Leu Gln Asn Ile Lys Leu Arg Asn Gln Thr Leu Glu Ser
            180                 185                 190

Ser Ala Glu Asn Val Asn Gly Ile Arg Leu Pro Phe Val Leu Val Lys
        195                 200                 205

Thr Ser Arg Lys Ala Arg Val Glu Ile Glu Ile Ser Asp Asp Ser Lys
210                 215                 220

Phe Ala His Phe Glu Phe Asn Gly Ala Pro Phe Thr Leu His Asp Asp
225                 230                 235                 240

Leu Ser Ile Leu Glu Gly Val Arg Gly Asn Ser Ile Gly Lys Ala Gly
                245                 250                 255

Arg Ala Thr Leu His
            260

<210> SEQ ID NO 30
<211> LENGTH: 190

```
<212> TYPE: PRT
<213> ORGANISM: Artificial Sequence
<220> FEATURE:
<223> OTHER INFORMATION: Completely synthesized
<220> FEATURE:
<221> NAME/KEY: misc_feature
<222> LOCATION: (24)..(25)
<223> OTHER INFORMATION: Xaa is an optional naturally occurring amino
      acid
<220> FEATURE:
<221> NAME/KEY: misc_feature
<222> LOCATION: (27)..(27)
<223> OTHER INFORMATION: Xaa is an optional naturally occurring amino
      acid
<220> FEATURE:
<221> NAME/KEY: misc_feature
<222> LOCATION: (29)..(29)
<223> OTHER INFORMATION: Xaa is an optional naturally occurring amino
      acid
<220> FEATURE:
<221> NAME/KEY: misc_feature
<222> LOCATION: (30)..(33)
<223> OTHER INFORMATION: Xaa is an optional naturally occurring amino
      acid
<220> FEATURE:
<221> NAME/KEY: misc_feature
<222> LOCATION: (34)..(34)
<223> OTHER INFORMATION: Xaa is an optional naturally occurring amino
      acid
<220> FEATURE:
<221> NAME/KEY: misc_feature
<222> LOCATION: (37)..(38)
<223> OTHER INFORMATION: Xaa is an optional naturally occurring amino
      acid
<220> FEATURE:
<221> NAME/KEY: misc_feature
<222> LOCATION: (40)..(40)
<223> OTHER INFORMATION: Xaa is an optional naturally occurring amino
      acid
<220> FEATURE:
<221> NAME/KEY: misc_feature
<222> LOCATION: (58)..(59)
<223> OTHER INFORMATION: Xaa is an optional naturally occurring amino
      acid
<220> FEATURE:
<221> NAME/KEY: misc_feature
<222> LOCATION: (78)..(79)
<223> OTHER INFORMATION: Xaa is an optional naturally occurring amino
      acid
<220> FEATURE:
<221> NAME/KEY: misc_feature
<222> LOCATION: (81)..(125)
<223> OTHER INFORMATION: Xaa is an optional naturally occurring amino
      acid
<220> FEATURE:
<221> NAME/KEY: misc_feature
<222> LOCATION: (127)..(127)
<223> OTHER INFORMATION: Xaa is an optional naturally occurring amino
      acid
<220> FEATURE:
<221> NAME/KEY: misc_feature
<222> LOCATION: (133)..(133)
<223> OTHER INFORMATION: Xaa is an optional naturally occurring amino
      acid
<220> FEATURE:
<221> NAME/KEY: misc_feature
<222> LOCATION: (136)..(136)
<223> OTHER INFORMATION: Xaa is an optional naturally occurring amino
      acid
<220> FEATURE:
<221> NAME/KEY: misc_feature
<222> LOCATION: (139)..(141)
<223> OTHER INFORMATION: Xaa is an optional naturally occurring amino
      acid
<220> FEATURE:
<221> NAME/KEY: misc_feature
<222> LOCATION: (186)..(187)
<223> OTHER INFORMATION: Xaa is an optional naturally occurring amino
      acid
```

-continued

```
<400> SEQUENCE: 30

Cys Glu Lys Val Glu Ser Lys Gly Arg Thr Thr Tyr Asn Glu Val Ala
1               5                   10                  15

Asp Glu Leu Val Ala Glu Phe Xaa Xaa Pro Xaa Asn Xaa Xaa Xaa Xaa
            20                  25                  30

Xaa Xaa Pro Asp Xaa Xaa Gln Xaa Asp Glu Lys Asn Ile Arg Arg Val
            35                  40                  45

Tyr Asp Ala Leu Asn Val Leu Met Ala Xaa Xaa Ile Ile Ser Lys Asp
            50                  55                  60

Lys Lys Glu Ile Gln Trp Arg Gly Leu Pro Arg Thr Ser Xaa Xaa Asp
65              70                  75                  80

Xaa Xaa Xaa Xaa Xaa Xaa Xaa Xaa Xaa Xaa Xaa Xaa Xaa Xaa Xaa Xaa
            85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa Xaa Leu Xaa Gln
            115                 120                 125

Arg Asn Glu Leu Xaa Tyr Ser Xaa Gly Asn Xaa Xaa Xaa Ser Gly Gly
            130                 135                 140

Val Ala Leu Pro Phe Ile Leu Val Gln Thr Arg Pro His Ala Thr Val
145             150                 155                 160

Glu Val Glu Ile Ser Glu Asp Met Gln Leu Val His Phe Asp Phe Asn
            165                 170                 175

Ser Thr Pro Phe Glu Leu His Asp Asp Xaa Xaa Val Leu Lys
            180                 185                 190
```

PLANTS HAVING IMPROVED GROWTH CHARACTERISTICS AND A METHOD FOR MAKING THE SAME

CROSS-REFERENCE TO RELATED APPLICATIONS

This application claims the benefit of European Application No. 04102392.0 filed May 28, 2004 and United States Provisional Application Ser. No. 60/576,250 filed Jun. 2, 2004, both of which are herein incorporated by reference in their entirety, and is also a divisional application of U.S. Nonprovisional patent application Ser. No. 11/060,029 filed Feb. 17, 2005, now U.S. Pat. No. 7,825,293, also incorporated herein by reference.

The present invention concerns a method for improving plant growth characteristics. More specifically, the present invention concerns a method for improving plant growth characteristics by increasing, in a plant, activity of an E2F Dimerisation Partner (DP) protein in shoot tissue. The present invention also concerns plants transformed with a DP gene, controlled by a shoot-preferred control element, which plants have improved growth characteristics relative to corresponding wild-type plants.

Given the ever-increasing world population, it remains a major goal of agricultural research to improve the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogenous genetic components that may not always result in the desirable trait being passed on from parent plants. In contrast, advances in molecular biology have allowed mankind to more precisely manipulate the germplasm of plants. Genetic engineering of plants entails the isolation and manipulation of genetic material (typically in the form of DNA or RNA) and the subsequent introduction of that genetic material into a plant. Such technology has led to the development of plants having various improved economic, agronomic or horticultural traits. A trait of particular economic interest is high yield and/or biomass.

The ability to improve one or more plant growth characteristics, would have many applications in areas such as crop enhancement, plant breeding, production of ornamental plants, arboriculture, horticulture, forestry, production of algae or plants (for use as bioreactors for example, for the production of pharmaceuticals, such as antibodies or vaccines, or for the bioconversion of organic waste, or for use as fuel, in the case of high-yielding algae and plants).

It has now been found that increased expression and/or activity of DP in shoot-tissue, gives plants having improved growth characteristics relative to corresponding wild-type plants.

Figure 5:
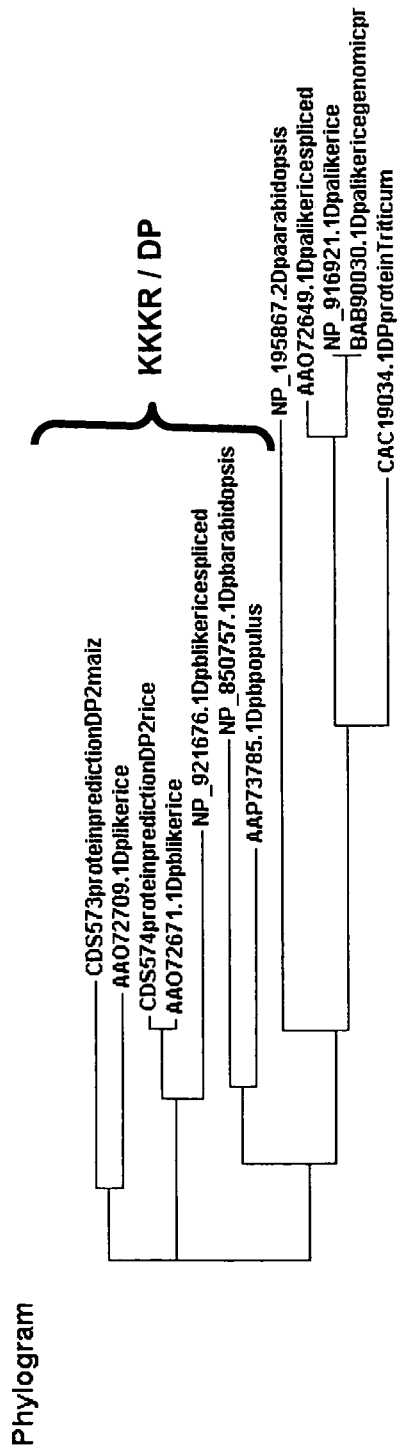

Dp proteins are widely conserved proteins and are involved in the control of the cell cycle (Gutierrez et al. (2002) Current opinion in Plant Biology 5: 480-486). Dp factors act together with E2F factors to form a heterodimer, capable of initiating transcription of S-phase specific genes. The identification of E2F factors, DP factors and E2F-DP-like (DEL) factors has been reported (Magyar et al. 2000, FEBS letters, 486: 79-97). Based on sequence comparison the *Arabidopsis* genes encoding these proteins were grouped into distinct categories as described in Vandepoele et al. 2002, plant cell 14(4): 903-16, which reference is incorporated herein by reference as if fully set forth. The structural characteristics of typical DP proteins are detailed in Magyar et al., which reference is incorporated herein by reference as if fully set forth. For example in FIGS. 3 A and B of Magyar et al. the location of the DNA binding domain and the dimerisation domain in the *Arabidopsis* DP proteins is presented. FIG. 5 of Vandepoele et al. nicely illustrates that DP proteins are distinct from related proteins such as E2F factors and DEL's by the presence of one DNA binding domain and one dimerisation domain.

WO00/47614 (Pioneer Hi-Bred, filed Feb. 11, 2000) suggests that controlling DP expression using tissue-specific or cell-specific promoters provides a differential growth characteristic. More particularly, it suggests that (i) using a seed-specific promoter will stimulate cell division rate and result in increased seed biomass; (ii) using a strongly-expressed, early, tassel-specific promoter will enhance development of this entire reproductive structure; and (iii) that using a root-specific promoter will result in larger roots and faster growth (i.e. more biomass accumulation). However, plants obtainable by these methods, which plants have such differential growth characteristics, have not yet been illustrated or disclosed.

Even the later filed document WO01/21644 (Consejo Superior De Investigaciones Cientificas, filed Sep. 25, 2000), merely suggests that plant growth may be controlled by expression of a recombinant DP. This document does not show transgenic plants, of which plant growth is controlled. Despite the statement "particularly useful are nucleic acids of which the expression is controlled using a tissue-specific promoter or a chemically-inducible promoter", this document did not lead to the development of plants with improved growth characteristics.

Despite the above suggestions, no improved transgenic plants have been generated so far, indicating that using DP as suggested above is insufficient to improve plant growth characteristics.

Unexpectedly, it has now been found that plant growth may be effectively improved by increasing activity of DP specifically in the shoot-tissue of a plant.

Accordingly, the present invention provides a method for improving plant growth characteristics relative to corresponding wild-type plants, comprising increasing activity of a DP polypeptide or homologue thereof specifically in shoot tissue.

Advantageously, performance of the method according to the present invention leads to plants having a variety of improved growth characteristics relative to corresponding wild-type plants, especially increased biomass. The improved growth characteristics may be stable and inheritable in further generations.

The term "growth characteristic" as used herein, preferably refers to, but is not limited to, increased biomass or to any other growth characteristic as described hereinafter.

The term "biomass" refers to the amount of produced biological material. Generally, the term "increased biomass" means an increase in biomass in one or more parts of a plant relative to the biomass of corresponding reference plants, for example relative to corresponding wild-type plants. The plants according to the invention are characterised by increased above-ground biomass, which is particularly important for crop plants grown for their vegetative tissues. For silage corn, for example, typical parameters for economic value are the above-ground biomass and energy content of the leaves. For trees and sugarcane, typical parameters of economical value are the above-ground biomass of stems.

Increased biomass as used herein may also encompass increased seed yield.

The term "growth characteristic" as used herein, also encompasses plant architecture. The plants according to the invention exhibit improved architecture, which is manifested in altered shape, because of their increased above-ground biomass. This characteristic may be advantageous for ornamental plant. The term "architecture" as used herein encompasses the appearance or morphology of a plant, including any one or more structural features or combination of structural features thereof. Such structural features include the shape, size, number, position, texture, arrangement, and pattern of cells, tissues, organs or groups of cells, tissues or organs of a plant. The plants of the present invention are characterised by increased number of tillers and increased number of branches. Therefore, the term altered "architecture" as used herein encompasses altered number and size of tillers, branches or leaves.

The abovementioned growth characteristics may advantageously be modified in a variety of plant species.

The term "plant" as used herein encompasses whole plants, ancestors and progeny of the plants and plant parts, including seeds, shoots, stems, roots (including tubers), and plant cells, tissues and organs. The term "plant" also therefore encompasses suspension cultures, embryos, meristematic regions, callus tissue, leaves, seeds, roots, shoots, gametophytes, sporophytes, pollen, and microspores. Plants that are particularly useful in the methods of the invention include all plants which belong to the superfamily Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calandra* spp, *Camellia sinensis*, *Canna indica*, *Capsicum* spp., *Cassia* spp., *Centroema pubescens*, *Chaenomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Diheteropogon amplectens*, *Dioclea* spp, *Dolichos* spp., *Dorycnium rectum*, *Echinochloa pyramidalis*, *Ehrartia* spp., *Eleusine coracana*, *Eragrestis* spp., *Erythrina* spp., *Eucalyptus* spp., *Euclea schimperi*, *Eulalia villosa*, *Fagopyrum* spp., *Feijoa sellowiana*, *Fragaria* spp., *Flemingia* spp, *Freycinetia banksii*, *Geranium thunbergii*, *Ginkgo biloba*, *Glycine javanica*, *Gliricidia* spp, *Gossypium hirsutum*, *Grevillea* spp., *Guibourtia coleosperma*, *Hedysarum* spp., *Hemarthia altissima*, *Heteropogon contortus*, *Hordeum vulgare*, *Hyparrhenia rufa*, *Hypericum erectum*, *Hyperthelia dissoluta*, *Indigo incarnata*, *Iris* spp., *Leptarrhena pyrolifolia*, *Lespediza* spp., *Lettuca* spp., *Leucaena leucocephala*, *Loudetia simplex*, *Lotonus bainesii*, *Lotus* spp., *Macrotyloma axillare*, *Malus* spp., *Manihot esculenta*, *Medicago sativa*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canariensis*, *Phormium cookianum*, *Photinia* spp., *Picea glauca*, *Pinus* spp., *Pisum sativum*, *Podocarpus totara*, *Pogonarthria fleckii*, *Pogonarthria squarrosa*, *Populus* spp., *Prosopis cineraria*, *Pseudotsuga menziesii*, *Pterolobium stellatum*, *Pyrus communis*, *Quercus* spp., *Rhaphiolepis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys verticillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp. *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, trees, grasses (including forage grass) and algae, amongst others.

According to a preferred feature of the present invention, the plant is a crop plant, such as soybean, sunflower, canola, rapeseed, cotton, alfalfa, tomato, potato, tobacco, papaya, squash, poplar, eucalyptus, pine, leguminosa, flax, lupinus and sorghum. According to a further preferred embodiment of the present invention, the plant is a monocotyledonous plant, such as sugarcane, further preferably the plant is a cereal, such as rice, maize (including forage corn), wheat, barley, millet, oats and rye.

Accordingly, the present invention provides any of the methods as described herein, or a transgenic plant as described herein, wherein the plant is a monocotyledonous plant, preferably a cereal, such as rice or corn.

The term "DP" means E2F Dimerisation Partner. The term "DP polypeptide" as used herein means a protein as represented by SEQ ID NO 2 or homologues of SEQ ID NO 2. Specific examples of DP proteins are *Arabidopsis thaliana* DP proteins as described Magyar et al. (2000, FEBS, 486(1): 79-87), *Triticum aestivum* DP proteins as described in Ramirez-Parra & Gutierrrez (2000, FEBS, 86(1): 73-8) and *Impatiens*, soybean and corn DP proteins as described in WO99/53075 (Du Pont).

The term "DP polypeptide or homologue thereof" as defined herein refers to a polypeptide having in increasing order of preference at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to a DP protein, for example, to any one of SEQ ID NO 2, 4, 13, 15, 17, 19, 21 and 23.

DP proteins of *Arabidopsis thaliana* have been subdivided into two different classes (Vandepoele et al., 2002, Plant Cell., 14(4): 903-16), DPa and DPb. The members of both classes are also encompassed by the term "homologue" as used herein. Advantageously, these different classes DP proteins, or their encoding nucleic acids, may be used in the methods of the present invention. Accordingly, the present invention provides a method as described herein, wherein the DP nucleic acid or DP protein is obtained from a plant, preferably from a dicotyledoneous plant, further preferably from the family Brassicaceae, more preferably from *Arabidopsis thaliana*. According to a further embodiment, DP polypeptide is a DPb polypeptide. A person skilled in the art will recognize that a "DPb" is a protein being closer related to AtDPb, than to AtDPa. This closer relationship may be determined by calculating percentage of sequence identity, or by comparing the presence of conserved motifs as described hereinafter. The closest relationship between the protein in question and AtDPa and AtDPb may also be identified by making a phylogenetic tree as represented, in FIG. 5 and including the protein in question in the tree. A DPb protein should group closer to AtDPb than to AtDPa.

According to a preferred embodiment, such DP polypeptide or homologue has at least one of the conserved DP domains and motifs as described herein. The conserved domains of DP proteins have been illustrated in Magyar et al. and in Vandepoele et al. Typically, a DP protein comprises one DNA binding domain and one dimerisation domain. As an example, the location of these domains is illustrated on the *Arabidopsis thaliana* DPb sequence as shown in FIG. 3.

Preferred DP polypeptides or homologues, useful in the methods of the present invention have a percentage of sequence identity to for example SEQ ID NO 2, 4, 13, 15, 17, 19, 21 and 23 as mentioned above, which percentage of identity may be calculated over the conserved region which is typically present in all DP proteins. This region, which is highly conserved between DP proteins, starts from about residues CEKVES (e.g. from position 111 of SEQ ID NO 2) to about FVLKTM (e.g. to position 290 of SEQ ID NO 2) see FIG. 3.

Three motifs are particularly conserved in a subclass of DP proteins, which subclass comprises DPb of *Arabidopsis thaliana*. The consensus sequences for these "DPb" motifs are represented herein by SEQ ID NO 9 (motif 1, LDIXXDDA), SEQ ID NO 10 (motif 2, KKKK/RR) and SEQ ID NO 11 (motif 3, AXGXDK) (see FIG. 3).

Preferably, these motifs are present in the DP polypeptide or homologues used in the methods of the present invention. FIG. 3 shows an alignment of DP proteins with the location of the "DPb" motifs. As can be seen from the alignment, refining the consensus sequences is possible. For example, at position 4 in motif 1, there is a high probability for a Q or an H residue and at position 5, there is a high probability for a G or an A residue. Also in motif 3, at position 2, there is a high probability for a V, T or A residue and at position 4, there is a high probability for a P or an A residue. A person skilled in the art will recognize that a DPb motif may deviate, by for example 1 or 2 mismatches, from the consensus DPb motifs as represented by SEQ ID NO 9, 10 or 11, without losing its functionality.

These newly identified "DPb" motifs may also be used to search databases and to identify homologous DPb polypeptides and encoding sequences.

The identification of protein domains, motifs and boxes, would also be well within the realm of a person skilled in the art by using domain information available in the PRODOM database available through the University of London (UCL), PIR database available through Georgetown University Medical Center (GUMC), PROSITE database available through ExPASy or the pFAM database available through Washington University in St. Louis. Software programs designed for such domain searching include, but are not limited to, MotifScan, MEME, SIGNALSCAN, and GENES-CAN. MotifScan is a preferred software program and is available at through Stanford University, which program uses the protein domain information of PROSITE and pFAM. A MEME algorithm (Version 3.0) may be found in the GCG package or through the San Diego Supercomputer Center (SDSC). SIGNALSCAN version 4.0 information is available at through the University of Minnesota College of Biological Sciences. GENESCAN may be found through Stanford University.

A DP polypeptide or homologue may be found in (public) sequence databases. Methods for the alignment and identification of DP protein homologues in sequence databases are well known in the art. Such methods, involve screening sequence databases with the sequences provided by the present invention, for example, SEQ ID NOs 2, 4, 13, 15, 17, 19, 21 and 23 (or SEQ ID NO: 1). Different search algorithms and software for the alignment and comparison of sequences are well known in the art and include, for example, GAP, BESTFIT, BLAST, FASTA and TFASTA. Preferably the BLAST software is used, which calculates percent sequence identity and performs a statistical analysis of the similarity between the sequences. The suite of programs referred to as BLAST programs has 5 different implementations: three designed for nucleotide sequence queries (BLASTN, BLASTX, and TBLASTX) and two designed for protein sequence queries (BLASTP and TBLASTN) (Coulson, Trends in Biotechnology: 76-80, 1994; Birren et al., GenomeAnalysis, 1:543, 1997). The software for performing BLAST analysis is publicly available through the National Centre for Biotechnology Information. Useful sequence databases include, but are not limited to, Genbank, available through the National Center for Biotechnology Information (NCBI), the European Molecular Biology Laboratory Nucleic acid Database (EMBL) or versions thereof, available through The European Bioinformatics Institute (EBI), or the MIPS database available through the Munich Information Center for Protein Sequences.

Preferred DP polypeptides used in the methods of the present invention have at least 51% sequence identity with any one of SEQ ID NO 2, 4, 13, 15, 17, 19, 21 and 23. The percentage of sequence identity, may be calculated using a pairwise global alignment program implementing the algorithm of Needleman-Wunsch (J. Mol. Biol. 48: 443-453, 1970), which maximizes the number of matches and keeps the number of gaps to a minimum. For calculation of the above-mentioned percentages, the program needle (EMBOSS package) may be used with a gap opening penalty of 10 and gap extension penalty of 0.1. For proteins, the blosum62 matrix with a word length of 3 is preferably used. For nucleic acids, the program needle uses the matrix "DNA-full", with a word-length of 11, as provided by the EMBOSS package. The Needleman-Wunsch algorithm is best suited for analysing related protein sequences over their full length. Alternatively, analysing related proteins and determining the percentage of sequence identity as mentioned above, may be calculated in the conserved region, domains or motifs as mentioned above.

Examples of polypeptides falling under the definition of "a DP polypeptide or homologue thereof" are *Arabidopsis thaliana* DPb (SEQ ID NO 2 and corresponding encoding sequence SEQ ID NO 1). Other examples of DP proteins are represented by their Genbank accession number in FIG. 3, and their coding sequences as well as their protein sequences are herein represented by SEQ ID NO 12 to 23. The genome sequences of *Arabidopsis thaliana* and *Oryza sativa* are now available in public databases such as Genbank and other genomes are currently being sequenced. Therefore, it is expected that further homologues will readily be identifiable by sequence alignment with any one of SEQ ID NO 1 to 4 or 12 to 23 using the programs BLASTX or BLASTP or other programs.

Despite what may appear to be a relatively low sequence homology (as low as approximately 51%), DP proteins are highly conserved, all of them having a DNA binding domain and a dimerisation domain. It is to be understood that the term DP polypeptide or homologue thereof is not to be limited to the sequences represented by SEQ ID NO 2, 4, 13, 15, 17, 19, 21 and 23, but that any polypeptide meeting the criteria of having at least 51% sequence identity with any one of these SEQ ID NOs and having any of the aforementioned conserved regions, domains or motifs, may be suitable for use in the methods of the invention.

According to a preferred embodiment, such DP polypeptide or homologue retains similar functional and/or biological activity or at least part of the functional and/or biological activity of a DP protein. Typically a DP protein is capable of dimerizing with an E2F transcription factor. This may be tested for example by a Two-Hybrid assay as described in Magyar et al. 2000, FEBS letters, 486: 79-97 or co-immunoprecipitation. Preferably the DP polypeptide or homologue thereof is capable of binding DNA. Biological activity is the activity of the protein when it is in its natural environment. The Biological activity results from its functional activity and results in the modifications in growth characteristics that DP proteins exert as demonstrated in the methods of the present invention.

A DP polypeptide or homologue thereof is encoded by a "DP nucleic acid" or "Dgene". The terms "DP nucleic acid" or "Dgene" are used interchangeably herein and mean a nucleic acid encoding a DP polypeptide or homologue thereof as described hereinabove. Examples of DP nucleic acids include those represented by any one of SEQ ID NO 1, 3, 12, 14, 16, 18, 20 or 22. DP nucleic acids and functional variants thereof may be suitable in practicing the methods of the present invention. Functional variants of DP nucleic acids include portions of a DP nucleic acid and/or nucleic acids capable of hybridising with a DP nucleic acid. The term "functional" in the context of a functional variant refers to a variant which encodes a polypeptide having at least one of the above-mentioned functional domains, conserved region or motifs of a DP protein as described hereinabove and retains part of the functional activity and/or biological activity as described hereinabove.

The term portion as used herein refers to a piece of DNA comprising at least 80 nucleotides and which portion which portion has at least one of the above described domains, conserved regions of motifs of a DP protein. The portion may be prepared, for example, by making one or more deletions to a DP nucleic acid. Preferably, the functional portion is a portion of a nucleic acid as represented by any one of SEQ ID NO 1, 3, 12, 14, 16, 18, 20 or 22.

Another variant DP nucleic acid is a nucleic acid capable of hybridizing, preferably under stringent conditions, with a DP nucleic acid as hereinbefore defined, which hybridizing sequence encodes a polypeptide having at least one of the abovementioned domains, conserved regions or motifs of a DP protein. The hybridizing sequence is preferably at least 80 nucleotides in length. Preferably, the hybridizing sequence is capable of hybridizing to a nucleic acid as represented by any one of SEQ ID NO 1, 3, 12, 14, 16, 18, 20 and 22.

The term "hybridising" as used herein means annealing to a substantially homologous complementary nucleotide sequences in a hybridization process. The hybridisation process may occur entirely in solution, i.e. both complementary nucleic acids are in solution. The hybridisation process may also occur with one of the complementary nucleic acids immobilised to a matrix such as magnetic beads, Sepharose beads or any other resin. The hybridisation process may furthermore occur with one of the complementary nucleic acids immobilised to a solid support such as a nitro-cellulose or nylon membrane or immobilised by e.g. photolithography to e.g. a siliceous glass support (the latter known as nucleic acid arrays or microarrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids. The stringency of hybridisation is influenced by conditions such as temperature, sodium/salt concentration and hybridisation buffer composition.

Hybridization occurs under reduced stringency conditions, preferably under stringent conditions. The stringency of hybridisation is influenced by conditions such as temperature, salt concentration, ionic strength and hybridisation buffer composition. Hybridisation occurs under reduced stringency conditions, preferably under stringent conditions. Examples of stringency conditions are shown in Table 1 below: stringent conditions are those that are at least as stringent as, for example, conditions A-L; and reduced stringency conditions are at least as stringent as, for example, conditions M-R.

TABLE 1

Examples of stringency conditions

| Stringency Condition | Polynucleotide Hybrid± | Hybrid Length (bp)‡ | Hybridization Temperature and Buffer† | Wash Temperature and Buffer† |
|---|---|---|---|---|
| A | DNA:DNA | > or equal to 50 | 65° C.; 1 xSSC- or −42° C.; 1 xSSC, 50% formamide | 65° C.; 0.3 xSSC |
| B | DNA:DNA | <50 | Tb*; 1 xSSC | Tb*; 1 xSSC |
| C | DNA:RNA | > or equal to 50 | 67° C.; 1 xSSC- or −45° C.; 1 xSSC, 50% formamide | 67° C.; 0.3 xSSC |
| D | DNA:RNA | <50 | Td*; 1 xSSC | Td*; 1 xSSC |
| E | RNA:RNA | > or equal to 50 | 70° C.; 1 xSSC- or −50° C.; 1 xSSC, 50% formamide | 70° C.; 0.3 xSSC |
| F | RNA:RNA | <50 | Tf*; 1 xSSC | Tf*; 1 xSSC |
| G | DNA:DNA | > or equal to 50 | 65° C.; 4 xSSC- or −45° C.; 4 xSSC, 50% formamide | 65° C.; 1 xSSC |
| H | DNA:DNA | <50 | Th*; 4°SSC | Th*; 4 xSSC |
| I | DNA:RNA | > or equal to 50 | 67° C.; 4 xSSC- or −45° C.; 4 xSSC, 50% formamide | 67° C.; 1 xSSC |
| J | DNA:RNA | <50 | Tj*; 4 xSSC | Tj*; 4 xSSC |
| K | RNA:RNA | > or equal to 50 | 70° C.; 4 xSSC- or −40° C.; 6 xSSC, 50% formamide | 67° C.; 1 xSSC |
| L | RNA:RNA | <50 | Tl*; 2 xSSC | Tl*; 2 xSSC |

TABLE 1-continued

Examples of stringency conditions

| Stringency Condition | Polynucleotide Hybrid± | Hybrid Length (bp)‡ | Hybridization Temperature and Buffer† | Wash Temperature and Buffer† |
|---|---|---|---|---|
| M | DNA:DNA | > or equal to 50 | 50° C.; 4 xSSC- or −40° C.; 6 xSSC, 50% formamide | 50° C.; 2xSSC |
| N | DNA:DNA | <50 | Tn*; 6 xSSC | Tn*; 6 xSSC |
| O | DNA:RNA | > or equal to 50 | 55° C.; 4 xSSC- or −42° C.; 6 xSSC, 50% formamide | 55 xC.; 2 xSSC |
| P | DNA:RNA | <50 | Tp*; 6 xSSC | Tp*; 6 xSSC |
| Q | RNA:RNA | > or equal to 50 | 60° C.; 4 xSSC- or −45° C.; 6 xSSC, 50% formamide | 60° C.; 2 xSSC |
| R | RNA:RNA | <50 | Tr*; 4 xSSC | Tr*; 4 xSSC |

‡The "hybrid length" is the anticipated length for the hybridising nucleic acid. When nucleic acids of known sequence are hybridised, the hybrid length may be determined by aligning the sequences and identifying the conserved regions described herein.
†SSPE (1 xSSPE is 0.15M NaCl, 10 mM NaH2PO4, and 1.25 mM EDTA, pH 7.4) may be substituted for SSC (1 xSSC is 0.15M NaCl and 15 mM sodium citrate) in the hybridisation and wash buffers; washes are performed for 15 minutes after hybridisation is complete. The hybridisations and washes may additionally include 5 × Denhardt's reagent, .5-1.0% SDS, 100 µg/ml denatured, fragmented salmon sperm DNA, 0.5% sodium pyrophosphate, and up to 50% formamide.
*Tb-Tr: The hybridization temperature for hybrids anticipated to be less than 50 base pairs in length should be 5-10° C. less than the melting temperature Tm of the hybrids there Tm is determined according to the following equations. For hybrids less than 18 base pairs in length, Tm (° C.) = 2 (# of A + T bases) + 4 (# of G + C. bases). For hybrids between 18 # and 49 base pairs in length, Tm (° C.) = 81.5 + 16.6 (log.sub.10[Na+]) + 0.41 (% G + C.) − (600/N), where N is the number of bases in the hybrid, and [Na+] is the concentration of sodium ions in the hybridization buffer ([NA+] for 1 xSSC + .165M).
±The present invention encompasses the substitution of any one, or more DNA or RNA hybrid partners with either a PNA, or a modified nucleic acid.

Other variant DP nucleic acids useful in the methods of the present invention are allelic variants of a DP nucleic acid, splice variants, variants due to the degeneracy of the genetic code, family members of a DP nucleic acid and variants interrupted by one or more intervening sequences, such as introns, spacer sequences or transposons.

DP nucleic acids or functional variants thereof may be in the form of DNA, or a complement DNA, RNA, cDNA, genomic DNA, synthetic DNA as a whole or a part, double-stranded or single-stranded nucleic acid.

The methods according to the present invention may also be practised using one of the above-mentioned DP variants, for example using an alternative splice variant of SEQ ID NO 1. One example of an alternative splice variant of SEQ ID NO 1 is herein represented by SEQ ID NO 3. Other examples of splice variants are found in *Oryza sativa*, where two DPb proteins each have two different splice forms: AA072709.1 and AY224589 are two splice variants of the same genomic DNA, and AA072671.1 and AY224551 are two splice forms of the same genomic DNA encoding the other DPb protein. The term "alternative splice variant" as used herein encompasses variants of a nucleic acid in which selected introns and/or exons have been excised, replaced or added. Suitable splice variants will be the ones in which the functional and/or biological function of the protein is retained, which may be achieved by selectively retaining functional segments of the protein. Such splice variants may be found in nature or may be manmade. Methods for making such splice variants are well known in the art.

Another variant DP nucleic acid useful in practising the method of the present invention is an allelic variant of a DP gene, for example, an allelic variant of SEQ ID NO 1. Allelic variants exist in nature and encompassed within the methods of the present invention is the use of these natural alleles. Allelic variants also encompass Single Nucleotide Polymorphisms (SNPs) as well as Small Insertion/Deletion Polymorphisms (INDELs). The size of INDELs is usually less than 100 bp. SNPs and INDELs form the largest set of sequence variants in naturally occurring polymorphic strains of most organisms.

The DP nucleic acid or variant thereof may be derived from any natural or artificial source. The nucleic acid/gene or variant thereof may be isolated from a microbial source, such as bacteria, yeast or fungi, or from a plant, algae or animal (including human) source. This nucleic acid may be modified from its native form in composition and/or genomic environment through deliberate human manipulation. The nucleic acid is preferably of plant origin, whether from the same plant species (for example to the one in which it is to be introduced) or whether from a different plant species. The nucleic acid may be isolated from a dicotyledonous species, preferably from the family Brassicaceae, further preferably from *Arabidopsis thaliana*. More preferably, the DP isolated from *Arabidopsis thaliana* is represented as by SEQ ID NO 1 or 3, and the DP amino acid sequence is as represented by SEQ ID NO 2 or 4. Other preferred sequences are as represented by SEQ ID NO 12, 14, 16, 18, 20 and 22 and the corresponding amino acid sequence as represented by SEQ ID NO 13, 15, 17, 19, 21 or 23.

The DP nucleic acid sequence useful in the methods of the present invention may have at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to a DP nucleic acid, for example, to any one of SEQ ID NO 1, 3, 12, 14, 16, 18, 20 or 22.

"Homologues" of a protein encompass peptides, oligopeptides, polypeptides, proteins and enzymes having an amino acid substitution, deletion and/or insertion relative to the unmodified protein in question and having similar biological and functional activity as the unmodified protein from which they are derived. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company).

Homologues of a particular DP protein may exist in nature and may be found in the same or different species or organism from which the particular DP protein is derived. Two special forms of homologues, orthologues and paralogues, are evolutionary concepts used to describe ancestral relationships of genes. The term "orthologues" relates to genes in different organisms that are homologous due to ancestral relationship. The term "paralogues" relates to gene-duplications within the genome of a species leading to paralogous genes. The term "homologues" as used herein also encompasses paralogues and orthologues of a DP protein, which are also useful in practising the methods of the present invention.

Orthologues of a DP protein in other plant species may easily be found by performing a reciprocal Blast search. This method comprises searching one or more sequence databases with a query gene or protein (for example, any one of SEQ ID NO 1 to 4 or 12 to 23), using for example, the BLAST program. The highest-ranking subject genes that result from this search are then used as a query sequence in a similar BLAST search. Only those genes that have as a highest match again the original query sequence are considered to be orthologous genes. For example, to find a rice orthologue of an *Arabidopsis thaliana* gene, one may perform a BLASTN or TBLASTX analysis on a rice database such as the *Oryza sativa Nipponbare* database available at the NCBI website (<www.ncbi.nlm.nih.gov>). In a next step, the highest ranking rice sequences are used in a reverse BLAST search on an *Arabidopsis thaliana* sequence database. The method may be used to identify orthologues from many different species, for example, from corn.

Paralogues of a DP protein in the same species may easily be found by performing a Blast search on sequences of the same species from which the DP protein is derived. From the sequences that are selected by the Blast search, the true paralogues may be identified by looking for the highest sequence identity. Preferably a DP paralogue comprises the conserved DP region as described hereinabove. Further preferably, a DP paralogue comprises the DPb motifs as described hereinafter.

Some of the DP variants or homologues as mentioned hereinabove may occur in nature and may be isolated from nature. Once the sequence of a homologue is known, and its corresponding encoding sequence, the person skilled in the art will be able to isolate the corresponding DP nucleic acid from biological material such as genomic libraries, for example, by the technique of PCR. One example of such an experiment is outlined in Example 1. Alternatively, when the sequence is not known, new DP proteins may be isolated from biological material via hybridization techniques based on probes from known DP proteins.

Alternatively and/or additionally, some DP variants or homologues as mentioned above may be manmade via techniques involving, for example, mutation (substitution, insertion or deletion) or derivation. These variants are herein referred to as "derivatives", which derivatives are also useful in the methods of the present invention. Derivatives of a protein may readily be made using peptide synthesis techniques well known in the art, such as solid phase peptide synthesis and the like, or by protein engineering via recombinant DNA manipulations. The manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesis protocols.

Accordingly, a homologue may be in the format of a substitutional variant. The term "substitutional variants" of a DP protein refers to those variants in which at least one residue in an amino acid sequence has been removed and a different amino acid inserted in its place. Amino acid substitutions are typically of single residues, but may be clustered depending upon functional constraints placed upon the polypeptide; insertions usually are of the order of about 1-10 amino acids, and deletions can range from about 1-20 amino acids. Preferably, amino acid substitutions comprise conservative amino acid substitutions.

Homologues may also be in the form of an "insertional variants" of a protein in which one or more amino acids are introduced into a predetermined site in the DP protein. Insertions may comprise amino-terminal and/or carboxy-terminal fusion as well as intra-sequence insertion of single or multiple amino acids. Generally, insertions within the amino acid sequence are of the order of about 1 to 10 amino acids. Examples of amino- or carboxy-terminal fusions include fusion of the binding domain or activation domain of a transcriptional activator as used in the yeast two-hybrid system, phage coat proteins, (histidine)6-tag, glutathione S-transferase-tag, protein A, maltose-binding protein, dihydrofolate reductase, Tag•100 epitope, c-myc epitope, FLAG-epitope, lacZ, CMP (calmodulin-binding peptide), HA epitope, protein C epitope and VSV epitope.

Homologues in the form of "deletion variants", are characterised by the removal of one or more amino acids from the protein.

The DP polypeptide of homologue thereof may be a derivative in the form of peptides, oligopeptides, polypeptides, proteins or enzymes, characterised by substitutions, and/or deletions and/or additions of naturally and non-naturally occurring amino acids compared to the amino acids of a naturally-occurring DP protein. A derivative may also comprise one or more non-amino acid substituents compared to the amino acid sequence from which it is derived. Such non-amino acid substituents include for example, non-naturally occurring amino acids, a reporter molecule or other ligand, covalently or non-covalently bound to the amino acid sequence. Such a reporter molecule may be bound to facilitate the detection of the DP protein.

Another type of DP polypeptide useful in the methods of the present invention is an active fragment of a DP protein. "Active fragments" of a DP protein encompass at least 80 contiguous amino acid residues of a DP protein, which residues retain similar biological and/or functional activity to a naturally occurring protein or a part thereof. Suitable fragments include fragments of a DP protein starting at the second or third or further internal methionine residues. These fragments originate from protein translation, starting at internal ATG codons, whilst retaining its functionality in the methods of the present invention. Suitable functional fragments of a DP protein, or suitable portions of nucleic acids that correspond to such fragments, useful in the methods of the present invention, may have one or more of the conserved region, domain or motifs as described herein above, whilst retaining its functionality in the methods of the present invention. One particular example of a functional fragment is the fragment corresponding to the conserved region common to all DP proteins, as marked in FIG. 3 and further described hereinabove.

The activity of a DP polypeptide or a homologue thereof may be increased by introducing a genetic modification (preferably in the locus of an DP gene). The locus of a gene as defined herein is taken to mean a genomic region, which includes the gene of interest and 10 KB up- or down stream of the coding region.

The genetic modification may be introduced, for example, by any one (or more) of the following methods: TDNA activation, tilling, site-directed mutagenesis, homologous recombination or by introducing and expressing in a plant a nucleic acid encoding an DP polypeptide or a homologue thereof. Following introduction of the genetic modification there follows a step of selecting for increased activity of a DP polypeptide, which increase in activity gives plants having improved growth characteristics.

T-DNA activation tagging (Hayashi et al. Science (1992) 1350-1353) involves insertion of T-DNA usually containing a promoter (may also be a translation enhancer or an intron), in the genomic region of the gene of interest or 10 KB up- or down stream of the coding region of a gene in a configuration such that such promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobacterium* infection and leads to overexpression of genes near to the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of a DP gene using the technique of TILLING (Targeted Induced Local Lesions IN Genomes). This is a mutagenesis technology useful to generate and/or identify, and to eventually isolate mutagenised variants of a DP nucleic acid capable of exhibiting DP activity. TILLING also allows selection of plants carrying such mutant variants. These mutant variants may even exhibit higher DP activity than that exhibited by the gene in its natural form. TILLNG combines high-density mutagenesis with high-throughput screening methods. The steps typically followed in TILLING are: (a) EMS mutagenesis (Redei and Koncz. 1992; Feldmann et al., 1994; Lightner and Caspar, 1998); (b) DNA preparation and pooling of individuals; (c) PCR amplification of a region of interest; (d) denaturation and annealing to allow formation of heteroduplexes; (e) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum Nat. Biotechnol. 2000 April; 18(4):455-7, reviewed by Stemple 2004 (TILLING a high-throughput harvest for functional genomics. Nat Rev Genet. 2004 5(2):145-50).

Site directed mutagenesis may be used to generate variants of DP nucleic acids or portions thereof that retain activity. Several methods are available to achieve site directed mutagenesis, the most common being PCR based methods (current protocols in molecular biology. Wiley Eds. <www.4ulr.com/products/currentprotocols/index.html>).

TDNA activation, TILLING and site-directed mutagenesis are examples of technologies that enable the generation novel alleles and DP variants that retain DP function and which are therefore useful in the methods of the invention.

Homologous recombination allows introduction in a genome of a selected nucleic acid at a defined selected position. Homologous recombination is a standard technology used routinely in biological sciences for lower organism such as yeast or the moss physcomitrella. Methods for performing homologous recombination in plants have been described not only for model plants (Offringa et al. Extrachromosomal homologous recombination and gene targeting in plant cells after *Agrobacterium*-mediated transformation. 1990 EMBO J. 1990 October; 9(10): 3077-84) but also for crop plants, for example rice (Terada R et al. Nat. Biotechnol. 2002 Efficient gene targeting by homologous recombination in rice; Lida and Terada Curr Opin Biotechnol. 2004 15(2): 132-8: A tale of two integrations, transgene and T-DNA: gene targeting by homologous recombination in rice). The nucleic acid to be targeted (which may be a DP nucleic acid or variant thereof as hereinbefore defined) need not be targeted to the locus of a DP gene, but may be introduced in, for example, regions of high expression. The nucleic acid to be targeted may be an improved allele used to replace the endogenous gene or may be introduced in addition or the endogenous gene.

According to a preferred embodiment of the invention, plant growth characteristics may be improved by introducing in a plant and expressing a nucleic acid encoding a DP polypeptide or a homologue thereof. According to a preferred embodiment of the present invention, the expression is preferably in the shoot tissue of the plant.

A preferred method for introducing a genetic modification (which in this case need not be in the locus of an DP gene) is to introduce and express in a plant a nucleic acid encoding a DP polypeptide or a homologue thereof. A DP polypeptide or a homologue thereof as mentioned above is one having in increasing order of preference, at least 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% sequence identity to a DP protein, for example, to any one of SEQ ID NO 2, 4, 13, 15, 17, 19, 21 and 23. Preferably said DP polypeptide comprises at least one of the aforementioned conserved region, domains or motifs.

According to a preferred aspect of the present invention, enhanced or increased expression of the DP nucleic acid or variant thereof is envisaged. Methods for obtaining enhanced or increased expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of an DP nucleic acid or variant thereof. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene.

According to the methods of the present invention, the activity of DP is increase specifically in shoot tissue, and preferably this is mediated by increased expression of a DP nucleic acid specifically in shoot tissue. The term "shoot" as used herein encompasses all aerial parts of the plants. Typical shoot-tissues include but are not limited to tissues of stems, branches, leaves, buds, flowers, reproductive organs, seeds, and shoot-derived structures such as stolons, corms, bulbs or tubers. Preferably in the methods of the present invention the DP gene is preferentially expressed in young shoot tissue.

In a preferred method of the present invention, the shoot-tissue-specific expression of the DP gene is mediated by a shoot-tissue-specific promoter operable linked to the introduced DP gene. Therefore, according to a preferred embodiment of the invention there is provided a method for improving plant growth characteristics relative to corresponding wild-type plants, comprising the introduction into a plant of a nucleic acid encoding a DP protein, and comprising the expression of said nucleic acid specifically in shoot-tissue.

The term "shoot-tissue specific promoter" means a promoter that is at least 5 times stronger in shoot than in other plant organs, such as roots. The shoot-tissue-specific promoter is a tissue-specific promoter, characterized by the fact that it preferentially, but not exclusively expressed in aerial parts of the plant. The term "tissue-specific" promoter may be used interchangeably herein with a "tissue-preferred" promoter.

Alternatively, the shoot-tissue-specific expression of the DP gene is mediated by selective transformation techniques, where for example ballistics are used to transform the aerial tissues.

Alternatively, the shoot-tissue-specific expression of the DP gene is mediated by T-DNA tagging, a technique well known by a person skilled in the art. For example, one can introduce a promoter randomly in the plant and select those plants in which the DP expression is increased specifically in the shoot tissues.

If polypeptide expression is desired, it is generally desirable to include a polyadenylation region at the 3'-end of a polynucleotide coding region. The polyadenylation region can be derived from the natural gene, from a variety of other plant genes, or from T-DNA. The 3' end sequence to be added may be derived from, for example, the nopaline synthase or octopine synthase genes, or alternatively from another plant gene, or less preferably from any other eukaryotic gene.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, Mol. Cell biol. 8:4395-4405 (1988); Callis et al., Genes Dev. 1:1183-1200 (1987). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

The invention also provides genetic constructs and vectors to facilitate introduction and/or expression of the nucleotide sequences useful in the methods according to the invention.

Therefore, according to a further embodiment of the present invention, there is provided a genetic construct comprising:
  (a) a DP nucleic acid or a variant thereof;
  (b) one or more control sequences capable of preferentially expressing the nucleic acid of (a) in shoot tissue; and optionally
  (c) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for maintenance and expression of the gene of interest in the transformed cells. Preferably, the genetic construct according to the present invention is a plant expression vector, suitable for introduction and/or maintenance and/or expression of a nucleic acid in a plant cell, tissue, organ or whole plant.

One example of a genetic construct according to the present invention is herein represented by SEQ ID NO 8 and encompasses a DP gene under the control of a rice beta-expansin promoter and followed by a double transcription termination sequence (see FIG. 2).

Accordingly, the present invention provides genetic constructs as described above wherein the control sequence of (b) is a shoot-tissue preferred promoter, such as a beta-expansin promoter or a promoter having a comparable expression profile to the beta-expansin promoter.

The nucleic acid according to (a) is advantageously any of the nucleic acids described hereinbefore. A preferred nucleic acid is a nucleic acid represented by SEQ ID NO 1, 2, 12, 14, 16, 18, 20 or 22 or a functional variant thereof as described hereinabove, or is a nucleic acid encoding a protein as represented by SEQ ID NO 2, 4, 13, 15, 17, 19, 21 or 23 or a variant thereof as described hereinabove.

Plants are transformed with a vector comprising the sequence of interest (i.e. a DP nucleic acid or a variant thereof). The sequence of interest is operably linked to one or more control sequences, preferably a promoter described as above. With the term "promoter" it meant a transcription control sequence. The promoter of (b) is operable in a plant, and suitable promoters are preferably derived from a plant sequence. The terms "transcription control sequence" or "promoter" are used interchangeably herein and are to be taken in a broad context to refer to regulatory nucleic acids capable of effecting expression of the sequences to which they are operably linked. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative, which confers, activates or enhances expression of a nucleic acid molecule in a cell, tissue or organ.

The term "operably linked" as used herein refers to a functional linkage between the promoter sequence and the gene of interest, such that the promoter sequence is able to initiate transcription of the gene of interest. Preferably, the gene of interest is operably linked in the sense orientation to the promoter.

Advantageously, any promoter may be used for the methods of the invention, provided that it has a shoot-tissue-specific expression pattern. These promoters have, when compared to a strong constitutive promoter (such as the strong constitutive/ubiquitous CaMV35S promoter), a lower expression level in roots.

One example of such a promoter the rice beta-expansin promoter EXPB9, represented herein by SEQ ID NO 7. This promoter may be isolated from the *Oryza sativa* (japonica cultivar-group) chromosome 10, BAC OSJNBa0082M15, where it is located upstream of EXPB9 gene encoding the mRNA as represented by the Genbank accession number AF261277. The term "shoot-tissue-specific promoter" as used herein therefore also means a promoter that has the same or similar activity, as the rice beta-expansin promoter EXPB9 in *Oryza sativa*. Similar activity in this context means an activity that is at most 20-fold higher or lower than the beta-expansin promoter EXPB9, preferably at most 10-fold higher or lower or 5-fold higher or lower or 3-fold higher or lower.

One method to measure the promoter strength is through the use of promoter-beta-glucuronidase fusions. The promoter if hereby fused to the *Escherichia coli* UidA gene encoding beta-glucuronidase and the chimeric construct is transformed into a plant. Proteins are extracted from the plant material and GUS activity is measured (Jefferson et al., 1987, EMBO J. 20; 6(13):3901-7). Promoter activity is then calculated as the optical density in units per mg of extracted protein.

Preferably, the shoot-tissue-preferred promoter is expressed preferably during vegetative growth of the plant or in young shoot-tissue. Therefore, in the context of this invention, GUS activity is preferably measured from tissues after germination. Preferably, these measurements are performed during vegetative growth of the plant, for example after 2, preferably after 4 weeks post germination.

Another example of a shoot-tissue-preferred promoter is a protochlorophyl reductase promoter.

Optionally, in the genetic construct according to the invention, one or more terminator sequences may also be incorporated. The term "transcription termination sequence" encompasses a control sequence at the end of a transcriptional unit, which signals 3' processing and polyadenylation of a primary transcript and termination of transcription. Additional regulatory elements, such as transcriptional or translational enhancers, may be incorporated in the genetic construct. Those skilled in the art will be aware of terminator and enhancer sequences, which may be suitable for use in performing the invention. Such sequences would be known or may readily be obtained by a person skilled in the art.

The genetic constructs of the invention may further include an origin of replication, which is required for maintenance and/or replication in a specific cell type. One example is when a genetic construct is required to be maintained in a bacterial cell as an episomal genetic element (e.g. plasmid or cosmid). Preferred origins of replication include, but are not limited to, the f1-ori and colE1.

The genetic construct may optionally comprise a selectable marker gene. As used herein, the term "selectable marker gene" includes any gene, which confers a phenotype on a cell in which it is expressed to facilitate the identification and/or selection of cells, which are transfected or transformed with a genetic construct of the invention. Suitable markers may be selected from markers that confer antibiotic or herbicide resistance. Cells containing the recombinant DNA will thus be able to survive in the presence of antibiotic or herbicide concentrations that kill untransformed cells. Examples of selectable marker genes include genes conferring resistance to antibiotics (such as nptII encoding neomycin phosphotransferase capable of phosphorylating neomycin and kanamycin, or hpt encoding hygromycin phosphotransferase capable of phosphorylating hygromycin), to herbicides (for example, bar which provides resistance to Basta; aroA or gox providing resistance against glyphosate), or genes that provide a metabolic trait (such as manA that allows plants to use mannose as sole carbon source). Visual marker genes result in the formation of colour (for example, beta-glucuronidase, GUS), luminescence (such as luciferase) or fluorescence (Green Fluorescent Protein, GFP, and derivatives thereof). Further examples of suitable selectable marker genes include the ampicillin resistance gene (Ampr), tetracycline resistance gene (Tcr), bacterial kanamycin resistance gene (Kanr), phosphinothricin resistance gene, and the chloramphenicol acetyltransferase (CAT) gene, amongst others The present invention also encompasses plants obtainable by the methods according to the present invention. The present invention therefore provides plants obtainable by the method according to the present invention, which plants have introduced therein an DP nucleic acid or variant thereof.

The invention also provides a method for the production of transgenic plants having improved growth characteristics, comprising introduction and expression in a plant of a DP nucleic acid or a variant thereof.

Accordingly, there is provided a method for the production of a transgenic plant comprising:
(a) introducing into a plant cell a DP nucleic acid or a variant thereof, preferably introducing a genetic construct as described hereinabove;
(b) cultivating said plant cell under conditions promoting plant growth.

The produced transgenic plants are characterised by improved plant growth characteristics relative to corresponding wild-type plants.

"Introducing" the DP nucleic acid or the genetic construct into the plant cell is preferably achieved by transformation. The term "transformation" as used herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention. The choice of tissue depends on the particular plant species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. Preferably, the DP nucleic acid is stably integrated in the genome of the plant cell, which may be achieved, for example, by using a plant transformation vector or a plant expression vector having T-DNA borders, which flank the nucleic acid to be introduced into the genome.

Transformation of a plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., 1882, Nature 296, 72-74; Negrutiu I. et al., June 1987, Plant Mol. Biol. 8, 363-373); electroporation of protoplasts (Shillito R. D. et al., 1985 Bio/Technol 3, 1099-1102); microinjection into plant material (Crossway A. et al., 1986, Mol. Gen Genet 202, 179-185); DNA or RNA-coated particle bombardment (Klein T. M. et al., 1987, Nature 327, 70) infection with (non-integrative) viruses and the like. A preferred method for the production of transgenic plants according to the invention is an *Agrobacterium*-mediated transformation method.

Transgenic rice plants are preferably produced via *Agrobacterium*-mediated transformation using any of the well-known methods for rice transformation, such as the ones described in any of the following: published European patent application EP1198985, Aldemita and Hodges (Planta, 1996, 199: 612-617,); Chan et al. (Plant Mol. Biol., 1993, 22 (3): 491-506,); Hiei et al. (Plant J., 1994, 6 (2): 271-282,); which disclosures are incorporated by reference herein as if fully set forth. In the case of corn transformation, the preferred method is as described in either Ishida at al. (Nat. Biotechnol., 1996, 14(6): 745-50) or Frame et al. (Plant Physiol., 2002, 129(1); 13-22), which disclosures are incorporated by reference herein as if fully set forth.

Generally after transformation, plant cells or cell groupings are selected for the presence of one or more markers, which are co-transformed with the DP gene.

The resulting transformed plant cell, cell grouping, or plant tissue, may then be used to regenerate a whole transformed plant via regeneration techniques well known to persons skilled in the art. Therefore, cultivating the plant cell under conditions promoting plant growth may encompass the steps of selecting and/or regenerating and/or growing to reach maturity.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, both techniques being well known to persons having ordinary skill in the art.

The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The invention also includes host cells containing an isolated nucleic acid molecule encoding a DP or a genetic construct as mentioned hereinbefore. Preferred host cells according to the invention are plant cells. Accordingly, there is provided plant cells, tissues, organs and whole plants that have been transformed with a genetic construct of the invention.

The present invention clearly extends to plants obtainable by any of the methods as described hereinbefore. The present invention extends to plants, which have increased expression levels of a DP nucleic acid and/or increased level and/or activity of a DP protein preferentially in shoot-tissue. The present invention extends to plants containing a genetic construct as described hereinabove. The plants according to the present invention have improved growth characteristics.

The present invention clearly also extends to any plant cell of the present invention and to all plant parts and propagules thereof. The present invention extends further to encompass the progeny of a primary transformed cell, tissue, organ or whole plant of the present invention, the only requirement being that progeny exhibit the same genotypic and/or phenotypic characteristic(s) as those of the parent plants, for example the plants produced by the methods according to the invention.

The invention also extends to any part of the plant according to the invention, preferably a harvestable part of a plant, such as, but not limited to, a seed, leaf, fruit, flower, stem culture, stem, rhizome, root, tuber, bulb and cotton fiber.

The present invention also relates to use of a nucleic acid encoding a DP protein or a variant thereof, under control of a shoot-tissue-preferred promoter for improving plant growth, preferably for increasing biomass.

The present invention also relates to a method for the production of plant biomass, comprising the step of growing a plant according to the present invention as described hereinabove.

DP nucleic acids or variants thereof or DP polypeptides or homologues thereof may find use in breeding programmes in which a DNA marker is identified which may be genetically linked to an DP gene or variant thereof. The DP or variants thereof or DP or homologues thereof may be used to define a molecular marker. This DNA or protein marker may then be used in breeding programs to select plants having altered growth characteristics. The DP gene or variant thereof may, for example, be a nucleic acid as represented by any one of SEQ ID NO 1, 3, 12, 14, 16, 18, 20 or 22.

Allelic variants of a DP may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place by, for example, PCR. This is followed by a selection step for selection of superior allelic variants of the sequence in question and which give rise improved growth characteristics in a plant. Selection is typically carried out by monitoring growth performance of plants containing different allelic variants of the sequence in question, for example, different allelic variants of any one of SEQ ID NO 1, 3, 12, 14, 16, 18, or 22. Growth performance may be monitored in a greenhouse or in the field. Further optional steps include crossing plants, in which the superior allelic variant was identified, with another plant. This could be used, for example, to make a combination of interesting phenotypic features.

A DP nucleic acid or variant thereof may also be used as probes for genetically and physically mapping the genes that they are a part of, and as markers for traits linked to those genes. Such information may be useful in plant breeding in order to develop lines with desired phenotypes. Such use of DP nucleic acids or variants thereof requires only a nucleic acid sequence of at least 15 nucleotides in length. The DP nucleic acids or variants thereof may be used as restriction fragment length polymorphism (RFLP) markers. Southern blots (Maniatis) of restriction-digested plant genomic DNA may be probed with the DP nucleic acids or variants thereof. The resulting banding patterns may then be subjected to genetic analyses using computer programs such as MapMaker (Lander et al. (1987) Genomics 1:174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the DP nucleic acid or variant thereof in the genetic map previously obtained using this population (Botstein et al. (1980) Am. J. Hum. Genet. 32:314-331).

The production and use of plant gene-derived probes for use in genetic mapping is described in Bematzky and Tanksley (1986) Plant Mol. Biol. Reporter 4:37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet. 7:149-154). Although current methods of FISH mapping favor use of large clones (several to several hundred KB; see Laan et al. (1995) Genome Res. 5:13-20), improvements in sensitivity may allow performance of FISH mapping using shorter probes.

A variety of nucleic acid amplification-based methods of genetic and physical mapping may be carried out using the nucleic acids. Examples include allele-specific amplification (Kazazian (1989) J. Lab. Clin. Med. 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

DP nucleic acids or variants thereof or DP polypeptides or homologues thereof may also find use as growth regulators. Since these molecules have been shown to be useful in improving the growth characteristics of plants, they would also be useful growth regulators, such as herbicides or growth stimulators. The present invention therefore provides a composition comprising a DP or variant thereof or a DP polypeptide or homologue thereof, together with a suitable carrier, diluent or excipient, for use as a growth regulator.

The methods according to the present invention result in plants having improved growth characteristics, as described hereinbefore. These advantageous growth characteristics may also be combined with other economically advantageous traits, such as further yield-enhancing traits, tolerance to various stresses, traits modifying various architectural features and/or biochemical and/or physiological features.

The present invention will now be described with reference to the following figures in which:

FIG. 1 is a map of the binary vector pEXP::AtDPb for expression in *Oryza sativa* of the *Arabidopsis thaliana* DPb gene (internal reference CDS006) under the control of the rice beta-expansin promoter (beta-EXPB9 promoter with internal reference PRO0061). The AtDPb expression cassette further comprises a T-zein and T-rbcS-deltaGA double transcription termination sequence. This expression cassette is located within the left border (LB repeat, LB Ti C58) and the right border (RB repeat, RB Ti C58) of the nopaline Ti plasmid. Within the T-DNA there is further provided a selectable and a screenable marker, both under control of a constitutive promoter and followed by polyA or a T-NOS transcription terminator sequence. This vector further comprises an origin of replication (pBR322 ori+bom) for bacterial replication and a bacterial selectable marker (Spe/SmeR) for bacterial selection.

FIG. 2 presents all the SEQ ID NO's used in the description of the present invention. In SEQ ID NO 2, the region which is typically conserved in DP proteins is underlined.

FIG. 3 shows an alignment of DP proteins with the location of the conserved consensus DPb motifs herein represented as SEQ ID NO 9 (motif 1), 10 (motif 2) and 11 (motif 3). Also the DNA binding domain of AtDPb and the dimerisation domain of AtDPb are indicated. The location of the highly conserved region, common to all DP proteins, is indicated with dashed brackets. Multiple sequence alignment across the entire sequences was done using CLUSTAL W (Higgins et al., (1994) Nucleic Acids Res. 22:4673-4680), with the BLOSSUM 62 matrix and with the parameters GAPOPEN 10, GAPEXT 0.05 and GAPDIST 8. The sequences are presented by their Genbank accession number.

Figure 4:
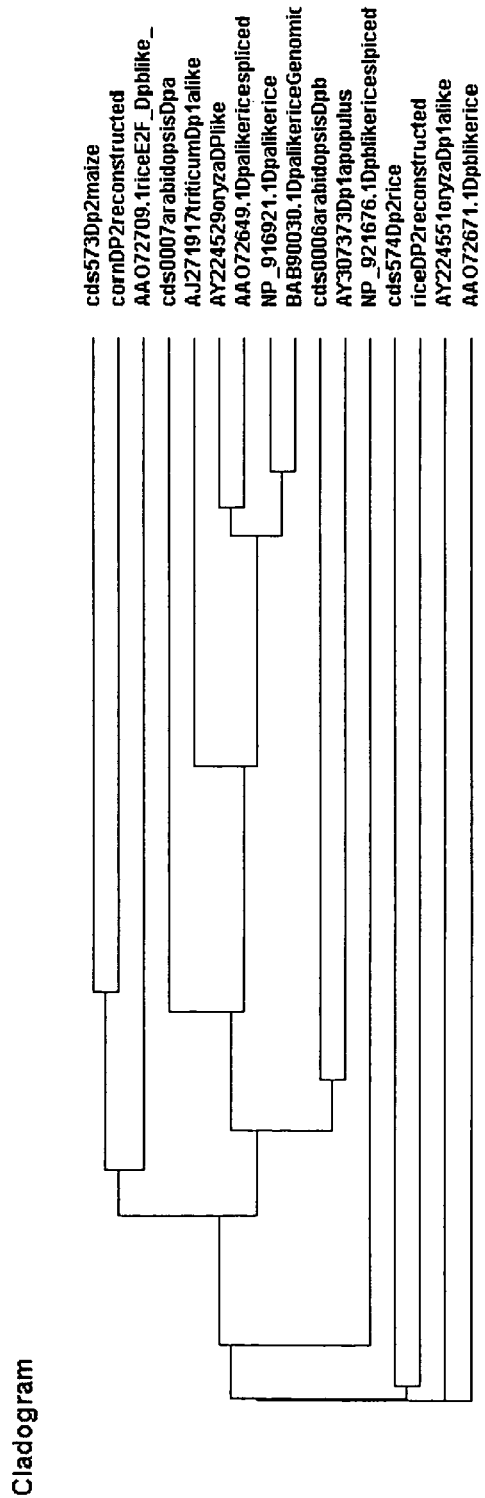

FIG. 4 shows the cladogram corresponding to the multiple alignment of FIG. 3. The cladogram view was generated by the program ClustalW. The sequences are presented by their. Genbank accession number.

FIG. 5 shows a phylogram view of DP proteins. The phylogram gives the length of the branches and the distance between the nodes in proportion to the evolutionary distance between the sequences. The cladogram view was generated by the program ClustalW. Two groups of DP proteins may be distinguished based on the presence or absence of the KKKK/RR (SEQ ID NO: 10) motif.

EXAMPLES

The present invention will now be described with reference to the following examples, which are by way of illustration alone.

DNA Manipulation

Unless otherwise stated, recombinant DNA techniques are performed according to standard protocols described in Sambrook (2001) Molecular Cloning: a laboratory manual, 3rd Edition Cold Spring Harbor Laboratory Press, CSH, New York or in Volumes 1 and 2 of Ausubel et al. (1998), Current Protocols in Molecular Biology. Standard materials and methods for plant molecular work are described in Plant Molecular Biology Labfase (1993) by R. D. D. Croy, published by BIOS Scientific Publications Ltd (UK) and Blackwell Scientific Publications (UK).

Example 1

Cloning of *Arabidopsis thaliana* Dpb

The *Arabidopsis* DPb gene (internal reference CDS006) was amplified by PCR using as template an *Arabidopsis thaliana* seedling cDNA library (Invitrogen, Paisley, UK). After reverse transcription of RNA extracted from seedlings, the cDNA fragments were cloned into pCMV Sport 6.0. Average insert size of the cDNA library was 1.5 kb, and original number of clones was about $1.59 \times 10^7$ cfu. The original titer of $9.6 \times 10^5$ cfu/ml was brought to $6 \times 10^{11}$ cfu/ml after amplification of the library. After plasmid extraction of the clones, 200 ng of plasmid template was used in a 50 µl PCR mix. The primers used for PCR amplification, prm0319 with the sequence 5' GGGGACAAGTTTGTACAAAAAAGCAG-GCTTCACAATGACAACTACTGGG TCTAATTCT 3' (SEQ ID NO 5) and prm0320 with the sequence 5' GGG-GACCACTTTGTAC AAGAAAGCTGGGTTCAATTCTC-CGGCTTCAT 3' (SEQ ID NO 6), comprise an AttB site for Gateway recombination cloning (italics). PCR was performed using Hifi Taq DNA polymerase in standard conditions. A PCR fragment of the expected length was amplified and purified also using standard methods. The first step of the Gateway procedure, the BP reaction, was then performed, during which the PCR fragment recombines in vivo with the pDONR201 plasmid to produce the "entry clone", p0424. Plasmid pDONR201 was purchased from Invitrogen, as part of the Gateway® technology.

Example 2

Vector Construction (pEXP::AtDPb)

The entry clone p0424 was subsequently used in an LR reaction with p3169, a destination vector used for *Oryza sativa* transformation. This vector contains as functional elements within the T-DNA borders, a plant selectable marker, a screenable marker and a Gateway cassette intended for LR in vivo recombination with the sequence of interest already cloned in the entry clone. Upstream of this Gateway cassette lies the rice beta-expansin promoter (internal reference PRO061) for shoot-tissue-preferred expression of the gene of interest. After the LR recombination step, the resulting expression vector pEXP::AtDPb (FIG. 1) was transformed into *Agrobacterium* strain LBA4044 and subsequently into *Oryza sativa* var. *Nipponbare* plants. Transformed rice plants were allowed to grown and were examined for various growth characteristics as described in Example 3.

Example 3

Evaluation of T0, T1 and T2 Rice Plants Transformed with pEXP::AtDPb

Approximately 15 to 20 independent T0 transformants were generated. The primary transformants were transferred from tissue culture chambers to a greenhouse for growing and harvest of T1 seed. Six events of which the T1 progeny segregated 3/1 for presence/absence of the transgene were retained. "Null plants" or "Null segregants" or "Nullizygotes" are the plants treated in the same way as a transgenic plant, but from which the transgene has segregated. Null plants can also be described as the homozygous negative transformants. For each of these events, approximately 10 T1 seedlings containing the transgene (hetero- and homo-zygotes), and approximately 10 T1 seedlings lacking the transgene (nullizygotes), were selected by PCR.

Based on the results of the T1 evaluation, three events, which showed improved growth characteristics at the T1 level, were chosen for further characterisation in the T2 and further generations. To this extent, seed batches from the positive T1 plants (both hetero- and homozygotes), were screened by monitoring marker expression. For each chosen event, the heterozygote seed batches were then selected for T2 evaluation. An equal number of positive and negative within each seed batch were transplanted for evaluation in the greenhouse (i.e., for each event 40 plants, of which 20 positives for the transgene and 20 negative for the transgene, were grown). For the three events therefore, a total amount of 120 plants was evaluated in the T2 generation.

T1 and T2 plants were transferred to a greenhouse and were evaluated for vegetative growth parameters, as described hereunder.

(I) Statistical Analysis of Numeric Data

A two factor ANOVA (analyses of variance) corrected for the unbalanced design was used as statistical evaluation model for the numeric values of the observed plant phenotypic characteristics. The numerical values are submitted to a t-test and an F test. The p-value is obtained by comparing the t value to the t distribution or alternatively, by comparing the F value to the F distribution. The p-value stands the probability that the null hypothesis (null hypothesis being "there is no effect of the transgene") is correct.

A t-test was performed on all the values of all plants of one event. Such a t-test was repeated for each event and for each growth characteristic. The t-test was carried out to check for an effect of the gene within one transformation event, also named herein a "line-specific effect". In the t-test, the threshold for a significant line-specific effect is set at 10% probability level. Therefore, data with a p-value of the t test under 10% mean that the phenotype observed in the transgenic plants of that line is caused by the presence of the gene. Within one population of transformation events, some events may be under or below this threshold. This difference may be due to the difference in position of the transgene in the genome. It is not uncommon that a gene might only have an effect in certain positions of the genome. Therefore, the above-mentioned "line-specific effect" is also referred to as "position-dependent effect".

An F-test was carried out on all the values measured for all plants of all events. An F-test was repeated for each growth characteristic. The F-test was carried out to check for an effect of the gene over all the transformation events and to verify an overall effect of the gene, also named herein "gene effect". In the F-test, the threshold for a significant global gene effect is set at 5% probability level. Therefore, data with a p-value of the F test under 5% mean that the observed phenotype is caused by more than just the presence of the gene and or the position of the transgene in the genome. A "gene effect" is an indication for the wide applicability of the gene in transgenic plants.

(II) Vegetative Growth Measurements

The selected plants were grown in a greenhouse. Each plant received a unique barcode label to link unambiguously the phenotyping data to the corresponding plant. The selected plants were grown on soil in 10 cm diameter pots under the following environmental settings: photoperiod=11.5 h, daylight intensity=30,000 lux or more, daytime temperature=28° C. or higher, night time temperature=22° C., relative humidity=60-70%. Transgenic plants and the corresponding nullizygotes were grown side-by-side at random positions. From the stage of sowing until the stage of maturity (which is the stage were there is no more increase in biomass) the plants were passed weekly through a digital imaging cabinet. At each time point digital images (2048×1536 pixels, 16 million colours) were taken of each plant from at least 6 different angles. The parameters described below were derived in an automated way from the digital images using image analysis software.

Aboveground Area

Plant above-ground area was determined by counting the total number of pixels from above-ground plant parts discriminated from the background. This value was averaged for the pictures taken on the same time point from the different angles and was converted to a physical surface value expressed in square mm by calibration. Experiments show that the above-ground plant area, which corresponds to the total maximum area, measured this way correlates with the biomass of plant parts above-ground.

On average, pEXP::DPb transgenic plants in T1 generation showed an increase in above-ground area of 8% with a p-value of 0.08. The best of the 3 positive T1 lines showed an increase in above-ground area of 30% with a p-value of 0.01. In the T2 generation this line showed 18% increase in above-ground area with a p-value of 0.03.

Example 4

GUS Expression Driven by Beta Expansin Promoter

The beta-expansin promoter was cloned into the pDONR201 entry plasmid of the Gateway™ system (Life Technologies) using the "BP recombination reaction". The identity and base pair composition of the cloned insert was confirmed by sequencing and additionally, the resulting plasmid was tested via restriction digests.

In order to clone the promoter in front of a reporter gene, each entry clone was subsequently used in an "LR recombination reaction" (Gateway™) with a destination vector. This destination vector was designed to operably link the promoter to the *Escherichia coli* beta-glucuronidase (GUS) gene via the substitution of the Gateway recombination cassette in front of the GUS gene. The resulting reporter vectors, comprising the promoter operably linked to GUS were subsequently transformed into *Agrobacterium* strain LBA4044 and subsequently into rice plants using standard transformation techniques.

Transgenic rice plants were generated from transformed cells. Plant growth was performed under normal conditions.

The plants or plant parts to be tested were covered with 90% ice-cold acetone and incubated for 30 min at 4° C. After 3 washes of 5 min with Tris buffer [15.76 g Trizma HCl (Sigma T3253)+2,922 g NaCl in 1 liter bi-distilled water, adjusted to pH 7.0 with NaOH], the material was covered by a Tris/ferricyanate/X-Gluc solution [9.8 ml Tris buffer+0.2 ml ferricyanate stock (0.33 g Potassium ferricyanate (Sigma P3667) in 10 ml Tris buffer)+0.2 ml X-Gluc stock (26.1 mg X-Gluc (Europa Bioproducts ML 113A) in 500 µl DMSO)]. Vacuum infiltration was applied for 15 to 30 minutes. The plants or plant parts were incubated for up to 16 hours at 37° C. until development of blue colour was visible. The samples were washed 3 times for 5 minutes with Tris buffer. Chlorophyll was extracted in ethanol series of 50%, 70% and 90% (each for 30 minutes).

The invention claimed is:

1. A method for increasing above ground biomass in a plant species comprising the steps of: (a) transforming plants of a species with a nucleic acid molecule comprising a nucleotide sequence encoding a DP polypeptide having at least 90% amino acid sequence identity to an amino acid sequence selected from the group consisting of SEQ ID NO: 2, SEQ ID NO: 4, SEQ ID NO: 13, SEQ ID NO: 15, SEQ ID NO: 17, SEQ ID NO: 19, SEQ ID NO: 21, SEQ ID NO: 23, SEQ ID NO: 24, SEQ ID NO: 25, SEQ ID NO: 26, SEQ ID NO: 27, SEQ ID NO: 28 and SEQ ID NO: 29, and wherein the nucleic acid sequence is operably linked to a shoot-specific promoter; (b) expressing said DP polypeptide from said promoter in the transformed plants of said plant species; and (c) selecting a transformed plant from the step (b) comprising said nucleic acid molecule, and which exhibits increase in above ground biomass as compared to an untransformed control plant of the same plant species.

2. A method for increasing above-ground area of a plant, comprising the steps of: (a) transforming plant cells of a plant with a genetic construct which comprises a nucleic acid sequence that encodes a DP polypeptide having at least 90% amino acid sequence identity to an amino acid sequence selected from the group consisting of SEQ ID NO: 2, SEQ ID NO: 4, SEQ ID NO: 13, SEQ ID NO: 15, SEQ ID NO: 17, SEQ ID NO: 19, SEQ ID NO: 21, SEQ ID NO: 23, SEQ ID NO: 24, SEQ ID NO: 25, SEQ ID NO: 26, SEQ ID NO: 27, SEQ ID NO: 28 and SEQ ID NO: 29, wherein said nucleic acid sequence is operably linked to a shoot-specific promoter; (b) expressing said DP polypeptide in the transformed plant cells; (c) regenerating transgenic plants from said transformed plant cells; and (d) identifying a transgenic plant from said transgenic plants which exhibits an increase in above-ground area as compared to an untransformed control plant of the same species.

3. A method for increasing above-ground area of a plant according to claim 2, wherein said shoot-specific promoter is a shoot-specific promoter that is at least 5 times stronger in shoot than in other plant organs.

4. A method for increasing above-ground biomass or above-ground area of a plant, comprising the steps of: (a) transforming plant cells of a plant with a genetic construct which comprises a nucleic acid sequence that encodes a DP polypeptide comprising an amino acid sequence having at least 90% amino acid sequence identity to an amino acid sequence selected from the group consisting of SEQ ID NO: 2, SEQ ID NO: 4, SEQ ID NO: 13, SEQ ID NO: 15, SEQ ID NO: 17, SEQ ID NO: 19, SEQ ID NO: 21, SEQ ID NO: 23, SEQ ID NO: 24, SEQ ID NO: 25, SEQ ID NO: 26, SEQ ID NO: 27, SEQ ID NO: 28 and SEQ ID NO: 29, and wherein the nucleic acid sequence is operably linked to either a beta-expansin or a protochlorophyll reductase shoot-tissue-preferred promoter; (b) expressing said DP polypeptide in the transformed plant cells; (c) regenerating transgenic plants from said transformed plant cells; and (d) identifying a transgenic plant from said transgenic plants, which exhibits increased above-ground biomass or increased above-ground area as compared to a wild type untransformed plant of the same species.

5. The method of claim 1, wherein said increased above-ground biomass further comprises increased seed yield.

* * * * *